(12) United States Patent
Fraden et al.

(10) Patent No.: US 8,592,221 B2
(45) Date of Patent: Nov. 26, 2013

(54) MANIPULATION OF FLUIDS, FLUID COMPONENTS AND REACTIONS IN MICROFLUIDIC SYSTEMS

(75) Inventors: Seth Fraden, Newton, MA (US); Hakim Boukellal, Paris (FR); Yanwei Jia, Medford, MA (US); Seila Selimovic, Bronx, NY (US); Amy Rowat, Cambridge, MA (US); Jeremy Agresti, Cambridge, MA (US); David A. Weitz, Bolton, MA (US)

(73) Assignees: Brandeis University; President and Fellows of Harvard College

( * ) Notice: Subject to any disclaimer, the term of this patent is extended or adjusted under 35 U.S.C. 154(b) by 846 days.

(21) Appl. No.: 12/595,107

(22) PCT Filed: Apr. 18, 2008

(86) PCT No.: PCT/US2008/005009
§ 371 (c)(1),
(2), (4) Date: May 18, 2010

(87) PCT Pub. No.: WO2008/130623
PCT Pub. Date: Oct. 30, 2008

(65) Prior Publication Data
US 2010/0252118 A1  Oct. 7, 2010

Related U.S. Application Data

(60) Provisional application No. 60/925,357, filed on Apr. 19, 2007.

(51) Int. Cl.
*G01F 11/00* (2006.01)

(52) U.S. Cl.
USPC ............ 436/180; 422/502; 422/503; 137/2; 137/14

(58) Field of Classification Search
USPC ............... 422/502–504, 507, 509; 137/2, 14; 436/180
See application file for complete search history.

(56) References Cited

U.S. PATENT DOCUMENTS

| 2,097,692 A | 11/1937 | Fiegel |
| 2,164,172 A | 6/1939 | Dalton |

(Continued)

FOREIGN PATENT DOCUMENTS

| AU | 2004225691 B2 | 10/2004 |
| CA | 2520548 A1 | 9/2004 |

(Continued)

OTHER PUBLICATIONS

Adang, A.E. et al., The contribution of combinatorial chemistry to lead generation: an interim analysis, Curr Med Chem 8: 985-998 (2001).

(Continued)

*Primary Examiner* — Paul Hyun
(74) *Attorney, Agent, or Firm* — Brown Rudnick LLP; Thomas C. Meyers

(57) ABSTRACT

Microfluidic structures and methods for manipulating fluids, fluid components, and reactions are provided. In one aspect, such structures and methods can allow production of droplets of a precise volume, which can be stored/maintained at precise regions of the device. In another aspect, microfluidic structures and methods described herein are designed for containing and positioning components in an arrangement such that the components can be manipulated and then tracked even after manipulation. For example, cells may be constrained in an arrangement in microfluidic structures described herein to facilitate tracking during their growth and/or after they multiply.

26 Claims, 27 Drawing Sheets

(56) References Cited

U.S. PATENT DOCUMENTS

| | | |
|---|---|---|
| 2,656,508 A | 10/1953 | Coulter |
| 2,692,800 A | 10/1954 | Nichols et al. |
| 2,797,149 A | 6/1957 | Skeggs |
| 2,879,141 A | 3/1959 | Skeggs |
| 2,971,700 A | 2/1961 | Peeps |
| 3,479,141 A | 11/1969 | Smythe et al. |
| 3,608,821 A | 9/1971 | Simm et al. |
| 3,698,635 A | 10/1972 | Sickles |
| 3,816,331 A | 6/1974 | Brown, Jr. et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Allred |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,585,209 A | 4/1986 | Aine et al. |
| 4,618,476 A | 10/1986 | Columbus |
| 4,628,040 A | 12/1986 | Green |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,091,652 A | 2/1992 | Mathies et al. |
| 5,096,615 A | 3/1992 | Prescott et al. |
| 5,122,360 A | 6/1992 | Harris et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,344,594 A | 9/1994 | Sheridon |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,475,096 A | 12/1995 | Gold et al. |
| 5,480,614 A | 1/1996 | Kamahori |
| 5,486,335 A | 1/1996 | Wilding et al. |
| 5,498,392 A | 3/1996 | Wilding et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,604,097 A | 2/1997 | Brenner |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli et al. |
| 5,779,868 A | 7/1998 | Parce et al. |
| 5,783,431 A | 7/1998 | Peterson et al. |
| 5,840,506 A | 11/1998 | Giordano |
| 5,846,719 A | 12/1998 | Brenner et al. |
| 5,849,491 A | 12/1998 | Radomski et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks, Jr. et al. |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,884,846 A | 3/1999 | Tan |
| 5,887,755 A | 3/1999 | Hood, III |
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |

(56) References Cited

U.S. PATENT DOCUMENTS

| | | |
|---|---|---|
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,068,199 A | 5/2000 | Coffee |
| 6,080,295 A | 6/2000 | Parce et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,149,789 A | 11/2000 | Benecke et al. |
| 6,150,180 A | 11/2000 | Parce et al. |
| 6,150,516 A | 11/2000 | Brenner et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Ganan-Calvo |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,294,344 B1 | 9/2001 | O'Brien |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,520,425 B1 | 2/2003 | Reneker |
| 6,524,456 B1 | 2/2003 | Ramsey et al. |
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Legrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 * | 7/2003 | McNeely et al. ............... 137/14 |
| 6,592,321 B2 | 7/2003 | Bonker et al. |
| 6,592,821 B1 | 7/2003 | Wada et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B1 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |

(56) References Cited

U.S. PATENT DOCUMENTS

| | | |
|---|---|---|
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Orntoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan et al. |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,665 B2 | 7/2008 | Brenner |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,622,081 B2 | 11/2009 | Chou et al. |
| 7,632,562 B2 | 12/2009 | Nair et al. |
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,678,565 B2 | 3/2010 | Schurmann-Mader |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| 7,814,175 B1 | 10/2010 | Chang et al. |
| 7,824,889 B2 | 11/2010 | Vogelstein et al. |
| 7,897,044 B2 | 3/2011 | Hoyos et al. |
| 7,897,341 B2 | 3/2011 | Griffiths et al. |
| 7,901,939 B2 | 3/2011 | Ismagilov et al. |
| 7,968,287 B2 | 6/2011 | Griffiths et al. |
| 8,012,382 B2 | 9/2011 | Kim et al. |
| 8,153,402 B2 | 4/2012 | Holliger et al. |
| 2001/0010338 A1 | 8/2001 | Ganan-Calvo |
| 2001/0020011 A1 | 9/2001 | Mathiowitz et al. |
| 2001/0023078 A1 | 9/2001 | Bawendi et al. |
| 2001/0029983 A1 | 10/2001 | Unger et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0036139 A1 | 3/2002 | Becker et al. |
| 2002/0058332 A1 | 5/2002 | Quake et al. |
| 2002/0067800 A1 | 6/2002 | Newman et al. |
| 2002/0119459 A1 | 8/2002 | Griffiths |
| 2002/0143437 A1* | 10/2002 | Handique et al. ............ 700/266 |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2002/0166582 A1* | 11/2002 | O'Connor et al. ......... 137/15.18 |
| 2003/0012586 A1 | 1/2003 | Iwata et al. |
| 2003/0015425 A1 | 1/2003 | Bohm et al. |
| 2003/0017579 A1 | 1/2003 | Corn et al. |

(56) References Cited

U.S. PATENT DOCUMENTS

| | | |
|---|---|---|
| 2003/0039169 A1 | 2/2003 | Ehrfeld et al. |
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0124586 A1 | 7/2003 | Griffiths et al. |
| 2003/0144260 A1 | 7/2003 | Gilon |
| 2003/0148544 A1 | 8/2003 | Nie et al. |
| 2003/0183525 A1 | 10/2003 | Elrod et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |
| 2004/0068019 A1 | 4/2004 | Higuchi et al. |
| 2004/0069632 A1 | 4/2004 | Ripoll |
| 2004/0071781 A1 | 4/2004 | Chattopadhyay et al. |
| 2004/0079881 A1 | 4/2004 | Fischer et al. |
| 2004/0096515 A1 | 5/2004 | Bausch et al. |
| 2004/0115224 A1 | 6/2004 | Ohno |
| 2004/0134854 A1 | 7/2004 | Higuchi |
| 2004/0136497 A1 | 7/2004 | Meldrum et al. |
| 2004/0146921 A1 | 7/2004 | Eveleigh et al. |
| 2004/0159633 A1 | 8/2004 | Whitesides et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0188254 A1 | 9/2004 | Spaid |
| 2004/0224419 A1 | 11/2004 | Zheng et al. |
| 2004/0253731 A1 | 12/2004 | Holliger et al. |
| 2004/0258203 A1 | 12/2004 | Yamano et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0129582 A1 | 6/2005 | Breidford et al. |
| 2005/0152908 A1 | 7/2005 | Liew et al. |
| 2005/0164239 A1 | 7/2005 | Griffiths et al. |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0207940 A1 | 9/2005 | Butler et al. |
| 2005/0221339 A1 | 10/2005 | Griffiths et al. |
| 2005/0226742 A1 | 10/2005 | Unger et al. |
| 2005/0227264 A1 | 10/2005 | Nobile et al. |
| 2005/0260566 A1 | 11/2005 | Fischer et al. |
| 2005/0272159 A1 | 12/2005 | Ismagilov et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0036348 A1 | 2/2006 | Handique et al. |
| 2006/0046257 A1 | 3/2006 | Pollock et al. |
| 2006/0051329 A1 | 3/2006 | Lee et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0252057 A1 | 11/2006 | Raponi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269971 A1 | 11/2006 | Diamandis |
| 2006/0281089 A1 | 12/2006 | Gibson et al. |
| 2007/0003442 A1 | 1/2007 | Link et al. |
| 2007/0026439 A1 | 2/2007 | Faulstich et al. |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0120899 A1 | 5/2007 | Ohnishi et al. |
| 2007/0154889 A1 | 7/2007 | Wang |
| 2007/0166705 A1 | 7/2007 | Milton et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0259351 A1 | 11/2007 | Chinitz et al. |
| 2007/0259368 A1 | 11/2007 | An et al. |
| 2007/0259374 A1 | 11/2007 | Griffiths et al. |
| 2007/0292869 A1 | 12/2007 | Becker et al. |
| 2008/0003142 A1 | 1/2008 | Link et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0138806 A1 | 6/2008 | Chow et al. |
| 2008/0166772 A1 | 7/2008 | Hollinger et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0268473 A1 | 10/2008 | Moses et al. |
| 2008/0269157 A1 | 10/2008 | Srivastava et al. |
| 2008/0274908 A1 | 11/2008 | Chang |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0012187 A1 | 1/2009 | Chu et al. |
| 2009/0017463 A1 | 1/2009 | Bhowmick |
| 2009/0021728 A1 | 1/2009 | Heinz et al. |

(56) References Cited

U.S. PATENT DOCUMENTS

| | | |
|---|---|---|
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0246788 A1 | 10/2009 | Albert et al. |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0022414 A1 | 1/2010 | Link et al. |
| 2010/0035252 A1 | 2/2010 | Rothberg et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0124759 A1 | 5/2010 | Wang et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0142734 A1 | 6/2011 | Ismagliov et al. |
| 2011/0174622 A1 | 7/2011 | Ismagilov et al. |
| 2011/0176966 A1 | 7/2011 | Ismagilov et al. |
| 2011/0177494 A1 | 7/2011 | Ismagilov et al. |
| 2011/0177586 A1 | 7/2011 | Ismagilov et al. |
| 2011/0177609 A1 | 7/2011 | Ismagilov et al. |
| 2011/0188717 A1 | 8/2011 | Baudry et al. |
| 2011/0190146 A1 | 8/2011 | Boehm et al. |
| 2011/0244455 A1 | 10/2011 | Larson et al. |
| 2011/0250597 A1 | 10/2011 | Larson et al. |
| 2011/0275063 A1 | 11/2011 | Weitz et al. |
| 2012/0010098 A1 | 1/2012 | Griffiths et al. |
| 2012/0015382 A1 | 1/2012 | Weitz et al. |
| 2012/0015822 A1 | 1/2012 | Weitz et al. |

FOREIGN PATENT DOCUMENTS

| | | |
|---|---|---|
| DE | 4308839 C2 | 4/1997 |
| EP | 0047130 B1 | 2/1985 |
| EP | 0249007 A3 | 3/1991 |
| EP | 0476178 A1 | 3/1992 |
| EP | 0540281 B1 | 7/1996 |
| EP | 0528580 B1 | 12/1996 |
| EP | 0895120 | 2/1999 |
| EP | 1741482 | 1/2007 |
| EP | 2127736 | 12/2009 |
| GB | 0114854.3 | 4/1969 |
| GB | 1446998 | 8/1976 |
| GB | 2005224 | 4/1979 |
| GB | 2047880 | 12/1980 |
| GB | 2062225 | 5/1981 |
| GB | 2064114 | 6/1981 |
| GB | 2097692 A | 11/1982 |
| GB | 0221053.2 | 6/1989 |
| WO | WO-84/02000 | 5/1984 |
| WO | WO-91/05058 | 4/1991 |
| WO | WO-91/07772 | 5/1991 |
| WO | WO-92/03734 | 3/1992 |
| WO | WO-92/21746 | 12/1992 |
| WO | WO-93/03151 | 2/1993 |
| WO | WO-93/08278 | 4/1993 |
| WO | WO-93/22053 | 11/1993 |
| WO | WO-93/22054 | 11/1993 |
| WO | WO-93/22055 | 11/1993 |
| WO | WO-93/22058 | 11/1993 |
| WO | WO-93/22421 | 11/1993 |
| WO | WO-94/16332 | 7/1994 |
| WO | WO-94/23738 | 10/1994 |
| WO | WO-94/24314 | 10/1994 |
| WO | WO-94/26766 | 11/1994 |
| WO | WO-98/00705 | 1/1995 |
| WO | WO-95/11922 | 5/1995 |
| WO | WO-95/19922 | 7/1995 |
| WO | WO-95/24929 | 9/1995 |
| WO | WO-95/33447 | 12/1995 |
| WO | WO-96/34112 | 10/1996 |
| WO | WO-96/38730 | 12/1996 |
| WO | WO-96/40062 | 12/1996 |
| WO | WO-96/40723 | 12/1996 |
| WO | WO-97/00125 | 1/1997 |
| WO | WO-97/00442 | 1/1997 |
| WO | WO-97/04297 | 2/1997 |
| WO | WO-97/04748 | 2/1997 |
| WO | WO-97/23140 | 7/1997 |
| WO | WO-97/28556 | 8/1997 |
| WO | WO-97/39814 | 10/1997 |
| WO | WO-97/40141 | 10/1997 |
| WO | WO-97/45644 | 12/1997 |
| WO | WO-97/47763 | 12/1997 |
| WO | WO-98/00231 | 1/1998 |
| WO | WO-98/02237 | 1/1998 |
| WO | WO-98/10267 | 3/1998 |
| WO | WO-98/13502 | 4/1998 |
| WO | WO-98/23733 | 6/1998 |
| WO | WO-98/31700 | 7/1998 |
| WO | WO-98/33001 | 7/1998 |
| WO | WO-98/34120 | 8/1998 |
| WO | WO-98/37186 | 8/1998 |
| WO | WO-98/41869 | 9/1998 |
| WO | WO-98/52691 | 11/1998 |
| WO | WO-98/58085 | 12/1998 |
| WO | WO-99/02671 | 1/1999 |
| WO | WO-99/22858 | 5/1999 |
| WO | WO-99/28020 | 6/1999 |
| WO | WO-99/31019 | 6/1999 |
| WO | WO-99/54730 | 10/1999 |
| WO | WO-99/61888 | 12/1999 |
| WO | WO-00/04139 | 1/2000 |
| WO | WO-00/47322 | 2/2000 |
| WO | WO-00/52455 | 2/2000 |
| WO | WO-00/40712 | 6/2000 |
| WO | WO-00/61275 | 10/2000 |
| WO | WO-00/70080 | 11/2000 |
| WO | WO-00/76673 | 12/2000 |
| WO | WO-01/12327 | 2/2001 |
| WO | WO-01/14589 | 3/2001 |
| WO | WO-01/18244 | 3/2001 |
| WO | WO-01/64332 | 9/2001 |
| WO | WO-01/68257 | 9/2001 |
| WO | WO-01/69289 | 9/2001 |

(56) References Cited

FOREIGN PATENT DOCUMENTS

| | | |
|---|---|---|
| WO | WO-01/72431 | 10/2001 |
| WO | WO-01/80283 | 10/2001 |
| WO | WO-02/18949 | 3/2002 |
| WO | WO-02/022869 | 3/2002 |
| WO | WO-02/23163 | 3/2002 |
| WO | WO-02/031203 | 4/2002 |
| WO | WO-02/047665 | 6/2002 |
| WO | WO-02/060275 | 8/2002 |
| WO | WO-02/078845 | 10/2002 |
| WO | WO-02/103011 | 12/2002 |
| WO | WO-02/103363 | 12/2002 |
| WO | WO-03/011443 | 2/2003 |
| WO | WO-03/037302 | 5/2003 |
| WO | WO-03/044187 | 5/2003 |
| WO | WO-03/078659 | 9/2003 |
| WO | WO-03/099843 | 12/2003 |
| WO | WO-2004/002627 | 1/2004 |
| WO | WO-2004/018497 | 3/2004 |
| WO | WO-2004/024917 | 3/2004 |
| WO | WO-2004/038363 | 5/2004 |
| WO | WO-2004/069849 | 8/2004 |
| WO | WO-2004/074504 | 9/2004 |
| WO | WO-2004/083443 | 9/2004 |
| WO | WO-2004/087308 | 10/2004 |
| WO | WO-2004/088314 | 10/2004 |
| WO | WO-2004/091763 | 10/2004 |
| WO | WO-2004/102204 | 11/2004 |
| WO | WO-2004/103565 | 12/2004 |
| WO | WO-2005/000970 | 1/2005 |
| WO | WO-2005/002730 | 1/2005 |
| WO | WO-2005/021151 | 3/2005 |
| WO | WO-2005/103106 | 11/2005 |
| WO | WO-2005/118138 | 12/2005 |
| WO | WO-2006/002641 | 1/2006 |
| WO | WO-2006/009657 | 1/2006 |
| WO | WO-2006/027757 | 3/2006 |
| WO | WO-2006/038035 | 4/2006 |
| WO | WO-2006/040551 | 4/2006 |
| WO | WO-2006/040554 | 4/2006 |
| WO | WO-2006/078841 | 7/2006 |
| WO | WO-2006/096571 | 9/2006 |
| WO | WO-2006/101851 | 9/2006 |
| WO | WO-2007/021343 | 2/2007 |
| WO | WO-2007/030501 | 3/2007 |
| WO | WO-2007/081385 | 7/2007 |
| WO | WO-2007/081387 | 7/2007 |
| WO | WO-2007/089541 | 8/2007 |
| WO | WO-2007/114794 | 10/2007 |
| WO | WO-2007/123744 | 11/2007 |
| WO | WO-2007/133710 | 11/2007 |
| WO | WO-2007/138178 | 12/2007 |
| WO | WO-2008/021123 | 2/2008 |
| WO | WO-2008/063227 | 5/2008 |
| WO | WO-2008/097559 | 8/2008 |
| WO | WO-2008/121342 | 10/2008 |
| WO | WO-2008/130623 | 10/2008 |
| WO | WO-2009/029229 | 3/2009 |
| WO | WO-2010/040006 | 4/2010 |
| WO | WO-2010/056728 | 5/2010 |
| WO | WO-2010/151776 | 12/2010 |
| WO | WO-2011/042564 | 4/2011 |

OTHER PUBLICATIONS

Affholter and F. Arnold, Engineering a Revolution, Chemistry in Britain, Apr. 1999, p. 48.

Agrawal and Tang, Site-specific functionalization of oligodeoxynucleotides for non-radioactive labelling, Tetrahedron Letters 31:1543-1546 (1990).

Aharoni et al., High-Throughput screens and selections of enzyme-encoding genes, Curr Opin Chem Biol, 9(2): 210-6 (2005).

Ahn et al., Dielectrophoretic manipulation of drops for high-speed microluidic sorting devices, Applied Phys Lett 88, 024104 (2006).

Allen et al., High throughput fluorescence polarization: a homogeneous alternative to radioligand binding for cell surface receptors J Biomol Screen. 5(2):63-9 (2000).

Altman et al., Solid-state laser using a rhodamine-doped silica gel compound, IEEE Photonics technology letters 3(3):189-190 (1991).

Amstutz, P. et al., In vitro display technologies: novel developments and applications. Curr Opin Biotechnol, 12, 400-405 (2001).

Anarbaev et al., Klenow fragment and DNA polymerase alpha-primase fromserva calf thymus in water-in-oil microemulsions, Biochim Biophy Acta 1384:315-324 (1998).

Anderson et al., Preparation of a cell-free protein-synthesizing system from wheat germ, Methods Enzymol 101:635-44 (1983).

Anderson, J.E., Restriction endonucleases and modification methylases, Curr. Op. Struct. Biol., 3:24-30 (1993).

Ando, S. et al., PLGA microspheres containing plasmid DNA: preservation of supercoiled DNA via cryopreparation and carbohydrate stabilization, J Pharm Sci, 88(1):126-130 (1999).

Angell et al., Silicon micromechanical devices, Scientific American 248:44-55 (1983).

Anhuf et al., Determination of SMN1 and SMN2 copy number using TaqMan technology, Hum Mutat 22(1):74-78 (2003).

Anna et al., Formation of dispersions using flow focusing in microchannels, Applied Physics Letters,82(3): 364-366 (2003).

Arkin, M.R. et al., Probing the importance of second sphere residues in an esterolytic antibody by phage display, J Mol Biol 284(4):1083-94 (1998).

Armstrong et al., Multiple-Component Condensation Strategies for Combinatorial Library Synthesis, Acc. Chem. Res. 29(3):123-131 (1996).

Ashkin et al., Optical trapping and manipulation of single cells using infrared laser beams, Nature 330:769-771 (1987).

Ashkin and Dziedzic, Optical trapping and manipulation of viruses and bacteria, Science 235(4795):1517-20 (1987).

Atwell, S. & Wells, J.A., Selection for Improved Subtiligases by Phage Display, PNAS 96: 9497-9502(1999).

Auroux, Pierre-Alain et al., Micro Total Analysis Systems. 2. Analytical Standard Operations and Applications, Analytical Chemistry, vol. 74, No. 12, 2002, pp. 2637-2652.

Baccarani et al., *Escherichia coli* dihydrofolate reductase: isolation and characterization of tWO isozymes, Biochemistry 16(16):3566-72 (1977).

Baez et al., Glutathione transferases catalyse the detoxication of oxidized metabolites (o-quinones) of catecholamines and may serve as an antioxidant system preventing degenerative cellular processes, Biochem. J 324:25-28 (1997).

Baker, M., Clever PCR: more genotyping, smaller volumes, Nature Methods 7:351-356 (2010).

Ball and Schwartz, CMATRIX: software for physiologically based pharmacokinetic modeling using a symbolic matrix representation system, Comput Biol Med 24(4):269-76 (1994).

Ballantyne and Nixon, Selective Area Metallization by Electron-Beam Controlled Direct Metallic Deposition, J. Vac. Sci. Technol. 10:1094 (1973).

Barany F., The ligase chain reaction in a PCR WO rld, PCR Methods and Applications 1(1):5-16 (1991).

Barany, F. Genetic disease detection and DNA amplification using cloned thermostable ligase, PNAS 88(1): 189-93 (1991).

Baret et al., Fluorescence-activated droplet sorting (FADS): efficient microfluidic cell sorting based on enzymatic activity, Lab on a Chip 9:1850-1858 (2009).

Baret et al., Kinetic aspects of emulsion stabilization by surfactants: a microfluidic analysis, Langmuir 25:6088-6093 (2009).

Bass et al., Hormone Phage: An Enrichment Method for Variant Proteins With Altered Binding Properties, Proteins 8:309-314(1990).

Bauer, J., Advances in cell separation: recent developments in counterflow centrifugal elutriation and continuous flow cell separation, J Chromatography, 722:55-69 (1999).

Beebe et al., Functional hydrogel structures for autonomous flow control inside microfluidic channels, Nature 404:588-590 (2000).

Beer et al., On-Chip, Real-Time, Single-Copy Polymerase Chain Reaction in Picoliter Droplets, Anal. Chem., 2007, v. 79, pp. 847-8475.

(56) References Cited

OTHER PUBLICATIONS

Bein, Thomas, Efficient Assays for Combinatorial methods for the Discovery of Catalysts, Agnew. Chem. Int. Ed. 38:3, 323-26 (1999).
Benichou et al., Double Emulsions Stabilized by New Molecular Recognition Hybrids of Natural Polymers, Polym. Adv. Tehcnol 13:1019-1031 (2002).
Benner, S.A., Expanding the genetic lexicon: incorporating non-standard amino acids into proteins by ribosome-based synthesis, Trends Biotechnol 12:158-63 (1994).
Benning, M.M. et al., The binding of substrate analogs to phosphotriesterase. J Biol Chem, 275, 30556-30560 (2000).
Berman et al., An agarose gel electrophoresis assay for the detection of DNA-binding activities in yeast cell extracts, Methods Enzymol 155:528-37 (1987).
Bernath et al, In Vitro Compartmentalization by Double Emulsions: Sorting and Gene Enrichment by Fluorescence Activated Cell Sorting, Anal. Biochem 325:151-157 (2004).
Bernath et al., Directed evolution of protein inhibitors of DNA-nucleases by in vitro compartmentalization (IVC) and nano-droplet delivery, J. Mol. Biol 345(5):1015-26 (2005).
Betlach, L. et al., A restriction endonuclease analysis of the bacterial plasmid controlling the EcoRI restriction and modification of DNA. Federation Proceedings, 35, 2037-2043 (1976).
Bibette et al., Emulsions: basic principles, Rep. Prog. Phys. 62: 969-1033 (1999).
Bico, Jose et al., Rise of Liquids and Bubbles in Angular Capillary Tubes, Journal of Colloid and Interface Science, vol. 247, 2002, pp. 162-166.
Bico, Jose et al., Self-Propelling Slugs, J. Fluid Mech., vol. 467, 2002, pp. 101-127.
Blattner and Dahlberg, RNA synthesis startpoints in bacteriophage lambda: are the promoter and operator transcribed?, Nature New Biol 237(77):227-32 (1972).
Boder et al., Yeast surface display for screening combinatorial polypeptide libraries, Nat Biotechnol 15(6):553-7 (1997).
Bougueleret, L. et al., Characterization of the gene coding for the EcoRV restriction and modification system of *Escherichia coli*, Nucleic Acids Res, 12(8):3659-76 (1984).
Boyum, A., Separation of leukocytes from blood and bone marrow. Introduction, Scand J Clin Lab Invest Suppl 97:7 (1968).
Branebjerg et al., Fast mixing by lamination, MEMS Proceedings 9th Ann WO rkshop, San Diego, Feb. 11-15, 1996, 9:441-446 (1996).
Braslaysky et al., Sequence information can be obtained from single DNA molecules, PNAS 100(7):3960-3964 (2003).
Bringer et al., Microfluidic Systems for Chemical Kinetics That Rely on Chaotic Mixing in Droplets, Philos Transact a Math Phys Eng Sci 362:1-18 (2004).
Brody et al., A self-assembled microlensing rotational probe, Applied Physics Letters, 74:144-46 (1999).
Brown et al., Chemical synthesis and cloning of a tyrosine tRNA gene, Methods Enzymol 68:109-151 (1979).
Bru, R. et al., Product inhibition of alpha-chymotrypsin in reverse micelles. Eur J Biochem 199(1): 95-103 (1991).
Bru, R. et al., Catalytic activity of elastase in reverse micelles, Biochem Mol Bio Int, 31(4):685-92 (1993).
Brummelkamp et al., A system for stable expression of short interfering RNAs in mammalian cells, Science 296(5567):550-3 (2002).
Buckpitt et al.,Hepatic and pulmonary microsomal metabolism of naphthalene to glutathione adducts: factors affecting the relative rates of conjugate formation, J. Pharmacol. Exp. Ther. 231:291-300 (1984).
Buican et al., Automated single-cell manipulation and sorting by light trapping, Applied Optics 26(24):5311-5316 (1987).
Burbaum, J., Miniaturization technologies in HTS: how fast, how small, how soon? Drug Discov Today 3:313-322 (1998).
Burns et al., Microfabricated structures for integrated DNA analysis, Proc. Natl. Acad. Sci. USA, May 1996, vol. 93, pp. 5556-5561.
Burns, Mark et al., An Integrated Nanoliter DNA Analysis Device, Science, vol. 282, 1998, pp. 484-487.
Burns, J.R. et al., The Intensification of Rapid Reactions in Multiphase Systems Using Slug Flow in Capillaries, Lab on a Chip, vol. 1, 2001 pp. 10-15.
Byrnes, P.J. et al., Sensitive fluorogenic substrates for the detection of trypsin-like proteases and pancreatic elastase, Anal Biochem, 126:447 (1982).
Cahill et al., Polymerase chain reaction and Q beta replicase amplification, Clin Chem 37(9):1482-5 (1991).
Caldwell, S.R. et al., Limits of diffusion in the hydrolysis of substrates by the phosphodiesterase from Pseudomonas diminuta, Biochemistry, 30: 7438-7444 (1991).
Calvert, P., Inkjet printing for materials and devices, Chem Mater 13: 3299-3305 (2001).
Caruthers, Gene synthesis machines: DNA chemistry and its uses, Science 230:281-285 (1985).
Chakrabarti, A.C. et al., Production of RNA by a polymerase protein encapsulated within phospholipid vesicles, J Mol Evol, 39(6):555-9 (1994).
Chamberlain and Ring, Characterization of T7-specific ribonucleic acid polymerase. 1. General properties of the enzymatic reaction and the template specificity of the enzyme, J Biol Chem 248:2235-44 (1973).
Chan, Emory M. et al., Size-Controlled Growth of CdSe Nanocrystals in Microfluidic Reactors, Nano Letters, vol. 3, No. 2, 2003, pp. 199-201.
Chang, T.M., Recycling of NAD(P) by multienzyme systems immobilized by microencapsulation in artifical cells, Methods Enzymol, 136(67):67-82 (1987).
Chang and Su, Controlled double emulsification utilizing 3D PDMS microchannels, Journal of Micromechanics and Microengineering 18:1-8 (2008).
Chao et al., Control of Concentration and Volume Gradients in Microfluidic Droplet Arrays for Protein Crystallization Screening, 26lh Annual International Conference of the IEEE Engineering in Medicine and Biology Society, San Francisco, California Sep. 1-5, 2004.
Chao et al., Droplet Arrays in Microfluidic Channels for Combinatorial Screening Assays, Hilton Head 2004: A Solid State Sensor, Actuator and Microsystems WO rkshop, Hilton Head Island, South Carolina, Jun. 6-10, 2004.
Chapman et al., In vitro selection of catalytic RNAs, Curr. op. Struct. Biol., 4:618-22 (1994).
Chayen, Crystallization with oils: a new dimension in macromolecular crystal growth Journal of Crystal Growth 196 (1999), pp. 434-441.
Chen et al., Capturing a Photoexcited Molecular Structure Through Time-Domain X-ray Absorption Fine Structure, Science 292(5515):262-264 (2001).
Chen et al., Microfluidic Switch for Embryo and Cell Sorting the 12th International Conference on Solid State Sensors, Actuators, and Microsystems, Boston, MA Jun. 8-12, 2003 Transducers, 1: 659-662 (2003).
Cheng, Z.,et al, Electro flow focusing inmicrofluidic devices, Microluidics Poster, presented at DBAS, Frontiers in Nanoscience, presented Apr. 10, 2003.
Chen-Goodspeed et al., Structural Determinants of the substrate and stereochemical specificity of phosphotriesterase, Biochemistry, 40(5):1325-31 (2001).
Chen-Goodspeed, M. et al., Enhancement, relaxation, and reversal of the stereoselectivity for phosphptriesterase by rational evolution of active site residues, Biochemistry, 40: 1332-1339 (2001b).
Chetverin and Spirin, Replicable RNA vectors: prospects for cell-free gene amplification, expression, and cloning, Prog Nucleic Acid Res Mol Biol, 51:225-70 (1995).
Chiba et al., Controlled protein delivery from biodegradable tyrosino-containing poly(anhydride-co-imide) microspheres, Biomaterials, 18(13): 893-901 (1997).
Chiou et al., A closed-cylce capillary polymerase chain reaction machine, Analytical Chemistry, American Chamical Society, 73:2018-21 (2001).
Chiu et al., Chemical transformations in individual ultrasmall biomimetic containers, Science, 283: 1892-1895 (1999).

(56) References Cited

OTHER PUBLICATIONS

Chou et al., A mirofabricated device for sizing and sorting DNA molecules 96:11-13(1998).
Clackson, T. et al., In vitro selection from protein and peptide libraries, Trends Biotechnol, 12:173-84 (1994).
Clausell-Tormos et al., Droplet-based microfluidic platforms for the encapsulation and screening of Mammalian cells and multicellular organisms, Chem Biol 15(5):427-437 (2008).
Cohen, S. et al., Controlled delivery systems for proteins based on poly(lactic/glycolic acid) microspheres, Pharm Res, 8(6):713-720 (1991).
Collins et al., Optimization of Shear Driven Droplet Generation in a Microluidic Device, ASME International Mechanical Engineering Congress and R&D Expo, Washington (2003).
Collins, J. et al., Microfluidic flow transducer based on the measurements of electrical admittance, Lab on a Chip, 4:7-10 (2004).
Compton, J., Nucleic acid sequence-based amplification, Nature, 350(6313):91-2 (1991).
Cormack, B.P. et al., FACS-optimized mutants of the green fluorescent protein (GFP), Gene 173(1):33-38 (1996).
Cortesi et al., Production of lipospheres as carriers for bioactive compounds, Biomateials, 23(11): 2283-2294 (2002).
Craig, D. et al., Fluorescence-based enzymatic assay by capillary electrophoresis laser-induced fluoresence detection for the determinination of a few alpha-galactosidase molecules, Anal. Biochem. 226: 147 (1995).
Creagh, A.L. et al., Structural and catalytic properties of enzymes in reverse micelles, Enzyme Microb Technol 15(5): 383-92 (1993).
Crosland-Taylor, A Device for Counting Small Particles suspended in a Fluid through a Tube, Nature 171:37-38 (1953).
Crowley, J. M., Electrical breakdown of bimolecular lipid membranes as an electromechanical instability, Biophys J. 13(7):711-724 (1973).
Cull, M.G. et al., Screening for receptor ligands using large libraries of peptides linked to the C terminus of the lac repressor, PNAS 89:1865-9 (1992).
Curran, D.P., Strategy-level separations in organic synthesis: from planning to practice. Angew Chem Int Ed, 37: 1174-11-96 (1998).
Czarnik, A.W., Encoding methods for combinatorial chemistry, Curr Opin Chem Biol 1:60-66 (1997).
Dankwardt et al., Combinatorial synthesis of small-molecule libraries using 3-amino-5-hydroxybenzoic acid, 1:113-120 (1995).
Davis, S.S. et al., Multiple emulsions as targetable delivery systems, Methods in Enzymology, 149: 51-64 (1987).
Davis, J.A. et al., Deterministic hydrodynamics: Taking blood apart, PNAS 103:14779-14784 (2006).
De-Bashan, L. E. et al., Removal of ammonium and phosphorus ions from synthetic wastewater by the microalgae *Chlorella vulgaris* coimmobilized in alginate beads with the microalgae growth-promoting bacterium Azospirillum brasilense, Water Research 36 (2002),pp. 2941-2948.
de Gans, B.J. et al., Inkjet printing of polymers: state of the art and future developments, Advanced materials, 16: 203-213 (2004).
Delagrave, S. et al., Red-shifted excitation mutants of the green fluorescent protein, Biotechnology 13(2):151-4 (1995).
DelRaso, In vitro methodologies for enhanced toxicity testing, Toxicol. Lett. 68:91-99 (1993).
Demartis et al., A strategy for the isolation of catalytic activities from repertoires of enzymes displayed on phage, J. Mol. Biol 286:617-633 (1999).
Dickinson, E., Emulsions and droplet size control, Wedlock, D.J., Ed., in Controlled Particle Droplet and Bubble Formulation, ButterWO rth-Heine-mann, 191-257 (1994).
DiMatteo, et al., Genetic conversion of an SMN2 gene to SMN1: A novel approach to the treatment of spinal muscular atrophy, Exp Cell Res. 314(4):878-886 (2008).
Dinsmore et al., Colioidosomes: Selectively Permeable Capsules Composed of Colloidal Particles, Science 298(5595):1006-1009. (2002).

Dittrich et al., A new embedded process for compartmentalized cell-free protein expression and on-line detection in microfluidic devices, Chembiochem 6(5):811-814 (2005).
Doi, N. and Yanagawa, H. Stable: protein-DNA fusion system for screening of combinatorial protein libraries in vitro, FEBS Lett., 457: 227-230 (1999).
Doi et al., In vitro selection of restriction endonucleases by in vitro compartmentilization, Nucleic Acids Res, 32(12): e95 (2004).
Doman, T.N. et al., Molecular docking and high-throughput screening for novel inhibitors of protein tyrosine phosphatase-1B, J Med Chem, 45: 2213-2221 (2002).
Domling and Ugi, Multicomponent Reactions with Isocyanides, Angew Chem Int Ed 39(18):3168-3210 (2000).
Domling A., Recent advances in isocyanide-based multicomponent chemistry, Curr Opin Chem Biol, 6(3):306-13 (2002).
Dove et al., In Brief, Nature Biotechnology 20:1213 (2002).
Dower et al., High efficiency transformation of *E. coli* by high voltage electroporation, Nucleic Acids Res 16:6127-6145 (1988).
Dressman et al., Transforming single DNA molecules into fluorescent magnetic particles for detection and enumeration of genetic variations, PNAS 100:8817-22 (2003).
Drmanac et al., Sequencing by hybridization: towards an automated sequencing of one million M13 clones arrayed on membranes, Elctrophoresis 13:566-573 (1992).
Dreyfus et al., Ordered and discordered patterns in tw-phase flows in microchannels, Phys Rev Lett 90(14):144505-1-144505-4 (2003).
Dubertret et al., In vivo imaging of quantum dots encapsulated in phospholipid micelles, Science, 298: 1759-1762 (2002).
Duffy et al., Rapid Protyping of Microfluidic Systems and Polydimethylsiloxane, Anal Chem 70:474-480 (1998).
Duggleby, R. G. Enzyme Kinetics and Mechanisms, Pt D. Academic Press 249:61-90 (1995).
Dumas, D.P., Purification and properties of the phosphotriesterase from Psuedomonas diminuta, J Biol Chem 264: 19659-19665 (1989).
Eckert and Kunkel, DNA polymerase fidelity and the polymerase chain reaction, Genome Res 1:17-24 (1991).
Edd et al., Controlled encapsulation of single-cells into monodisperse picolitre drops, Lab Chip 8(8):1262-1264 (2008).
Edel, Joshua B. et al., Microfluidic Routes to the Controlled Production of Nanopaticles, Chemical Communications, 2002 pp. 1136-1137.
Edris et al., Encapsulation of orange oil in a spray dried double emulsion, Nahrung/Food, 45(2):133-137 (2001).
Effenhauser et al., Glass chips for high-speed capillary electrophoresis separations with submicrometer plate heights, Anal Chem 65:2637-2642 (1993).
Eggers, Jens et al., Coalescence of Liquid Drops, J. Fluid Mech., vol. 401, 1999, pp. 293-310.
Ehrig, T. et al., Green-fluorescent protein mutants with altered fluorescence excitation spectra, Febs Lett, 367(2):163-66 (1995).
Eigen, Wie entsteht information? Prinzipien der selbstorganisation in der biologie, Berichte der punsen-gesellschaft fur physikalische chemi, 80:1059-81 (1976).
Eigen et al., hypercycles and compartments: compartments assists-but does not replace-hypercyclic organization of early genetic information, J Theor Biol, 85:407-11 (1980).
Eigen et al., The hypercycle: coupling of RNA and protein biosynthesis in the infection cycle of an RNA bacteriophage, Biochemistry, 30:11005-18 (1991).
Ellington and Szostak, In vitro selection of RNA molecules that bind specific ligands, Nature, 346:818-822 (1990).
Ellman et al., Biosynthetic method for introducing unnatural amino acids site-specifically into proteins, Methods Enzymol, 202:301-36 (1991).
Endo et al., Autocatalytic decomposition of cobalt complexes as an indicator system for the determination of trace amounts of cobalt and effectors, Analyst 121:391-394 (1996).
Endo et al. Kinetic determination of trace cobalt by visual autocatalytic indication, Talanta 47:349-353 (1998).
Eow et al., Electrostatic enhancement of coalescence of water droplets in oil: a review of the technology, Chemical Engineeing Journal 85:357-368 (2002).

(56) References Cited

OTHER PUBLICATIONS

Eow, et al. Electrostatic and hydrodynamic separation of aqueous drops in a flowing viscous oil, Chemical Eng Proc 41:649-657 (2002).
Eow et al., Electrocoalesce-separators for the separation of aqueous drops from a flowing dielectric viscous liquid, Separation and Purification Tech 29:63-77 (2002).
Eow et al., Motion, deformation and break-up of aqueous drops in oils under high electric ?eld strengths, Chemical Eng Proc 42:259-272 (2003).
Eow et al., The behavior of a liquid-liquid interface and drop-interface coalescence under the in?uence of an electric field, Colloids and Surfaces A: Physiochem. Eng. Aspects 215:101-123 (2003).
Faca et al., A mouse to human search for plasma proteome chagnes associated with pancreatic tumor development, PLoS Med 5(6):e123 (2008).
Fahy et al., Self-sustained sequence replication (3SR): an isothermal transcription-based amplification system alternative to PCR, PCR Methods Appl 1:25-33 (1991).
Fan and Harrison, Micromachining of capillary electrophoresis injectors and separators on glass chips and evaluation of flow at capillary intersections, Anal Chem 66:177-184 (1994).
Fastrez, J., In vivo versus in vitro screening or selection for catalytic activity in enzymes and abzymes, Mol Biotechnol 7(1):37-55 (1997).
Fettinger et al., Stacked modules for micro flow systems in chemical analysis: concept and studies using an enlarged model, Sens Actuat B. 17:19-25 (1993).
Fiedler et al., Dielectrophoretic sorting of particles and cells in a microsystem, Anal Chem 70(9):1909-1915 (1998).
Field, J. et al., Purification of a RAS-responsive adenylyl cyclase complex from Saccharomyces cervisiae by use of an epitope addition method. Mol Cell Biol, 8: 2159-2165 (1988).
Fields, S. and Song, O., A novel genetic system to detect protein-protein interactions, Nature 340(6230): 245-6 (1989).
Filella et al., TAG-72, CA 19.9 and CEA as tumor markers in gastric cancer, Acta Oncol. 33(7):747-751 (1994).
Finch, C.A., Industrial Microencapsulation: Polymers for Microcapsule Walls, pp. 1-12 in Encapsulation and Controlled Release, WO odhead Publishing (1993).
Finch, C.A., Encapsulation and controlled release, Spec Publ R Soc Chem, 138:35 (1993).
Fire & Xu, Rolling replication of short DNA circles, PNAS 92(10):4641-5 (1995).
Firestine, S.M. et al., Using an AraC-based three hybrid system to detect biocatalysts in vivo, Nat Biotechnol 18: 544-547 (2000).
Fisch et al., A strategy of exon shuffling for making large peptide repertoires displayed on filamentous bacteriophage, PNAS 93:7761-6 (1996).
Fisher et al., Cell Encapsulation on a Microfluidic Platform, The Eighth International Conference on Miniaturised Systems for Chemistry and Life Scieces, MicroTAS 2004, Sep. 26-30, Malmo, Sweden.
Fletcher et al., Micro reactors: principles and applications in organic synthesis, Tetrahedron 58:4735-4757 (2002).
Fluri et al., Integrated capillary electrophoresis devices with an efficient postcolumn reactor in planar quartz and glass chips, Anal Chem 68:4285-4290 (1996).
Fornusek, L. et al., Polymeric microspheres as diagnostic tools for cell surface marker tracing, Crit Rev Ther Drug Carrier Syst, 2:137-74 (1986).
Fowler, Enhancement of Mixing by Droplet-Based Microfluidics, Int Conf MEMS 97-100 (2002).
Freese, E., The specific mutagenic effect of base analogues on Phage T4, J Mol Biol, 1: 87 (1959).
Frenz et al., Reliable microfluidic on-chip incubation of droplets in delay-lines, Lab on a Chip 9:1344-1348 (2008).
Fu et al., A microfabricated fluorescence-activated cell sorter, Nature Biotechnology, 17(11):1109-1111 (1999).
Fu et al., An Integrated Microfabricated Cell Sorter, Anal. Chem., 74: 2451-2457 (2002).
Fulton et al., Advanced multiplexed analysis with the FlowMetrix system, Clin Chem 43:1749-1756 (1997).
Fulwyler, Electronic Separation of Biological Cells by Volume, Science 150(3698):910-911 (1965).
Gallarate et al., On the stability of ascorbic acid in emulsified systems for topical and cosmetic use, Int J Pharm 188(2):233-241 (1999).
Ganan-Calvo, Generation of Steady Liquid Microthreads and Micron-Sized Monodisperse Sprays and Gas Streams, Phys Rev Lett 80(2):285-288 (1998).
Ganan-Calvo, A.M., Perfectly Monodisperse Microbubbling by Capillary Flow Focusing, Phys Rev Lett 87(27): 274501-1-4 (2001).
Garcia-Ruiz et al., Investigation on protein crystal growth by the gel acupuncture method{, Acta, Cryst., 1994, D50, 99. pp. 484-490.
Garcia-Ruiz et al. A super-saturation wave of protein crystallization, J. Crystal Growth, 2001, v232, pp. 149-155.
Gasperlin et al., The structure elucidation of semisolid w/o emulsion systems containin silicone surfactant, Intl J Pharm, 107:51-6 (1994).
Gasperlin et al., Viscosity prediction of lipophillic semisolid emulsion systems by neural netWO rk modeling, Intl J Pharm, 196:37-50 (2000).
Georgiou et al., Display of heterologous proteins on the surface of microorganisms: from the screenign of combinatiorial libraires to live recombinant vaccines. Nat Biotechnol 15(1), 29-34 (1997).
Georgiou, G., Analysis of large libraries of protein mutants using flow cytometry, Adv Protein Chem, 55: 293-315 (2000).
Gerdts et al., A Synthetic Reaction NetWO rk: Chemical Amplification Using Nonequilibrium Autocatalytic Reactions Coupled in Time, J. Am. Chem. Soc 126:6327-6331 (2004).
Ghadessy et al., Directed Evolution of Polymerase Function by Compartmentalized Self-Replication, PNSAS 98(8): 4552-4557 (2001).
Gibbs et al., Detection of single DNA base differences by competitive oligonucleotide priming, Nucleic Acids Res. 17(7): 2437-48 (1989).
Gilliland, G., Analysis of cytokine mRNA and DNA: Detection and quantitation by competitive polymerase chain reaction, PNAS, 87(7):2725-9 (1990).
Giusti et al., Synthesis and characterization of 5{ fluorescent dye labeled oligonucleotides, Genome Res 2:223-227 (1993).
Gold et al., Diversity of Oligonucleotide Functions Annu Rev Biochem, 64: 763-97 (1995).
Goodall, J. L. et al., Operation of Mixed-Culture Immobilized Cell Reactors for the Metabolism of Meta- and Para-Nitrobenzoate by *Comamonas Sp.* J546 and *Comamonas Sp.* J547, Biotechnology and Bioengineering, vol. 59, No. 1, Jul. 5, 1998, pp. 21-27.
Gordon and Balasubramanian, Solid phase synthesis—designer linkers for combinatorial chemistry: a review, J. Chem. Technol. Biotechnol., 74(9):835-851 (1999).
Grasland-Mongrain et al., Droplet coalescence in microfluidic devices, 30 pages (Jul. 2003) From internet: http://www.eleves.ens.fr/home/grasland/rapports/stage4.pdf.
Green, R. and Szostak, J.W., Selection of a Ribozyme That Functions as a Superior Template in a Sel£ Copying Reaction, Science, 258: 1910-5 (1992).
Gregoriadis, G., Enzyme entrapment in liposomes, Methods Enzymol 44:218-227 (1976).
Griffiths et al., Isolation of high affinity human antibodies directly from large synthetic repertoires, Embo J 13(14):3245-60 (1994).
Griffiths, A.D. et al., Strategies for selection of antibodies by phage display, Curr Opin Biotechnol, 9:102-8 (1998).
Griffiths et al., Man-made enzymes-from design to in vitro compartmentalisation, Curr Opin Biotechnol 11:338-353 (2000).
Griffiths et al., Directed evolution of an extremely fast phosphotriesterase by in vitro compartmentalization, EMBO J, 22:24-35 (2003).
Griffiths, A., and Tawfik, D., Miniaturising the laboratory in emulsion droplets, Trend Biotech 24(9):395-402 (2006).
Guatelli, J.C. et al., Isothermal, in vitro amplification of nucleic acids by a multienzyme reaction modeled after retroviral replication, PNAS, 87(5):1874-8 (1990).
Guixe et al., Ligand-Induced Conformational Transitions in *Escherichia coli* Phosphofructokinase 2: Evidence for an Allosteric Site for MgATP2n, Biochem., 37: 13269-12375 (1998).

(56) References Cited

OTHER PUBLICATIONS

Gupta, K.C., et al., A general method for the synthesis of 3'-sulfhydryl and phosphate group containing oligonucleotides, Nucl Acids Res 19 (11): 3019-3026 (1991).

Haber et al., Activity and spectroscopic properties of bovine liver catalase in sodium bis(2- ethylhexyl) sulfosuccinate/isooctane reverse micelles, Eur J Biochem 217(2): 567-73 (1993).

Habig and Jakoby, Assays for differentiation of glutathione S-transferases, Methods in Enzymology, 77: 398-405 (1981).

Hadd et al., Microchip Device for Performing Enzyme Assays, Anal. Chem 69(17): 3407-3412 (1997).

Haddad et al., A methodology for solving physiologically based pharmacokinetic models without the use of simulation software, Toxicol Lett. 85(2): 113-26 (1996).

Hagar and Spitzer, The effect of endotoxemia on concanavalin A induced alterations in cytoplasmic free calcium in rat spleen cells as determined with Fluo-3, Cell Calcium 13:123-130 (1992).

Hai et al., Investigation on the release of fluorescent markers from the w/o/w emulsions by fluorescenec-activated cell sorter, J Control Release, 96(3): 393-402 (2004).

Haies et al., Morphometric study of rat lung cells. I. Numerical and dimensional characteristics of parenchymal cell population, Am. Rev. Respir. Dis. 123:533-54 (1981).

Hall, Experimental evolution of Ebg enzyme provides clues about the evolution of catalysis and to evolutionary potential, FEMS Microbiol Lett, 174(1):1-8 (1999).

Hall, The EBG system of *E. coli*: origin and evolution of a novel beta-galactosidase for the metabolism of lactose, Genetica 118(2-3):143-56 (2003).

Han et al., Quantum-dot-tagged Microbeads for Multiplexed Optical Coding of Biomolecules, Nat Biotech 19(7): 631-635 (2001).

Handen, J.S., High-throughput screening-challenges for the future, Drug Discov WO rld, 47-50 (2002).

Handique, K. et al., On-Chip Thermopneumatic Pressure for Discrete Drop Pumping, Analytical Chemistry, vol. 73, 2001, pp. 1831-1838.

Hanes et al., In vitro selection and evolution of functional proteins by using ribosome display, PNAS 94:4937-42 (1997).

Hanes et al., Degradation of porous poly(anhydide-co-imide) microspheres and implication for controlled macromolecule deli very, Biomaterials, 19(1-3): 163-172(1998).

Hansen et al., A robust and scalable microfluidic metering method that allows protein crystal growth by free interface diffusion, PNAS 99(26):16531-16536 (2002).

Harada et al., Monoclonal antibody G6K12 specific for membrane-associated differentiation marker of human stratified squamous epithelia and squamous cell carcinoma, J. Oral Pathol. Med 22(4):145-152 (1993).

Harder, K.W. et al., Characterization and kinetic analysis of the intracellular domain of human protein tyrosine phosphatase beta (HPTP beta) using synthetic phosphopeptides, Biochem J 298 (Pt 2): 395-401 (1994).

Harries et al., A Numerical Model for Segmented Flow in a Microreactor, Int J of Heat and Mass Transfer, 46:3313-3322 (2006).

Harris et al., Single-molecule DNA sequencing of a viral genome, Science 320(5872):106-109 (2008).

Harrison et al., Micromachining a miniaturized capillary electrophoresis-based chemical analysis system on a chip, Science 261(5123):895-897 (1993).

Hasina et al., Plasminogen activator inhibitor-2: a molecular biomarker for head and neck cancer progression, Cancer Research 63:555-559 (2003).

Hayward et al., Dewetting Instability during the Formation of Polymersomes from BloceCopolymer-Stabilized Double Emulsions, Langmuir, 22(10): 4457-4461 (2006).

He et al., Selective encapsulation of single cells and subcellular organelles into picoliter- and femtoliter-volume droplets, Anal Chem 77(6):1539-1544 (2005).

Heim et al., Engineering Green Fluorescent Protein for Improved Brightness, Longer Wavelengths and Fluorescence Response Energy Transfer, Carr. Biol, 6(2): 178-182 (1996).

Hellman et al., Differential tissue-specific protein markers of vaginal carcinoma, Br J Cancer, 100(8): 1303-131 (2009).

Hergenrother et al., Small-Molecule Microarrays: Covalent Attachment and Screening of Alcohol-Containing Small Molecules on Glass Slides, J. Am. Chem. Soc, 122: 7849-7850 (2000).

Hildebrand et al., Liquid-Liquid Solubility of Perfluoromethylcyclohexane with Benzene, Carbon Tetrachloride, Chlorobenzene, Chloroform and Toluene, J. Am. Chem. Soc, 71: 22-25 (1949).

Hjelmfelt et al, Pattern-Recognition in Coupled Chemical Kinetic Systems, Science, 260(5106):335-337 (1993).

Ho, S.N. et al., Site-directed mutageneiss by overlap extension using the polymerase chain reaction, Gene, 77(1):51-9 (1989).

Hoang, Physiologically based pharmacokinetic models: mathematical fundamentals and simulation implementations, Toxicol Lett 79(1-3):99-106 (1995).

Hochuli et al., New metal chelate adsorbent selective for proteins and peptides containing neighbouring histidine residues, J Chromatogr 411: 177-84 (1987).

Holmes et al., Reagents for Combinatorial Organic Synthesis: Development of a New O-Nitrobenzyl Photolabile Linder for Solid Phase Synthesis, J. OrgChem., 60: 2318-2319(1995).

Hong, S.B. et al., Stereochemical constraints on the substrate specificity of phosphodiesterase, Biochemistry, 38: 1159-1165 (1999).

Hoogenboom et al., Multi-subunit proteins on the surface of filamentous phage: methodologies for displaying antibody (Fab) heavy and light chains, Nucl Acids Res., 91: 4133-4137 (1991).

Hoogenboom, H.R., Designing and optimizing library selection strategies for generating high-affinity antibodies, Trends Biotechnol, 15:62-70 (1997).

Hopfinger & Lasheras, Explosive Breakup of a Liquid Jet by a Swirling Coaxial Jet, Physics of Fluids 8(7):1696-1700 (1996).

Hopman et al., Rapid synthesis of biotin-, digoxigenin-, trinitrophenyl-, and fluorochrome-labeled tyramides and their application for in situ hybridization using CARD amplification, J of Histochem and Cytochem, 46(6):771-77 (1998).

Horton et al., Engineering hybrid genes without the use of restriction enzymes: gene splicing by overlap extension, Gene 77(1), 61-8 (1989).

Hosokawa, Kazuo et al., Handling of Picoliter Liquid Samples in a Poly(dimethylsiloxane)-Based Microfluidic Device, Analytical Chemistry, vol. 71, No. 20, 1999 pp. 4781-4785.

Hsu et al., Comparison of process parameters for microencapsulation of plasmid DNA in poly(D, L-lactic-co-glycolic acid microspheres, J Drug Target, 7:313-23 (1999).

Huang, Z.J., Kinetic assay of fluorescein mono-beta-D-galactosidase hydrolysis by beta-galactosidase: a front-face measurement for strongly absorbing fluorogenic substrates, Biochemistry, 30:8530-4 (1991).

Huang, Z. et al., A sensitive competitive ELISA for 2,4-dinitrophenol using 3,6-fluorescein diphosphate as a fluorogenic substrate, J Immunol Meth, 149:261 (1992).

Huang L. R. et al., Continuous particle separation through deterministic lateral displacement, Science 304(5673):987-990 (2004).

Hubert et al. Data Concordance from a Comparison between Filter Binding and Fluorescence Polarization Assay Formats for Identification of RUOCK-II Inhibitors, J biomol Screen 8(4):399-409 (2003).

Huebner, A. et al., Quantitative detection of protein expression in single cells using droplet microfluidics, Chem Com 12:1218-1220 (2007).

Hung et al., Optimization of Droplet Generation by controlling PDMS Surface Hydrophobicity, 2004 ASME International Mechanical Engineering Congrees and RD&D Expo, Nov. 13-19, 2004, Anaheim, CA.

Hung, et al, Controlled Droplet Fusion in Microfluidic Devices, MicroTAS 2004, Sep. 26-30, Malmo, Sweden (2004).

Hutchison et al., Cell-free cloning using Phi29 polymerase, PNAS 102(48):17332-17336 (2005).

Ibrahim, S.F. et al., High-speed cell sorting: fundamentals and recent advances, Curr Opin Biotchnol, 14(1):5-12 (2003).

(56) References Cited

OTHER PUBLICATIONS

Ikeda et al., Bioactivation of tegafur to 5-fluorouracil is catalyzed by cytochrome P-450 2A6 in human liver microsomes in vitro, Clin Cancer Res 6(11):4409-4415 (2000).

Inai et al., Immunohistochemical detection of an enamel protein-related epitope in rat bone at an early stage of osteogenesis, Histochemistry 99(5):335-362 (1993).

Ismagilov, Integrated Microfluidic Systems, Angew. Chem. Int. Ed 42:4130-4132 (2003).

Janda, et al, Chemical selection for catalysis in combinatorial antibody libraries, Science, 275:945-948 (1997).

Jang et al., Controllable delivery of non-viral DNA from porous scaffold, J Controlled Release 86(1):157-168 (2003).

Jermutus et al., Recent advances in producing and selecting functional proteins by using cell-free translation, Curr Opin Biotechnol 9(5): 534-48 (1998).

Jestin et al., A Method for the Selection of Catalytic Activity Using Phage Display and Proximity Coupling, Agnew. Chem. Int. Ed. Engi. 38(8):1124-1127 (1999).

Jo, et al, Encapsulation of Bovine Serum Albumin in Temperature-Programmed Shell-in-Shell Structures, Macromol. Rapid Comm 24:957-962 (2003).

Joerger et al., Analyte detection with DNA-labeled antibodies and polymerase chain reaction, Clin. Chem. 41(9):1371-7 (1995).

Johannsson et al., Amplification by Second Enzymes, in ELISA and Other Solid Phase Immunoassays, Kemeny et al (ed.), Chapter 4, pp. 85-106 John Wiley (1988).

Johannsson, A., Heterogeneous Enzyme Immunoassays, in Principles and Practice of Immunoassay, pp. 295-325 Stockton Press (1991).

Johnson, T.O. et al., Protein tyrosine phosphatase 1B inhibitors for diabetes, Nature Review Drug Discovery 1, 696-709 (2002).

Jones, L.J. et al., Quenched BODIPY dye-labeled casein substrates for the assay of protease activity by direct fluorescence measurement, Anal Biochem, 251:144 (1997).

Jones et al. Glowing jellyfish, luminescence and a molecule called coelenterazine, Trends Biotechnol. 17(12):477-81 (1999).

Joo et al., Laboratory evolution of peroxide-mediated cytochrome P450 hydroxylaion, Nature 399:670 (1999).

Joos et al., Covalent attachment of hybridizable oligonucleotides to glass supports, Analytical Biochemistry 247:96-101 (1997).

Joyce, G.F., In vitro Evolution of Nucleic Acids, Curr. Opp. Structural Biol, 4: 331-336 (1994).

Kadir and Moore, Haem binding to horse spleen ferritin, Febs Lett, 276: 81-4 (1990).

Kallen, R.G. et al., The mechanism of the condensation of formaldehyde with tetrahydrofolic acid, J. Biol. Chem., 241:5851-63 (1966).

Kambara et al., Optimization of Parameters in a DNA Sequenator Using Fluorescence Detection, Nature Biotechnology 6:816-821 (1988).

Kamensky et al., Spectrophotometer: new instrument for ultrarapid cell analysis, Science 150(3696):630-631 (1965).

Kanouni et al., Preparation of a stable double emulsion (W1/0/W2): role of the interfacial ilms on the stability of the system, Adv. Collid. Interf. Sci., 99(3): 229-254 (2002).

Katanaev et al., Viral Q beta RNA as a high expression vector for mRNA translation in a cell-free system, Febs Lett, 359:89-92 (1995).

Katsura et al., Indirect micromanipulation of single molecules in water-in-oil emulsion, Electrophoresis, 22:289-93 (2001).

Kawakatsu et al., Regular-sized cell creation in microchannel emulsification by visual microprocessing method, Journal of the American Oil ChemistS Society, 74:317-21 (1997).

Keana J. & Cai, S. X., New reagents for photoaffinity labeling: synthesis and photolysis of functionalized perfluorophenyl azides, J. Org. Chem.55(11):3640-3647 (1990).

Keefe, A.D. et al., Functional proteins from a random-sequence library, Nature, 410: 715-718 (2001).

Keij, J.F., et al., High-speed photodamage cell sorting: an evaluation of the ZAPPER prototype, Methods in cell biology, 42: 371-358 (1994).

Keij et al., High-Speed Photodamage Cell Selection Using a Frequency-Doubled Argon Ion Laser, Cytometry, 19(3): 209-216 (1995).

Kelly et al., Miniaturizing chemistry and biology in microdroplets, Chem Commun 18:1773-1788 (2007).

Kerker, M., Elastic and inelastic light scattering in flow cytometry, Cytometry, 4:1-10 (1983).

Khandjian, UV crosslinking of RNA to nylon membrane enhances hybridization signals, Mol. Bio. Rep. 11: 107-115 (1986).

Kim S. et al, Type II quantum dots: CdTe/CdSe (core/shell) and CdSe/ZnTe (core/shell) heterostructures, J. Am Chem Soc. 125:11466-11467 (2003).

Kim et al., Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125 (2004).

Kircher et al., High-throughput DNA sequencing-concepts and limitations, Bioessays 32(6):524-536 (2010).

Kiss et al., High-throughput quantitative polymerase chain reaction in picoliter droplets, Anal. Chem 80:8975-8981 (2008).

Kitagawa et al., Manipulation of a single cell with microcapillary tubing based on its electrophoretic mobility, Electrophoresis 16:1364-1368 (1995).

Klug and Famulok, All you wanted to know about selex, Molecular Biology Reports, 20:97-107 (1994).

Klug, A., Gene Regulatory Proteins and Their Interaction with DNA, Ann NY Acad Sci, 758: 143-60 (1995).

Klug and Schwabe, Protein motifs 5. Zinc fingers, FASEB J 9(8):597-604 (1995).

Knaak et al., Development of partition coefficients, Vmax and Km values, and allometric relationships, Toxicol Lett. 79(I-3):87-98 (1995).

Knight, James B., Hydrodynamic Focusing on a Silicon Chip: Mixing Nanoliters in Microseconds, Physical Review Lett 80(17):3863-3866 (1998).

Kojima et al. PCR amplification from single DNA molecules on magnetic beads in emulsion: application for high-throughput screening of transcription factor targets. Nucleic Acids Res. 33:e150 (2005).

Kolb et al., Cotranslational folding of proteins, Biochem Cell Biol, 73:1217-20 (1995).

Kopp et al., Chemical amplification: continuous flow PCR on a chip, Science, 280:1046-48 (1998).

Koster et al., Drop-based micro?uidic devices for encapsulation of single cells, Lab on a Chip 8:1110-1115 (2008).

Kowalczykowski et al., Biochemistry of homologous recombination in *Escherichia coli*, Microbiol Rev 58(3):401-65 (1994).

Krafft et al., Emulsions and microemulsions with a ?uorocarbon phase, Colloid and Interface Science 8(3):251-258 (2003).

Krafft et al., Synthesis and preliminary data on the biocompatibility and emulsifying properties of perfluoroalkylated phosphoramidates as injectable surfactants, Eur. J. Med. Chem., 26:545-550 (1991).

Kralj et al., Surfactant-enhanced liquid-liquid extraction in microfluidic channels with inline electric-field enhanced coalescence, Lab Chip 5:531-535 (2005).

Kricka and Wilding, Micromachining: a new direction for clinical analyzers, Pure and Applied Chemistry 68(10):1831-1836 (1996).

Kricka and Wilding, Microchip PCR, Anal Bioanal Chem 377(5):820-825 (2003).

Krumdiek, C.L. et al., Solid-phase synthesis of pteroylpolyglutamates, Methods Enzymol, 524-29 (1980).

Kumar, A. et al., Activity and kinetic characteristics of gltathione reductase in vitro in reverse micellar waterpool, Biochem Biophys Acta, 996(1-2):1-6 (1989).

Lage et al., Whole genome analysis of genetic alterations in small DNA samples using hyperbranched strand displacement amplification and array-CGH. Genome Res. 13: 294-307 (2003).

Lamprecht et al., pH-sensitive microsphere delivery increases oral bioavailability of calcitonin, Journal of Controlled Release, 98(1): 1-9(2004).

(56) References Cited

OTHER PUBLICATIONS

Lancet, D. et al., Probability model for molecular recognition in biuological receptor repertoirs: significance to the olfactory system, PNAS, 90(8):3715-9 (1993).
Landergren et al., A ligase mediated gene detection technique. Science 241(4869):1077-80 (1988).
Lasheras, et al., Breakup and Atomization of a Round Water Jet by a High Speed Annular Air Jet, J Fluid Mechanics 357:351-379 (1998).
Leary et al., Application of Advanced Cytometric and Molecular Technologies to Minimal Residual Disease Monitoring, Proceedings of SPIE 3913:36-44 (2000).
Lee, et al, Preparation of Silica Paticles Encapsulating Retinol Using O/W/O Multiple Emulsions, Journal of Colloid and Interface Science, 240(1): 83-89 (2001).
Lee, et al, Effective Formation of Silicone-in-Fluorocarbon-in-Water Double Emulsions: Studies on Droplet Morphology and Stability, Journal of Dispersion Sci Tech 23(4):491-497(2002).
Lee et al, Investigating the target recognition of DNA cytosine-5 methyltransferase HhaI by library selection using in vitro compartmentalisation (IVC), Nucleic Acids Res 30:4937-4944 (2002).
Lemof, et al, An AC Magnetohydrodynamic Microfluidic Switch for Micro Total Analysis Systems, Biomedical Microdevices, 5(I):55-60 (2003).
Lesley et al., Use of in vitro protein synthesis from PCR-generated templates to study interaction of E coli transcription factors with core RNA polymerase, J Biol Chem 266(4):2632-8 (1991).
Lesley, S.A., Preparation and use of E. coli S-30 extracts, Methods Mol Biol, 37:265-78 (1995).
Leung et al., A method for random mutagenesis of a defined DNA segment using a modified polymerase chain reaction. Technique 1:11-15 (1989).
Li et al., Single-step procedure for labeling DNA strand breaks with lourescein-or BODIPY-conjugated deoxynucleotides: detection of apoptosis and bromodeoxyuridine incorporation. Cytometry 20:172-180 (1995).
Li and Harrison, Transport, Manipulation, and Reaction of Biological Cells On-Chip Using Electrokinetic Effects, Analytical Chemistry 69(8):1564-1568 (1997).
Li et al., Nanoliter microfluidic hybrid method for simultaneous screening and optimization validated with crystallization of membrane proteins, PNAS 103: 19243-19248 (2006).
Liao et al., Isolation of a thermostable enzyme variant by cloning and selection in a thermophile, PNAS 83:576-80 (1986).
Lim et al., Microencapsulated islets as bioartificial endocrine pancreas, Science 210(4472):908-10 (1980).
Link et al, Geometrically Mediated Breakup of Drops in Microfluidic Devices, Phys. Rev. Lett., 92(5): 054503-1 thru 054503-4 (2004).
Link et al., Electric control droplets in microfluidic devices, Angew Chem Int Ed 45:2556-2560 (2006).
Lipinski et al., Experimental and Computational Approaches to Estimate Solubility and Permeability in Drug Discovery and Development Settings,A.:iv. Drug Deliv. Rev., 46:3-26 (2001).
Lipkin et al., Biomarkers of increased susceptibility to gastreointestinal cancer: new application to studies of cancer prevention in human subjects, Cancer Research 48:235-245 (1988).
Liu et al., Passive Mixing in a Three-Dimensional Serpentine MicroChannel, J MEMS 9(2):190-197 (2000).
Liu et al., Fabrication and characterization of hydrogel-based microvalves, Mecoelectromech. Syst.11:45-53 (2002).
Lizardi et al., Mutation detection and single-molecule counting using isothermal rolling-circle amplification. Nat Genet 19(3):225-32 (1998).
Loakes and Brown, 5-Nitroindole as a universal base analogue. Nucleic Acids Res 22: 4039-4043 (1994).
Loakes et al., Stability and structure of DNA oligonucleotides containing non-specific base analogues. J. Mol. Biol 270:426-435 (1997).
Loeker et al., Colloids and Surfaces A: Physicochem. Eng. Aspects 214: 143-150, 2003).

Lopez-Herrera, et al, {the electrospraying of viscous and non-viscous semi-insulating liquids. Scalilng laws,{ Bulletin of the American Physical Society, vol. 40, No. 12, pp. 2041 (1995).
Lopez-Herrera, et al, {One-Dimensional Simulation of the Breakup of Capillary Jets of Conducting Liquids Application to E.H.D. Spraying,{./. Aerosol. Set, vol. 30, No. 7, pp. 895-912 (1999).
Lopez-Herrera, et al, {Coaxial jets generated from electrified Taylor cones. Scaling laws.,{ Aerosol Science, vol. 34, pp. 535-552 (2003).
Lorenceau et al, Generation of Polymerosomes from Double-Emulsions, Langmuir, 21(20): 9183-9186 (2005).
Lorenz et al, Isolation and expression of a cDNA encoding Renilla reniformis luciferase, PNAS 88(10):4438-42 (1991).
Loscertales, et al, Micro/Nano Encapsulation via Electrified Coaxial Liquid Jets, Science, 295(5560): 1695-1698 (2002).
Low N.M. et al., Mimicking somatic hypermutaion: affinity maturation of antibodies displayed on bacteriophage using a bacterila mutator strain. J Mol Biol 260(3), 359-68 (1996).
Lowe, K.C., Perfluorochemical respiratory gas carriers: benefits to cell culture systems, J Fluorine Chem 118:19-26 (2002).
Lowman et al., Selecting high affinity binding proteins by monovalent phage display, Biochemistry 30(45):10832-8 (1991).
Lu et al., Robust fluorescein-doped silica nanoparticles via dense-liquid treatment, Colloids and Surfaces A Physicachemical and Engineering Aspects, 303(3):207-210 (2007).
Luisi et al, Activity and Conformation of Enzymes in Reverse Micellar Solutions, Meth. Enzymol 136:188-216 (1987).
Lund et al., Assesment of methods for covalent binding of nucleic acids to magnetic beads, Dynabeads, and the characteristics of the bound nucleic acids in hybridization reactions, Nucleic Acids Research, Oxford University Press, 16(22) (1998).
Lunderberg et al., Solid-phase technology: magnetic beads to improve nucleic acid detection and analysis, Biotechnology Annual Review, 1:373-401 (1995).
Lundstrom, et al, Breakthrough in cancer therapy: Encapsulation of drugs and viruses, www.currentdrugdiscovery.com, Nov. 19-23, 2002.
Lyne, P.D., Structure-Based Virtual Screening: An Overview, Drug Discov. Today, 7(20):1047-1055 (2002).
Ma, C. et al., In vitro protein engineering using synthetic tRNA(Ala) with different anticodons, Biochemistry 32(31):7939-45 (1993).
Mackenzie et al., The application of flow microfluorimetry to biomedical research and diagnosis: a review, Dev Biol Stand 64:181-193 (1986).
Maclean, D. et al., Glossary of terms used in combinatorial chemistry, Pure Appl. Chem. 71(12):2349-2365 (1999).
Magdassi et al., Multiple Emulsions: HLB Shift Caused by Emulsifier Migration to External Interface, J. Colloid Interface Sci 97:374-379 (1984).
Mahajan et al., Bcl-2 and Bax Interactions in Mitochondria Probed with Green Florescent Protein and Fluorescence Resonance Energy Transfer, Nat. Biotechnol. 16(6): 547-552 (1998).
Manley et al., In vitro transcription: whole cell extract, Methods Enzymol, 101:568-82 (1983).
Manz et al., Micromachining of monocrystalline silicon and glass for chemical analysis systems a look into next century{s technology or just a fashionable craze?, Trends in Analytical Chemistry 10(5):144-149 (1991).
Mao, Q. et al., Substrate effects on the enzymatic activity of alphachymotrypsin in reverse micelles, Biochem Biophys Res Commun, 178(3):1105-12 (1991).
Mao et al., Kinetic behaviour of alpha-chymotrypsin in reverse micelles: a stopped-flow study, Eur J Biochem 208(1):165-70 (1992).
Mardis, E.R., The impact of next-generation sequencing technology on genetics, Trends Genet 24:133-141 (2008).
Margulies, M et al., Genome sequencing in microfabricated high-density picolitre reactors, Nature 437(7057):376-380 (2005).
Marques et al., Porous Flow within Concentric Cylinders, Bull Am Phys Soc Div Fluid Dyn 41:1768 (1996).
Mason, T.J. and Bibette, J. Shear Rupturing of Droplets in Complex Fluids, Langmuir, 13(17):4600-4613 (1997).
Mastrobattista et al., High-throughput screening of enzyme libraries: in vitro evolution of a beta-galactosidase by fluorescence-activated sorting of double emulsions, Chem. Biol. 12(12): 1291-1300 (2005).

(56) References Cited

OTHER PUBLICATIONS

Masui et ai., Probing of DNA-Binding Sites of *Escherichia coli* RecA Protein Utilizing 1-anilinonaphthalene-8-Sulfonic Acid, Biochem 37(35):12133-12143 (1998).

Matayoshi, E.D. et al., Novel fluorogenic substrates for assaying retroviral proteases by resonance energy transfer, Science 247:954 (1990).

Mattheakis et al., An in vitro polysome display system for identifying ligands from very large peptide libraries, PNAS 91:9022-6 (1994).

Mayr, L.M., and Fuerst, P., The Future of High-Throughput Screening, JBiomol Screen 13:443-448 (2008).

Mazutis et al., Droplet-Based Microfluidic Systems for High-Throughput Single DNA Molecule Isothermal Amplification and Analysis, Anal Chem 81(12):4813-4821 (2009).

Mazutis et al., Multi-step microfluidic droplet processing: kinetic analysis of an in vitro translated enzyme, Lab Chip 9:2902-2908 (2009).

McCafferty et al., Phage antibodies: filamentous phage displaying antibody variable domains,Nature, 348: 552-4 (1990).

McDonald et al. Fabrication of microfluidic systems in poly(dimethylsiloxane), Electrophoresis 21(1):27-40 (2000).

McDonald and Whitesides, Poly(dimethylsiloxane) as a material for fabricating microfluidic devices, Account Chem. Res. 35:491-499 (2002).

Melton et al., Efficient in vitro synthesis of biologically active RNA and RNA hybridization probes from plasmids containing a bacteriophage SP6 promoter, Nucl. Acids Res. 12(18):7035-7056 (1984).

Mendel, D. et al., Site-Directed Mutagenesis with an Expanded Genetic Code, Annu Rev Biophys Biomol Struct, 24:435-62 (1995).

Menger and Yamada, Enzyme catalysis in water pools, J. Am. Chem. Soc., 101:6731-4 (1979).

Meylan and Howard, Atom/fragment contribution method for estimating octanol-water partition coefficients, J Pharm Sci. 84(1):83-92 (1995).

Miele et al., Autocatalytic replication of a recombinant RNA, J Mol Biol, 171:281-95 (1983).

Minshuil, J. and Stemmer, W.P., Protein evolution by molecular breeding, Curr Opin Chem Biol 3(3): 284-90 (1999).

Miroux and Walker, Over-production of proteins in *Escherichia coli*: mutant hosts that allow synthesis of some membrane proteins and globular proteins at high levels, J of Mol Biol 260(3):289-98 (1996).

Miyawaki et at., Fluorescent Indicators for Ca2+ Based on Green Fluorescent Proteins and Calmodulin, Nature, 388: 882-887 (1997).

Mize et al., Dual-enzyme cascade—an amplified method for the detection of alkaline phosphatase, Anal Biochem 179(2): 229-35 (1989).

Mock et al., A fluorometric assay for the biotin-avidin interaction based on displacement of the fluorescent probe 2-anilinonaphthalene-6-sulfonic acid, Anal Biochem, 151:178-81 (1985).

Moldavan, A., Photo-electric technique for the counting of microscopical cells, Science 80:188-189 (1934).

Montigiani, S. et al., Alanine substitutions in calmodulin-binding peptides result in unexpected affinity enhancement, J Mol Biol, 258:6-13 (1996).

Moore, M.J., Exploration by lamp light, Nature, 374:766-7 (1995).

Moudrianakis and Beer, Base sequence determination in nucelic acids with the electron microscope 3. Chemistry and microscopy of guanine-labeled DNA, PNAS 53:564-71 (1965).

Mudler et al., Characterization of tWO human monoclonal antibodies reactive with HLA-B12 and HLA-B60, respectively, raised by in vitro secondary immunization of peripheral blood lymphocytes, Hum. Immunol., 36(3):186 192, 1993.

Mulbry, W.W. et al., Parathion hydrolase specified by the Flavobacterium opd gene: relationshio between the gene and protein. J Bacteriol, 171: 6740-6746 (1989).

Nakano et al., Single-molecule reverse transcription polymerase chain reaction using water-in-oil emulsion, J Biosci Bioeng 99:293-295 (2005).

Nakano et al., Single-molecule PCR using water-in-oil emulsion, J Biotech, 102:117-24 (2003).

Nametkin, S.N. et al., Cell-free translation in reversed micelles, FEB Letters, 309(3):330-32.

Narang et al, Improved phosphotriester method for the synthesis of gene fragments, Methods Enzymol, 68:90-98 (1979).

Nelson, P. S., et al., Bifunctional oligonucleotide probes synthesized using a novel CPG support are able to detect single base pair mutations, Nucl Acids Res 17(18): 7187-7194 (1989).

Nemoto et al., In vitro virus: bonding of mRNA bearing puromycin at the 3{-terminal end to the C-terminal end of its encoded protein on the ribosome in vitro, Federation of European Biochemical Societies, 414:405-8 (1997).

Ness, J.E. et al., Molecular Breeding: the natural approach to protein design. Adv Protein Chem, 55: 261-292 (2000).

Ng et al., Protein crystallization by capillary counter-diffusion for applied crystallographic structure determination, J. Struct. Biol. 2003, v142, pp. 218-231.

Ng, B.L. et al., Factors affecting flow karyotype resolution, Cytometry, Part A 69A: 1028-1036 (2006).

Nguyen et al., Optical detection for droplet size control in microfluidic droplet-based analysis systems, Sensors and Actuators B 117(2):431-436 (2006).

Nihant et al., Polylactide Microparticles Prepared by Double Emulsion/Evaporation Technique. I. Effect of Primary Emulsion Stability, Pharmaceutical Research, 11(10):1479-1484 (1994).

Nisisako, Takasi et al., Droplet Formation in a MicroChannel NetWOrk, Lab on a Chip, vol. 2, 2002, pp. 24-26.

Nisisako et al., Formation of droplets using branch channels in a microfluidic circuit, Proceedings of the SICE Annual Conference. International Session Papers 1262-1264 (2002).

Nisisako et al., Controlled formulation of monodisperse double emulsions in a multiple-phase microluidic system, Sot Matter, 1:23-27 (2005).

Nisisako et al., Microstructuerd Devices for Preparing Controlled Multiple Emulsions. Chem. Eng. Technol 31(8):1091-1098 (2008).

Nissim, A. et al., Antibody fragments from a {single pot{ phage display library as immunochemical reagents, Embo J, 13:692-8 (1994).

Nof and Shea, Drug-releasing scaffolds fabricated from drug-loaded microspheres, J. Biomed Mater Res 59:349-356 (2002).

Norman, A., Flow Cytometry, Med. Phys., 7(6):609-615 (1980).

Oberholzer et al., Enzymatic RNA replication in self-reproducing vesicles: an approach to a minimal cell, Biochem Biophys Res Commun 207(1):250-7 (1995).

Oberholzer et al., Polymerase chain reaction in liposomes, Chem. Biol. 2(10):677-82 (1995).

Obukowicz, M.G. et al., Secretion and export of IGF-1 in *Escerichia coli* strain JM101, Mol Gen Genet, 215:19-25 (1988).

Ogura, Y., Catalase activity at high concentrations of hydrogen peroxide, Archs Biochem Biophys, 57: 288-300 (1955).

Oh et al., Distribution of Macropores in Silica Particles Prepared by Using Multiple Emulsions, Journal of Colloid and Interface Science, 254(1): 79-86 (2002).

Okushima et al. Controlled production of monodisperse double emulsions by tWO-step droplet breakup in microfluidic devices, Langmuir 20(23): 9905-8 (2004).

Olsen et ai., Function-based isolation of novel enzymes from a large library, Nat Bioteoltnol 13(10):1071-4 (2000).

Omburo, G.A. et al., Characterization of the zinc binding site of bacterial phosphotriesterase, J of Biological Chem, 267:13278-83 (1992).

Oroskar et al., Detection of immobilized amplicons by ELISA-like techniques, Clin. Chem. 42:1547-1555 (1996).

Ostermeier, M. et al., A combinatorial approach to hybrid enzymes independent of DNA homology, Nat Biotechnol, 17(12):1205-9 (1999).

Ouelette, A new wave of microfluidic devices, Indust Physicist pp. 14-17 (2003).

Pabit et al., Laminar-Flow Fluid Mixer for Fast Fluorescence Kinetics Studies, Biophys J 83:2872-2878 (2002).

Paddison et al., Stable suppression of gene expression by RNAi in mammalian cells, PNAS 99(3):1443-1448 (2002).

(56) References Cited

OTHER PUBLICATIONS

Pannacci et al., Equilibrium and Nonequilibrium States in Microluidic Double Emulsions Physical Review Leters, 101(16):164502 (2008).
Park et al., Cylindrical compact thermal-cycling device for continuous-flow polymeras chain reaction, Anal Chem, ACS, 75:6029-33 (2003).
Park et al., Model of Formation of Monodispersed Colloids, J. Phys. Chem. B 105:11630-11635 (2001).
Parker et al., Development of high throughput screening assays using fluorescence polarization: nuclear receptor-ligand-binding and kinase/phosphatase assays, J Biomol Screen, 5(2): 77-88 (2000).
Parmley et al., Antibody-selectable filamentous fd phage vectors: affinity purification of target genes. Gene 73(2):305-18 (1988).
Pedersen et al., A method for directed evolution and functional cloning of enzymes, PNAS 95(18):10523-8 (1998).
Pelham and Jackson, An efficient mRNA-dependent translation system from reticulocyte lysates, Eur J Biochem 67:247-56 (1976).
Pelletier et al., An in vivo library-versus-library selection of optimized protein-protein interactions, Nature Biotechnology, 17:683-90 (1999).
Peng et al., Controlled Production of Emulsions Using a Crossflow Membrane, Particle & Particle Systems Characterization 15:21-25 (1998).
Perelson et al., Theorectical studies of clonal selection: minimal antibody repertoire size and relaibility of self-non-self discrimination. J Theor Biol 81(4):645-70 (1979).
Perez-Gilabert et al., Application of active-phase plot to the kinetic analysis of lipoxygenase in reverse micelles, Biochemistry J. 288:1011-1015 (1992).
Perrin, J., Polarisation de la lumiere de fluorescence vie moyenne des molecules dans l{etat excite, J. Phys. Rad. 1:390-401 (1926).
Petrounia, I.P. et al., Designed evolution of enzymatic properties, Curr Opin Biotechnol, 11:325-330 (2000).
Piemi et al., Transdermal delivery of glucose through hairless rat skin in vitro: effect of multiple and simple emulsions, Int J Pharm, 171:207-215 (1998).
Pirrung et al., A General Method for the Spatially De?ned Immobilization of Biomolecules on Glass Surfaces Using 'Caged' Biotin, Bioconjug Chem 7: 317-321 (1996).
Ploem, In Fluorescent and Luminescent Probes for Biological Activity Mason, T. G. Ed., Academic Press, Landon, pp. 1-11, 1993.
Pluckthun, A. et al., In vitro selection and evolution of proteins, Adv Protein Chem, 55: 367-403 (2000).
Pollack et al., Electrowetting-based actuation of droplets for integrated microfluidics, Lab Chip 2:96-101 (2002).
Pollack et al., Selective chemical catalysis by an antibody, Science 234(4783):1570-3 (1986).
Pons et al, Synthesis of Near-Infrared-Emitting, Water-Soluble CdTeSe/CdZnS Core/Shell Quantum Dots, Chemistry of Materials 21(8):1418-1424 (2009).
Posner et al., Engineering specificity for folate into dihydrofolate reductase from *Escherichia coli*, Biochemistry, 35: 1653-63 (1996).
Poulin and Theil A priori prediction of tissue: plasma partition coefficients of drugs to facilitate the use of physiologically-based pharmokinetic models in drug discovery, J Pharm Sci 89(1):16-35 (2000).
Priest, et al. Generation of Monodisperse Gel Emulsions in a Microfluidic Device, Applied Physics Letters, 88:024106 (2006).
Qi et al., Acid Beta-Glucosidase: Intrinsic Fluorescence and Conformational Changes Induced by Phospholipids and Saposin C, Biochem., 37(33): 11544-11554 (1998).
Raghuraman et al., Emulston Liquid Membranes for Wastewater Treatment: Equilibrium Models for Some Typical Metal-Extractant Systems,Environ. Sci. Technol 28:1090-1098 (1994).
Ralhan, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173 (2008).
Ramsey, J.M., The burgeoning power of the shrinking laboratory, Nat Biotechnol 17(11):1061-2 (1999).
Ramstrom and Lehn, Drug discovery by dynamic combinatorial libraries, Nat Rev Drug Discov 1:26-36 (2002).
Raushel, F.M. et al., Phosphotriesterase: an enzyme in search of its natural substrate, Adv Enzymol Relat Areas Mol Biol, 74: 51-93 (2000).
Rech et al., Introduction of a yeast artificial chromosome vector into Sarrachomyeces cervesia by electroporation, Nucleic Acids Res 18:1313 (1990).
Reyes et al., Micro Total Analysis Systems. 1. Introduction, Theory and Technology, Anal Chem 74(12):2623-2636 (2002).
Riess, J.S., Fluorous micro- and nanophases with a biomedical perspective, Tetrahedron 58(20):4113-4131 (2002).
Roach et al., Controlling nonspeci?c protein adsorption in a plug-based micro?uidic system by controlling inteifacial chemistry using ?uorous-phase surfactants, Anal. Chem. 77:785-796 (2005).
Roberts, J.W.,Termination factor for RNA synthesis, Nature, 224: 1168-74 (1969).
Roberts et al., Simian virus 40 DNA directs synthesis of authentic viral polypeptides in a linked transcription-translation cell-free system 72(5):1922-1926 (1975).
Roberts, et al., RNA-peptide fusion for the in vitro selection of peptides and proteins, PNAS 94:12297-302 (1997).
Roberts, R.W. Totally in vitro protein selection using mRNA-protein fusions and ribosome display. Curr Opin Chem Biol 3(3), 268-73 (1999).
Roberts & Ja, In vitro selection of nucleic acids and proteins: What are we learning?, Curr Opin Struct Biol 9(4): 521-9 (1999).
Rodriguez-Antona et al., Quantitative RT-PCR measurement of human cytochrome P-450s: application to drug induction studies. Arch. Biochem. Biophys., 376:109-116 (2000).
Rolland et al., Fluorescence Polarization Assay by Flow Cytometry, J. Immunol. Meth., 76(1): 1-10 (1985).
Rosenberg et al.,Termination of transcription in bacteriophage lambda, J Biol Chem, 250: 4755-64 (1975).
Rosenberry, T.L., Acetylcholinesterase, Adv Enzymol Relat Areas Mol Biol, 43: 103-218 (1975).
Rotman, Measurement of activities of single molecules of beta-galactosidase, PNAS, 47:1981-91 (1961).
Russon et al., Single-nucleotide polymorphism analysis by allele-specific extension of fluorescently labeled nucleotides in a microfluidic flow-through device, Electrophoresis, 24:158-61 (2003).
Sadtler et al., Achieving stable, reverse water-in-fluorocarbon emulsions. Angew Chem Int Ed 35:1976-1978 (1996).
Saiki, R.K, et al, Primer directed enzymatic amplification of DNA with a thermostable DNA polymerase. Science 239(4839):487-91 (1988).
Sanchez et al., Breakup of Charged Capillary Jets, Bulletin of the American Physical Society Division of Fluid Dynamics 41:1768-1768 (1996).
Sano, T. et al., Immuno-PCR-Very sensitive antigen-detection by means of sepcific antibody-DNA conjugates. Science 258(5079), 120-122 (1992).
SantaLucia, A unified view of polymer, dumbbell, and oligonucleotide DNA nearest-neighbor thermodynamics, PNAS 95(4):1460-5 (1998).
Santra et al., Fluorescence lifetime measurements to determine the core-shell nanostructure of FITC-doped silica nanoparticles: An optical approach to evaluate nanoparticle photostability, J Luminescence 117(1):75-82 (2006).
Schatz et al., Screening of peptide libraries linked to lac repressor, Methods Enzymol 267: 171-91 (1996).
Schneegass et al., Miniaturized flow-through PCR with different template types in a silicone chip thermocycler, Lab on a Chip, Royal Soc of Chem, 1:42-9 (2001).
Schubert et al., Designer Capsules, Nat Med 8:1362 (2002).
Schweitzer et al., Immunoassays with rolling circle DNA amplification: A versatile platform for ultrasensitive antigen detection, PNAS 97(18), 10113-10119 (2000).
Schweitzer, B. et al., Combining nucleic acid amplification and detection. Curr Opin Biotechnol 12(1):21-7 (2001).

(56) References Cited

OTHER PUBLICATIONS

Scott, R.L., The Solubility of Fluorocarbons, J. Am. Chem. Soc, 70: 4090-4093 (1948).
Seethala and Menzel, Homogeneous, Fluorescence Polarization Assay for Src-Family Tyrosine Kinases, Anal Biochem 253(2):210-218 (1997).
Seiler et al., Planar glass chips for capillary electrophoresis: repetitive sample injection, quantitation, and separation efficiency, Anal Chem 65(10):1481-1488 (1993).
Selwyn M. J., A simple test for inactivation of an enzyme during assay, Biochim Biophys Acta 105:193-195 (1965).
Seo et al., Microfluidic consecutive flow-focusing droplet generators, Soft Matter, 3:986-992 (2007).
Seong et al., Fabrication of Microchambers Defined by Photopolymerized Hydrogels and Weirs Within Microfluidic Systems: Application to DNA Hybridization, Analytical Chem 74(14):3372-3377 (2002).
Seong and Crooks, Efficient Mixing and Reactions Within Microfluidic Channels Using Microbead-Supported Catalysts, J Am Chem Soc 124(45):13360-1 (2002).
Sepp et al., Microbead display by in vitro compartmentalisation: selection for binding using flow cytometry, FEBS Letters 532:455-58 (2002).
Serpersu et al., Reversible and irreversible modification of erythrocyte membrane permeability by electric field, Biochim Biophys Acta 812(3):779-785 (1985).
Shapiro, H.M., Multistation multiparameter flow cytometry: a critical review and rationale, Cytometry 3: 227-243 (1983).
Shestopalov et al., Multi-Step Synthesis of Nanoparticles Performed on Millisecond Time Scale in a Microfluidic Droplet-Based System, The Royal Society of Chemistry 4:316-321, 2004.
Shtern V, and Hussain F., Hysteresis in swirling jets, J. Fluid Mech. 309:1-44 (1996).
Sia &Whitesides, Micro?uidic devices fabricated in poly(dimethylsiloxane) for biological studies, Electrophoresis 24(21):3563-3576 (2003).
Sidhu, S.S., Phage display in pharmaceutical biotechnology, Curr Opin Biotech 11:610-616 (2000).
Siemering et al., Mutations that suppress the thermosensitivity of green fluorescent protein, Current Biology 6:1653-1663 (1996).
Silva-Cunha et al., W/O/W multiple emulsions of insulin containing a protease inhibitor and an absorption enhancer: biological activity after oral administration to normal and diabetic rats, Int J Pharm 169:33-44 (1998).
Sims et al., Immunopolymerase chain reaction using real-time polymerase chain reaction for detection, Anal. Biochem. 281(2):230-2 (2000).
Slappendel et al., Normal cations and abnormal membrane lipids in the red blood cells of dogs with familial stomatocytosis hypertrophic gastritis, Blood 84:904-909 (1994).
Slob et al., Structural identifiability of PBPK models: practical consequences for modeling strategies and study designs, Crit Rev Toxicol. 27(3):261-72 (1997).
Smith et al., The synthesis of oligonucleotides containing an aliphatic amino group at the 5{ terminus: synthesis of fluorescent DNA primers for use in DNA sequence analysis, Nucl. Acid Res. 13:2399-2412 (1985).
Smith G.P., Filamentous fusion phage: novel expression vectors that display cloned antigens on the virion surface, Science 228(4705):1315-7(1985).
Smith et al., Fluorescence detection in automated DNA sequence analysis, Nature 321:674-679 (1986).
Smith et al., Direct mechanical measurements of the elasticity of single DNA molecules by using magnetic beads, Science 258(5085):1122-1126 (1992).
Smith et al., Phage display, Chemical Reviews 97(2), 391-410 (1997).
Smyth et al., Markers of apoptosis: methods for elucidating the mechanism of apoptotic cell death from the nervous system, Biotechniques 32:648-665 (2000).
Sohn, et al, Capacitance cytometry: Measuring biological cells one by one, PNAS 97(20):10687-10690 (2000).
Somasundaram and Ramalingam, Gain studies of Rhodamine 6G dye doped polymer laser, J Photochem Photobiol 125(1-3):93-98 (1999).
Song, H. and Ismagilov, R.F., Millisecond kinetics on a microluidic chip using nanoliters of reagents, J Am Chem Soc. 125: 14613-14619 (2003).
Song et al., A microfluidic system for controlling reaction netWO rks in time, Angew. Chem. Int. Ed. 42(7):768-772 (2003).
Song et al., Experimental Test of Scaling of Mixing by Chaotic Advection in Droplets Moving Through Microfluidic Channels, App Phy Lett 83(22):4664-4666 (2003).
Soni and Meller, Progress toward ultrafast DNA sequencing using solid-state nanopores, Clin Chem 53:1996-2001 (2007).
Soumillion et al., Selection of B-lactomase on filamentous bacteriophage by catalytic activity, J Mol Biol, 237:415-22 (1994).
Soumillion et al., Novel concepts for the selection of catalytic activity. Curr Opin Biotechnol 12:387-394 (2001).
Sproat et al., The synthesis of protected 5'-mercapto-2',5'-dideoxyribonucleoside-3'-0- phosphorainidites, uses of 5'-mercapto-oligodeoxyribonucleotides, Nucleic Acids Res 15:4837-4848 (1987).
Stauber, et a., Rapid generation of monoclonal antibody-secreting hybridomas against African horse sickness virus by in vitro immunization and the fusion/cloning technique, J. Immunol. Meth 161(2):157-168 (1993).
Stemmer, W.P., DNA shuffling by random fragmentation and reassembly: in vitro recombination for molecular evolution. PNAS 91(22):10747-51(1994).
Stemmer, W.P., Rapid evolution of a protein in vitro by DNA shuffling, Nature 370(6488):389-91 (1994).
Stober et al., Controlled growth of monodisperse silica spheres in the micron size range, J Colloid and Interface Sci 26(1):62-69 (1968).
Stofko, H.R. et al., A single step purification for recombinant proteins. Characterization of microtube associated protein (MAP2) fragment which associates with the type II cAMP-dependent protein kinase, Febs Lett 302: 274-278 (1992).
Strizhkov et al., PCR amplification on a microarray of gel-immobilized oligonucleotides: Detection of bacterial toxin- and drug-resistant genes and their mutations, BioTechniques 29(4):844-857 (2000).
Stroock et al., Chaotic mixer for microchannels, Science 295(5555):647-651 (2002).
Studer et al., Fluorous Synthesis: A Fluorous-Phase Strategy for Improving Separation Efficiency in Organic Synthesis, Science 275: 823-826 (1997).
Sugiura et al., Effect of Channel Structure on MicroChannel Emuisification, Langmuir 18:5708-5712 (2002).
Sugiura et al., Interfacial tension driven monodispersed droplet formation from mtcrofabricated channel array Langmuir, 17: 5562-5566 (2001).
Sundberg et al., Spatially-Addressable Immobilisation of Macromolecules on Solid Supports, J. Am. Chem. Soc, 117:12050-12057 (1995).
Suzuki et al., Random mutagenesis of thermus aquaticus DNA polmerase I: concordance of immutable sites in vivo with the crystal structure, PNAS USA, 93:96701-9675 (1996).
Szostak, J.W., In vitro selection of functional nucleic acids. Ann. Rev. Biochem. 68, 611-647 (1999).
Takayama et al., Patterning Cells and Their Environments Using Multiple Laminar Fluid Flows in Capillary NetWO rks, PNAS 96:5545-5548 (1999).
Takeuchi et al., An Axisymmetric Flow-Focusing Microfluidic Device, Adv. Mater 17(8):1067-1072 (2005).
Tan, Y.C., Monodisperse Droplet Emulsions in Co-Flow Microfluidic Channels, Micro TAS, Lake Tahoe (2003).
Tan, Y.C., Microfluidic Liposome Generation from Monodisperse Droplet Emulsion-Towards the Realization of Artificial Cells, Summer Bioengineering Conference, Florida (2003).
Tan et al., Controlled Fission of Droplet Emulsions in Bifurcating Microfluidic Channels, Transducers Boston (2003).
Tan et al., Design of microluidic channel geometries for the control of droplet volume, chemical concentration, and sorting, Lab Chip, 4(4): 292-298 (2004).

(56) References Cited

OTHER PUBLICATIONS

Tan et al., Monodispersed micro?uidic droplet generation by shear focusing micro?uidic device, Sensors and Actuators 114:350-356 (2006).
Tanaka et al., Ethanol Production from Starch by a Coimmobilized Mixed Culture System of *Aspergillus awamori* and *Zymomonas mobilis*, Biotechnol Bioeng XXVII:1761-1768 (1986).
Tang et al., A multi-color fast-switching microfluidic droplet dye laser, Lab Chip 9:2767-2771 (2009).
Taniguchi et al., Chemical Reactions in Microdroplets by Electrostatic Manipulation of Droplets in Liquid Media, Lab on a Chip 2:19-23 (2002).
Tawfik et al., catELISA: a facile general route to catalytic antibodies, PNAS 90(2):373-7 (1993).
Tawfik, D.S. et al., 1,8-diabycyclo[5.4.0]undecane mediated transesterification of p-nitrophenyl phosphonates—a novel route to phosphono esters, Synthesis-Stuttgart, 10: 968-972 (1993).
Tawfik et al., Efficient and selective p-nitrophenyl-ester=hydrolyzing antibodies elicited by a p-nitrobenzyl phosphonate hapten, Eur J Biochem, 244:619-26 (1997).
Tawfik et al., Man-made cell-like compartments for molecular evolution, Nature Biotechnology, 7(16):652-56 (1998).
Taylor et al., Characterization of chemisorbed monolayers by surface potential measurments, J. Phys. D. Appl. Phys. 24:1443 (1991).
Tchagang et al., Early detection of ovarian cancer using group biomarkers, Mol Cancer Ther 7:27-37 (2008).
Tencza et al., Development of a Fluorescence Polarization-Based Diagnostic Assay for Equine Infectious Anemia Virus, J Clinical Microbiol 38(5):1854-185 (2000).
Terray, et al, Fabrication of linear colloidal structures for microfluidic applications, Applied Phys Lett 81(9):1555-1557 (2002).
Terray et al., Microluidic Control Using Colloidal Devices,Science, 296(5574):1841-1844 (2002).
Tewhey et al., Microdroplet-based PCR amplification for large scale targeted sequencing, Nat Biotechnol 27(11):1025-1031 (2009).
Thompson, L.F., Introduction to Lithography, ACS Symposium Series 219:1-13, (1983).
Thorsen et al., Dynamic pattern formation in a vesicle-generating microfluidic device, Phys Rev Lett 86(18):4163-4166 (2001).
Thorsen et al., Microfluidic Large-Scale Integration, Science 298:580-584 (2002).
Tice et al., Formation of droplets and mixing in multiphase microfluidics at low values of the reynolds and the capillary numbers, Langmuir 19:9127-9133 (2003).
Tice et al., Effects of viscosity on droplet formation and mixing in microfluidic channels, Analytica Chimica Acta 507:73-77 (2004).
Titomanlio et al., Capillary experiments of flow induced crystallization of HOPE{, AlChe Journal, 1990, v36, No. 1, pp. 13-18.
Tleugabulova et al., Evaluating formation and growth mechanisms of silica particles using fluorescence anisotropy decay analysis, Langmuir 20(14):5924-5932 (2004).
Tokatlidis et al., Nascent chains: folding and chaperone intraction during elongation on ribosomes, Philos Trans R Soc Lond B Biol Sci, 348:89-95 (1995).
Tokeshi et al., Continuous-Flow Chemical Processing on a Microchip by Combining Microunit Operations and a Multiphase Flow NetWO rk, Anal Chem 74(7):1565-1571 (2002).
Tokumitsu, H. et al., Preparation of gadopentetic acid-loaded chitosan microparticles for gadolinium neutron-capture therapy of cancer by a novel emulsion-droplet coalescence technique, Chem and Pharm Bull 47(6):838-842 (1999).
Tramontano, A., Catalytic antibodies, Science 234(4783):1566-70 (1986).
Trindade, T., Nanocrystalline semiconductors: synthesis, properties, and perspectives, Chem. Mat. 13:3843-3858 (2001).
Tripet, B. et al., Engineering a de novo-designed coiled-coil heterodimerization domain off the rapid detection, purification and characterization of recombinantly expressed peptides and proteins, Protein Engng., 9:1029-42 (1996).
Tuerk, C. and Gold, L., Systematic Evolution of Ligands by Exponentid Enrichment: RNA Ligands to Bacteriophage T4 DNA Polymerase, Science, 249:505-10 (1990).
Umbanhowar et al., Monodisperse Emulsion Generation via Drop Break Off in a Coflowing Stream, Langmuir 16(2):347-351 (2000).
Unger et al., Monolithic microfabricated valves and pumps by multylayer soft lithography, Science 288(5463):113-116 (2000).
Utada, A. et al., Monodisperse double emulsions generated from a microcapillary device, Science, 308:537-541 (2005).
Vainshtein et al., Peptide rescue of an N-terminal truncation of the stoffel fragment of Taq DNA polymerase, Protein Science, 5:1785-92 (1996).
Van Bockstaele et al., Prognostic markers in chronic lymphocytic leukemia: a comprehensive review, Blood Rev 23(1):25-47 (2009).
Van Dilla et al., The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105, distributed Jan. 23, 1968.
Van Dilla et al., Cell Microfluorometry: A Method for Rapid Fluorescence Measurement, Science 163(3872):1213-1214 (1969).
Vanhooke et al., Three-dimensional structure of the zinc-containing phosphotrieesterase with the bound substrate analog diethy 4-methylbenzylphosphonate, Biochemistry 35:6020-6025 (1996).
Varga, J.M. et al., Mechanism of allergic cross-reactions-I. Multispecific binding of ligands to a mouse monoclonal anti-DNP IgE antibody. Mol Immunol 28(6), 641-54 (1991).
Vary, A homogeneous nucleic acid hybridization assay based on strand displacement, Nucl Acids Res 15(17):6883-6897 (1987).
Venkateswaran et al., Production of Anti-Fibroblast Growth Factor Receptor Monoclonal Antibodies by in Vitro Immunization, Hybirdoma, 11(6):729-739 (1992).
Venter et al., The sequence of the human genome, Science 291(5507):1304-51 (2001).
Vogelstein et al., Digital PCR, PNAS 96(16):9236-9241 (1999).
Voss, E.W., Kinetic measurements of molecular interactions by spectrofluorometry, J Mol Recognit, 6:51-58 (1993).
Wahler, D. et al., Novel methods for biocatalyst screening. Curr Opin Chem Biol, 5: 152-158 (2001).
Walde, P. et al., Structure and activity of trypsin in reverse micelles, Eur J Biochem, 173(2):401-9 (1988).
Walde, P. et al., Spectroscopic and kinetic studies of lipases solubilized in reverse micelles, Biochemistry, 32(15):4029-34 (1993).
Walker et al., Strand displacement amplification—an isothermal, in vitro DNA amplification technique, Nucleic Acid Res, 20(7):1691-6 (1992).
Walker et al., Isothermal in vitro amplification of DNA by a restriction enzyme/DNA polymerase system, PNAS 89(1):392-6 (1992).
Wang, A.M. et al., Quantitation of mRNA by the polymerase chain reaction. Proc natl Acad Sci USA 86(24), 9717-21 (1989).
Wang, G.T. et al., Design and synthesis of new fluorogenic HIV protease substrates based on resonance energy transfer, Tetrahedron Lett., 31:6493 (1990).
Wang et al., Preparation of Titania Particles Utilizing the Insoluble Phase Interface in a MicroChannel Reactor, Chemical Communications 14:1462-1463 (2002).
Wang et al., DEP actuated nanoliter droplet dispensing using feedback control, Lab on a Chip 9:901-909 (2008).
Warburton, B., Microcapsules for Multiple Emulsions, Encapsulation and Controlled Release, Spec Publ R Soc Chem, 35-51 (1993).
Weil. et al., Selective and accurate initiation of transcription at the Ad2 major late promotor in a soluble system dependent on purified RNA polymerase II and DNA, Cell, 18(2):469-84 (1979).
Wetmur et al., Molecular haplotyping by linking emulsion PCR: analysis of paraoxonase 1 haplotypes and phenotypes, Nucleic Acids Res 33(8):2615-2619 (2005).
Wick et al., Enzyme-containing liposomes can endogenously produce membrane-constituting lipids, Chem Biol 3(4):277-85 (1996).
Widersten and Mannervik, Glutathione Transferases with Novel Active Sites Isolated by Phage Display from a Library of Random Mutants, J Mol Biol 250(2):115-22 (1995).

(56) References Cited

OTHER PUBLICATIONS

Wiggins et al., Foundations of chaotic mixing, Philos Transact a Math Phys Eng Sci 362(1818):937-70 (2004).
Williams et al., Methotrexate, a high-affinity pseudosubstrate of dihydrofolate reductase, Biochemistry, 18(12):2567-73 (1979).
Williams et al., Amplification of complex gene libraries by emulsion PCR, Nature Methods 3(7):545-550 (2006).
Wilson, D.S. and Szostak, J.W., In vitro selection of functional nucleic acids, Ann. Rev. Biochem. 68: 611-647 (1999).
Winter et al., Making antibodies by phage display technology, Annu Rev Immunol 12:433-55 (1994).
Wittrup, K.D., Protein engineering by cell-surface display. Curr Opin Biotechnology, 12: 395-399 (2001).
Wolff et al., Integrating advanced functionality in a microfabricated high-throughput fluorescent-activated cell sorter, Lab Chip, 3(1): 22-27 (2003).
Wronski et al., Two-color, fluorescence-based microplate assay for apoptosis detection. Biotechniques, 32:666-668 (2002).
Wu et al., The ligation amplification reaction (LAR)—amplification of specific DNA sequences using sequential rounds of template-dependent ligation, Genomics 4(4):560-9 (1989).
Wyatt et al., Synthesis and purification of large amounts of RNA oligonucleotides, Biotechniques 11(6):764-9 (1991).
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xu, S. et al., Generation of monodisperse particles by using microfluidics: control over size, shape, and composition, Angew. Chem. Int. Ed. 44:724-728 (2005).
Yamagishi, J. et al., Mutational analysis of structure-activity relationships in human tumor necrosis factor-alpha, Protein Eng, 3:713-9 (1990).
Yamaguchi et al., Insulin-loaded biodegradable PLGA microcapsules: initial burst release controlled by hydrophilic additives, Journal of Controlled Release, 81(3): 235-249 (2002).
Komatsu et al., Roles of cytochromes P450 1A2, 2A6, and 2C8 in 5-fluorouracil formation rom tegafur, an anticancer prodrug, in human liver microsomes. Drug Met. Disp., 28:1457-1463 (2001).
Yershov et al., DNA analysis and diagnostics on oligonucleotide microchips, PNAS 93(10):4913-4918 (1996).
Yonezawa et al., DNA display for in vitro selection of diverse peptide libraries, Nucleic Acids Research, 31(19): e118 (2203).
Yu et al., Specific inhibition of PCR by Non-Extendable Oligonucleotides Using a 5' to 3' Exonuclease-Defcient DNA Polymerase, Biotechniques 23(4):714-6, 718-20 (1997).
Yu et al. Responsive biomimetic hydrogel valve for microfluidics. Appl. Phys. Lett 78:2589-2591 (2001).
Yu et al., Quantum dot and silica nanoparticle doped polymer optical fibers, Optics Express 15(16):9989-9994 (2007).
Zaccolo, M. et al., An approach to random mutagenesis of DNA using mixtures of triphosphate derivatives of nucleoside analogues. J Mol Biol 255(4):589-603 (1996).
Zakrzewski, S.F., Preparation of tritiated dihydrofolic acid of high specific activity, Methods Enzymol, 539 (1980).
Zaug and Cech, The Tetrahymena intervening sequence ribonucleic acid enzyme is a phosphotransferase and an acid phosphatase, Biochemistry 25(16):4478-82 (1986).
Zaug et al., The Tetrahymena ribozyme acts like an RNA restriction endonuclease, Nature 324(6096):429-33 (1986).
Zaug and Cech, The intervening sequence RNA of Tetrahymena is an enzyme, Science 231(4737):470-5 (1986).
Zhang, Z.Y., Substrate specificity of the protein tyrosine phosphatases, PNAS 90: 4446-4450 (1993).
Zhang et al., A Simple Statistical Parameter for Use in Evaluation and Validation of High Throughput Screening Assays, Journal of Biomolecular Screening, 4(2): 67-73 (1999).
Zhao, H. et al., Molecular evolution by staggered extension process (StEP) in vitro recombination. Nat Biotechnol 16(3):258-61 (1998).
Zhao, B. et al., Control and Applications of Immiscible Liquids in Microchannels, J. Am. Chem. Soc, vol. 124:5284-5285 (2002).
Zheng et al., Screening of Protein Crystallization Conditions on a Microfluidic Chip Using Nanoliter-Size Droplets, J Am Chem Soc 125(37):11170-11171 (2003).
Zheng et al., Formation of Droplets of Alternating Composition in Microfluidic Channels and Applications to Indexing of Concentrations in Droplet-Based /Assays, Anal. Chem., 2004, v. 76, pp. 4977-4982.
Zheng et al., A Droplet-Based, Composite PDMS/Glass Capillary Microfluidic System for Evaluating Protein Crystallization Conditions by Microbatch and Vapor-Diffusion Methods with On-Chip X-Ray Diffraction, Angew. Chem., pp. 1-4, 2004.
Zheng et al., A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17): 2520-2523 (2005).
Zimmermann et al., Dielectric Breakdown of Cell Membranes, Biophys J 14(11):881-889 (1974).
Zimmermann et al., Microscale Production of Hybridomas by Hypo-Osmolar Electrofusion, Hum. Antibod. Hybridomas, 3(1): 14-18 (1992).
Zubay, G., In vitro synthesis of protein in microbial systems, Annu Rev Genet, 7: 267-87 (1973).
Zubay, G., The isolation and properties of CAP, the catabolite gene activator, Methods Enzymol, 65: 856-77 (1980).
Zuckermann, R. et al., Efficient Methods for Attachment of Thiol-Specific Probes to the 3{-end of Synthetic Oligodeoxyribonucleotides, Nucleic Acids Res. 15:5305-5321 (1987).

* cited by examiner

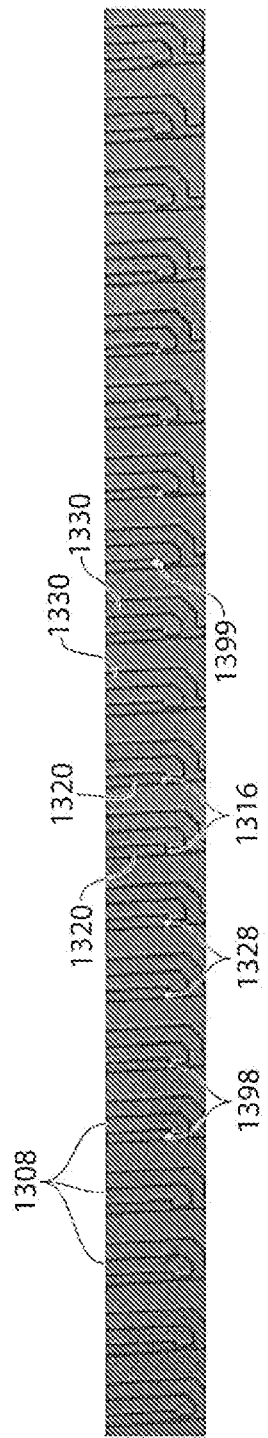
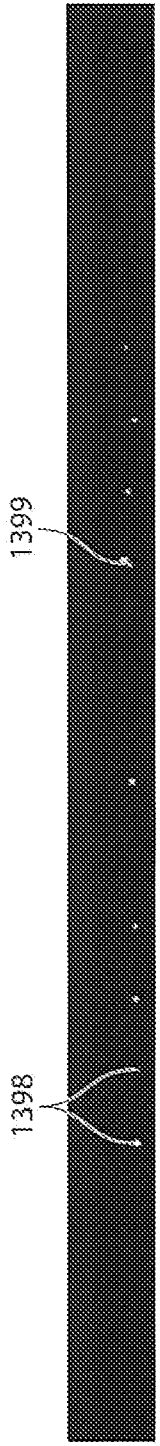
Fig. 13A
Fig. 13B

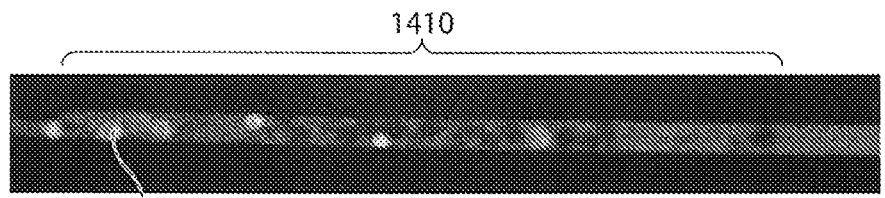
1498    Fig. 16A
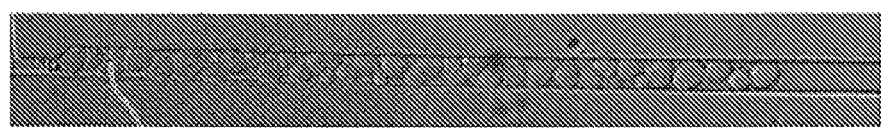
1498    Fig. 16B
1498    Fig. 16C

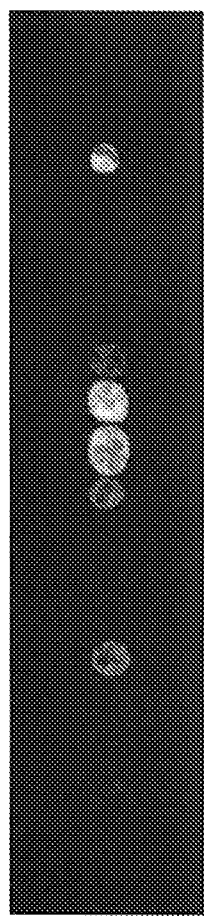 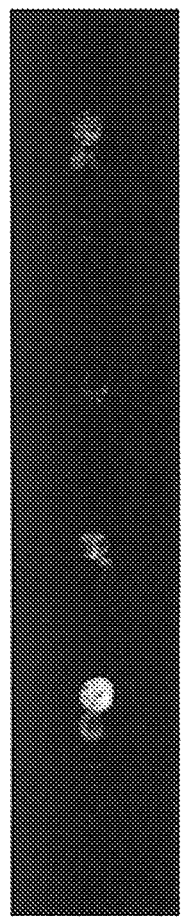
Fig. 24A                    Fig. 24B

MANIPULATION OF FLUIDS, FLUID COMPONENTS AND REACTIONS IN MICROFLUIDIC SYSTEMS

RELATED APPLICATIONS

This application is a U.S. National Stage Filing under 35 U.S.C. §371 of PCT/US2008/005009, filed Apr. 18, 2008, which claims priority to U.S. Provisional Patent Application No. 60/925,357, filed Apr. 19, 2007.

GOVERNMENT SUPPORT

This invention was made with government support under 5 R21 GM075052-02S1 awarded by the National Institutes of Health (Department of Health and Human Services). The government has certain rights in the invention.

FIELD OF INVENTION

The present invention relates generally to microfluidic structures, and more specifically, to microfluidic structures and methods for manipulating fluids, fluid components, and reactions.

BACKGROUND

Microfluidic systems typically involve control of fluid flow through one or more microchannels. One class of systems includes microfluidic "chips" that include very small fluid channels and small reaction/analysis chambers. These systems can be used for analyzing very small amounts of samples and reagents and can control liquid and gas samples on a small scale. Microfluidic chips have found use in both research and production, and are currently used for applications such as genetic analysis, chemical diagnostics, drug screening, and environmental monitoring. Although these systems may allow manipulation of small volumes of fluids, additional methods that allow further control and flexibility are needed.

SUMMARY OF THE INVENTION

Microfluidic structures and methods for manipulating fluids, fluid components, and reactions are provided.

In one aspect of the invention, a method is provided. The method comprises providing a microfluidic network comprising a first region and a microfluidic channel in fluid communication with the first region, flowing a first fluid in a first direction in the microfluidic channel, and flowing a second fluid in the first direction in the microfluidic channel. The method also includes partitioning at least a portion of the first fluid at the first region, at least in part through action of the second fluid, so as to form a first droplet of the first fluid at the first region. The method also includes maintaining the droplet at the first region while the second fluid is flowing in the first direction.

In another embodiment, a method comprises providing a microfluidic network comprising at least a first inlet to a microfluidic channel, a first and a second region for forming a first and a second droplet, respectively, the first and second regions in fluid communication with the microfluidic channel, and flowing a first fluid in the microfluidic channel. The method involves partitioning a first portion of the first fluid at the first region, at least in part through action of the second fluid, so as to form the first droplet at the first region, and partitioning a second portion of the first fluid at the second region, at least in part through action of the second fluid, so as to form the second droplet at the second region.

In another embodiment, a microfluidic device comprises a plurality of chamber units positioned in parallel, each chamber unit comprising: a chamber having a chamber inlet and a chamber outlet, a feed channel fluidly connected to a plurality of chamber inlets, a drain channel fluidly connected to a plurality of chamber outlets, a chamber bypass channel extending from the chamber, and a fluid restriction region between the chamber outlet and the drain channel, the fluid restriction region being more restrictive to fluid flow than the chamber.

In another embodiment, a method comprises flowing a fluid containing a plurality of components in a microfluidic system comprising a chamber having a flow direction, a chamber inlet, a chamber outlet, and a chamber bypass channel extending from the chamber between the chamber inlet and the chamber outlet. The method also includes positioning a component in the chamber, the chamber having a cross-sectional area, perpendicular to the flow direction, less than 2 times the largest cross-sectional area of the component perpendicular to the flow direction, and flowing a fluid through the chamber while maintaining the component at its position in the chamber. A portion of the plurality of components may be flowed in the chamber bypass channel.

In another embodiment, a system comprises a microfluidic device comprising an inlet, an outlet, a chamber having a flow direction, and a flow restriction region fluidly connected to the outlet of the chamber, and a plurality of cells generally aligned in the chamber. At least 80% of the cells have a largest cross-sectional area, perpendicular to the flow direction, of between 0.1 and 1.0 times the cross-sectional area of the chamber perpendicular to the flow direction. The flow restriction region is constructed and arranged to allow a fluid but not the cells to pass therethrough.

A method may also comprise providing a microfluidic network comprising at least a first inlet to a microfluidic channel, a first and a second region for positioning a first and a second reactive component, respectively, the first and second regions in fluid communication with the microfluidic channel, wherein the first region is closer in distance to the first inlet than the second region, and flowing a first fluid comprising first and second components in the microfluidic channel. The method may also include positioning the first component at the first region, positioning the second component at the second region, and maintaining the first and second components in the first and second regions, respectively, while a fluid is flowing in the microfluidic channel. In one embodiment, the first and/or second reactive component is a cell. In another embodiment, the first and/or second reactive component is a bead. In some cases, positioning of the first and/or second reactive components does not require use of a fluid immiscible with the first fluid. The method may optionally include flowing a second fluid comprising an associating component in the microfluidic channel, wherein the associating component can interact with the first and/or second reactive components. The associating component may be a binding partner complementary to the first and/or second components. In some embodiments, the microfluidic channel comprises an upstream portion, a downstream portion, and first and second fluid paths extending from the upstream portion and reconnecting at the downstream portion. The first and second fluid paths may have different resistances to flow. In some cases, the first region is positioned within the first fluid path.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 13A-13B show an array of single cells positioned in chambers of a microfluidic system according to one embodiment of the invention.

FIGS. 16A-16C show fluorescently-labeled cells at a region of a microfluidic device according to one embodiment of the invention.

FIGS. 24A-24E show different levels of gene expression in cells that are exposed to various buffers according to one embodiment of the invention.

DETAILED DESCRIPTION

Figure 1A:
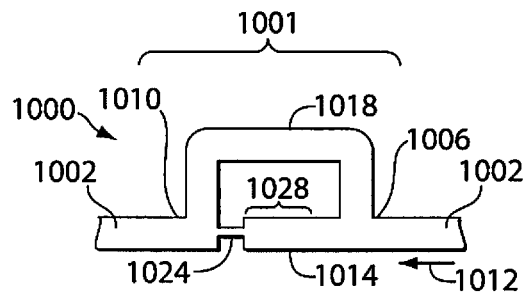
FIGS. 1A-1E show schematically a microfluidic network for positioning a droplet in a region of the network according to one embodiment of the invention.

The present invention relates to microfluidic structures and methods for manipulating fluids, fluid components, and reactions. In one aspect, such structures and methods involve positioning fluid samples, e.g., in the form of droplets, in a carrier fluid (e.g., an oil, which may be immiscible with the fluid sample) in predetermined regions in a microfluidic network. In some embodiments, positioning of the droplets can take place in the order in which they are introduced into the microfluidic network (e.g., sequentially) without significant physical contact between the droplets. Because of the little or no contact between the droplets, coalescence between the droplets can be avoided. Accordingly, in such embodiments, surfactants are not required in either the fluid sample or the carrier fluid to prevent coalescence of the droplets. Positioning of droplets without the use of surfactants is desirable in certain cases where surfactants may negatively interfere with the contents in the fluid sample (e.g., proteins). Structures and methods described herein also enable droplets to be removed sequentially from the predetermined regions to a different region of the fluidic network where they can be further processed.

Once the droplets are positioned at the predetermined regions, they can be stored and/or may undergo manipulation (e.g., diffusion, evaporation, dilution, and precipitation). In some instances, many (e.g., 1000) droplets can be manipulated, sometimes simultaneously. Manipulation of fluid samples can be useful for a variety of applications, including testing for reaction conditions, e.g., in crystallization, and chemical and/or biological assays, including chemical reactions, enzymatic reactions, immuno-based reactions (e.g., antigen-antibody), and cell-based reactions.

It should be understood that while several of the embodiments described herein refer to the positioning and/or manipulation of droplets, the embodiments are also applicable to other components such as cells and beads, which may be contained in a fluid without being in a droplet.

In another aspect, microfluidic structures and methods described herein can allow production of droplets of a precise volume, which can be stored/maintained at precise regions of the device. The droplets can be created at a region (e.g., a storage region) in a self-regulated manner. The method may include, optionally, filling a microfluidic channel with a filling fluid (e.g., oil). The oil can then be flushed out with a first fluid (e.g., an aqueous fluid) to be stored/maintained at a region of the device. This first fluid may be immiscible with the filling fluid. The first fluid can enter a region of the device for storing a droplet, replacing the filling fluid in that region. Next, a second fluid (e.g., a fluid immiscible with the first fluid) may be flowed in the channel, causing partitioning of a portion of the first fluid. Partitioning of the first fluid causes formation of a droplet of the first fluid at the region, while a second portion of the first fluid bypasses the region. In this manner, a plurality of droplets can be generated sequentially down the length of the channel.

In another aspect, microfluidic structures and methods described herein are designed for containing and positioning components in an arrangement such that the components can be manipulated and then tracked even after manipulation. For example, cells may be constrained in an arrangement in microfluidic structures described herein to facilitate tracking during their growth and/or after they multiply. This can allow, for example: 1) cells to be trapped and observed over time; 2) culturing of cells in a manner than allows determination of their identity and lineage; and 3) manipulation of the cells (e.g., by staining or washing) while maintaining the identity and/or position of the cells. Other advantages and applications are described in more detail below.

Certain microfluidic chips described herein may include a microfluidic network having a region for forming droplets of sample in a carrier fluid (e.g., an oil), and one or more regions (e.g., microreactor regions, microwells, reservoirs, chambers, or portions of a microfluidic channel) in which the droplets can be positioned and reaction conditions within the droplet can be varied. In some embodiments, the droplet formation region is the same as the region in which the droplet is positioned for varying a condition within the droplet. Droplets may be positioned sequentially in regions of the microfluidic network so that upon manipulating and/or performing a chemical and/or biological process within each the droplets, the droplets can be identified at a later time, for example, to determine the particular conditions within the droplets that lead to a favorable outcome (e.g., optimal conditions for forming a product, for crystal growth, etc.).

As used herein, "droplet" means a small portion of a fluid, isolated from other portions of the same fluid. A droplet can have a traditional, rounded shape, or a different shape which can be influenced by its environment. A droplet of a first fluid can be surrounded by different, immiscible fluid, or bounded by a surface of an article, or a gas such as air, or a combination. For example, a droplet of a first fluid can be suspended in (completely surrounded by) a second fluid immiscible with the first fluid. Or a droplet of a first fluid can reside on a surface of a solid article, with portions that are not in contact with the surface exposed to the second fluid or a gas. A droplet can be bounded on multiple sides by one or more surfaces of an article, e.g. the interior of a channel. For example, a portion of a channel completely filled with a first fluid, which resides within a discrete regions of the channel, is a droplet for purposes of the invention.

It should also be understood that any suitable fluid(s) can be used in connection with devices and methods described herein. Where embodiments describe the use of "immiscible" fluids, those of ordinary skill in the art know or can determine by simple experimentation which combination of fluids is immiscible. For instance, solubility parameters of a variety of fluids are available in literature and can be used to determine miscibility/immiscibility. Additionally and/or alternatively, simple experimentation may include, for example, mixing two or more fluids in a container—if the fluids partition after a certain period of time, the fluids are immiscible. Furthermore, it should be understood that where "first" and "second" fluids are described herein, these fluids can have any suitable composition and can be interchangeable in other embodiments. For example, one particular embodiment may describe the use of a "first fluid" that is aqueous and a "second fluid" that is an oil, and a different embodiment may described a "first fluid" as an oil and a "second fluid" that is aqueous. In certain embodiments, first and second fluids can be miscible with one another (e.g., both being aqueous or both being an oil). Gaseous fluids may also be used.

FIG. 1 shows a method for positioning a droplet in a region of a microfluidic network according to one embodiment of the invention. As shown in illustrative embodiment of FIG. 1A, microfluidic network 1000 comprises section 1001 including microfluidic channel 1002 having an upstream portion 1006 and a downstream portion 1010 (as fluid flows in the direction of arrow 1012), with fluid path 1014 and fluid path 1018 (e.g., a bypass channel)extending from the upstream portion and reconnecting at the downstream portion. In some cases, resistance to fluid flow (hydrodynamic resistance) may differ between fluid paths 1014 and 1018. For example, fluid path 1014 may have less resistance to fluid flowing in the direction of arrow 1012 prior to positioning of a droplet in this section of the microfluidic network. As shown in this illustrative embodiment, fluid path 1014 has a lower resistance to fluid flow than fluid path 1018 due to the relatively longer channel length of fluid path 1018. It should be understood, however, that the microfluidic network may have other designs and/or configurations for imparting different relative resistances to fluid flow, and such designs and configurations can be determined by those of ordinary skill in the art. For instance, in some embodiments, the length, width, height, and/or shape of the fluid path can be designed to cause one fluid path to have a resistance to fluid flow different from another fluid path. In other embodiments, at least a portion of a fluid path may include an obstruction such as a valve (which may change hydrodynamic resistance dynamically), a semi-permeable plug (e.g., a hydrogel), a membrane, or another structure that can impart and/or change resistance to fluid flow through that portion.

Figure 1B:
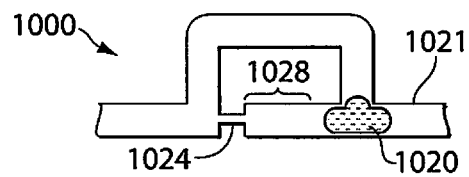
Figure 1C:
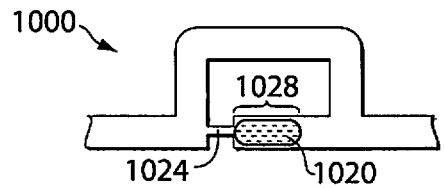

As shown in FIGS. 1B and 1C, droplet 1020 flows in the direction of 1012, e.g., by being carried by a carrier fluid 1021 flowing in the same direction. Upon passing the junction between flow paths 1014 and 1018 at upstream portion 1006, the droplet flows in fluid path 1014 due to its lower resistance to flow in that fluid path relative to fluid path 1018. However, as fluid path 1014 includes a fluid restriction region 1024 (e.g., a "narrow fluid path portion" and/or a region having a smaller cross-sectional area than that of fluid path portion 1014), droplet 1020 cannot flow further down the microfluidic network. Accordingly, droplet 1020 is positioned within a region 1028 (e.g., a "microwell" or "chamber") of the microfluidic network. In some embodiments, droplet 1020 can be maintained at the region even though carrier fluid continues to flow in the microfluidic network (e.g., in the direction of arrow 1012). It should be understood that any suitable fluid path can be used as a fluid restriction region, which may have a higher hydrodynamic resistance and/or a smaller cross-sectional area for fluid flow than a region immediately upstream or downstream of the fluid constriction region. For instance, fluid restriction region 1024 may be in the form of a narrow fluid path or a channel having the same dimensions as fluid path 1014, but having an obstruction (e.g., posts or a valve) positioned in or at the region. In other embodiments, fluid restriction region 1024 may comprise a porous membrane, a semi-permeable plug (e.g., a gel), a valve, or another structure.

Figure 1D:
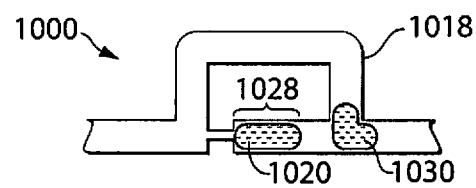
Figure 1E:
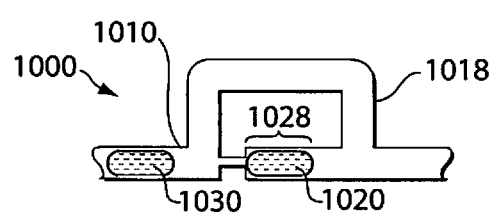

As shown in the embodiment illustrated in FIG. 1D, the positioning of droplet 1020 at region 1028 causes fluid path 1014 to be plugged such that no or minimal fluid flows past fluid restriction region 1024. This plugging of fluid path 1014 causes a higher resistance to fluid flow in that path compared to that of fluid path 1018. As a result, when a second droplet 1030 flows in the direction of arrow 1012, the second droplet bypasses flow path 1014 and enters flow path 1018, which now has a lower hydrodynamic resistance than that of fluid path 1014 (FIG. 1D). Accordingly, second droplet 1030 can bypass first droplet 1020 and can now be positioned in a second region within microfluidic network 1000 (not shown).

It should be understood that when droplet 1020 is positioned at region 1028, the droplet may plug all or a portion of fluid path 1014 and/or fluid restriction region 1024. For instance, in some cases, the droplet plugs all of such fluid paths such that none of carrier fluid 1021 (or another fluid) flowing in microfluidic channel 1002 passes through fluid restriction region 1024. In other embodiments, the droplet may plug only a portion of such fluid paths such that some fluid passes through fluid restriction region 1024 even though the droplet is positioned at region 1028. The amount of fluid flowing past the positioned droplet may depend on factors such as the dimensions of fluid path portions 1014 and/or 1024, the size of the droplets, the flow rate, etc. As the droplet causes fluid path 1014 to have a higher relative hydrodynamic resistance than fluid path 1018, a second droplet can bypass fluid path 1014 and enter fluid path 1018. As described above, fluid paths 1014 and 1018 may have different hydrodynamic resistances depending on whether or not a droplet is positioned at region 1028. In the absence of a droplet positioned at region 1028, fluid path 1014 may be configured to have a lower hydrodynamic resistance than fluid path 1018. For example, greater than 50%, greater than 60%, greater than 70%, greater than 80%, or greater than 90% of the fluid flowing in channel 1002 at upstream portion 1006 may flow in fluid path 1014 compared to fluid path 1018. However, when the droplet is positioned and maintained in region 1028, fluid path 1014 may be relatively more restrictive to fluid flow. For example, less than 50%, less than 40%, less than 30%, less than 20%, or less than 10% of the fluid flowing in channel 1002 at upstream portion 1006 may flow in fluid path 1014 compared to that of 1018. In some cases, 100% of the fluid flowing in direction 1012 in microfluidic channel 1002 flows in fluid path 1018 upon positioning of a droplet in region 1028.

As illustrated in the exemplary embodiment of FIG. 1, the positioning of droplet 1020 (e.g., a first droplet) and the subsequent bypass of droplet 1030 (e.g., a second droplet) does not require contact between the first and second droplets due to the design of section 1001. In certain embodiments, the second droplet does not physically contact the first droplet after positioning of the first droplet in region 1028. This can occur, in some embodiments, when the volume and/or length of fluid path 1014 (between fluid restriction region 1024 and the intersection between fluid paths 1014 and 118) is larger than the volume and/or length of droplet 1020. In other embodiments, the second droplet can come into physical contact with the first droplet as it bypasses the first droplet, however, due to such minimal contact between the two droplets, the droplets do not coalesce. This can occur, in some embodiments, when the volume and/or length of fluid path 1014 (between fluid restriction region 1024 and the intersection between fluid paths 1014 and 118) is smaller than the volume and/or length of droplet 1020.

Accordingly, in some instances, the positioning of the droplets in the microfluidic network can take place without the use of surfactants. In other words, surfactants in either a fluid flowing in channel 1002 (e.g., a carrier fluid) or within the droplets is not required in order to stabilize the droplets and/or prevent the droplets from coalescing with one another during positioning or carrying the droplet in the microfluidic channel, and/or during maintaining the droplets within a predetermined region within the microfluidic network. However, in instances where coalescence is desired (e.g., to allow a reaction between reagents contained in two droplets), the microfluidic network and methods for operating the network can be configured to allow such physical contact and/or coalescence between droplets. These interactions or absence of interactions can be controlled, for example, by varying the volume and/or length of the droplets, as well as the volume and/or length of regions 1028. In some embodiments, methods for positioning a droplet in a microfluidic network include the steps of providing a microfluidic network comprising a first region (e.g., region 1028 of FIG. 1A) and a microfluidic channel in fluid communication with the first region, flowing a first fluid (e.g., a carrier fluid) in the microfluidic channel, and flowing a first droplet comprising a second fluid (e.g., a fluid sample) in the microfluidic channel, wherein the first fluid and the second fluid are immiscible. The first droplet may be positioned in the first region and maintained in the first region while the first fluid is flowing in the microfluidic channel. In such embodiments, positioning and/or maintaining the first droplet in the first region does not require the use of a surfactant in the first or second fluids. As described in more detail below, other components such as cells and beads may be positioned in addition to or instead of droplets in a similar manner.

In some embodiments, a chemical and/or biological process and/or another manipulation process can be carried out in droplet 1020 of FIG. 1 while the droplet is positioned in region 1028. For example, a fluid sample in the droplet may undergo a process such as diffusion, evaporation, dilution, and/or precipitation. The droplet may be manipulation, for example, by changing the concentration of the fluid flowing in channel 1002 after the droplet has been positioned at region 1028. In other embodiments, region 1028 is in fluid communication with another fluidic channel, flow path, reservoir, or other structure, e.g., via a semi permeable membrane that may be positioned adjacent the region (e.g., underneath or above region 1028), and manipulation of the droplet can occur via such passages. Manipulations of fluids are described in more detail in U.S. application Ser. No. 60/925, 357, filed Apr. 19, 2007, and entitled "Manipulation of Fluids and Reactions in Microfluidic Systems", which is incorporated herein by reference in its entirety for all purposes.

Figure 2A:
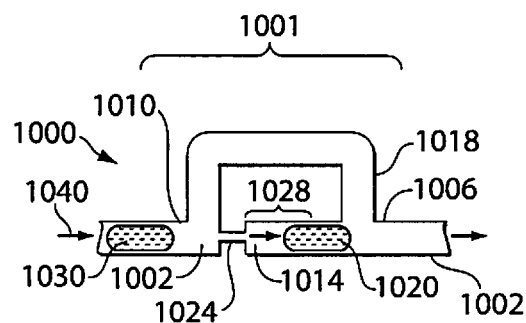
FIGS. 2A-2C show schematically removal of a droplet from a region of the network according to one embodiment of the invention.
Figure 2B:
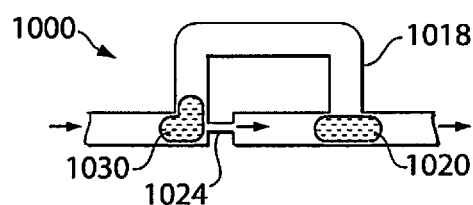
Figure 2C:
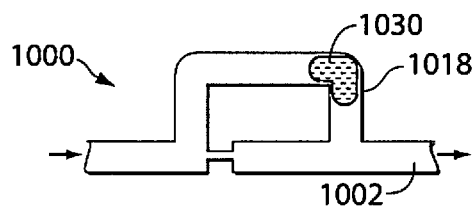

In some embodiments, droplets that have been positioned at regions of a microfluidic network can be removed or extracted from the regions to a different location in the microfluidic network, where they can be optionally processed, manipulated, and/or collected. As shown in the illustrative embodiments of FIGS. 2A-2C, removing droplet 1020 from region 1028 of section 1001 of microfluidic network 1000 can take place by reversing the flow of the carrier fluid in the network such that the carrier fluid now flows in the direction of arrow 1040 (instead of in the direction of arrow 1012 of FIGS. 1A-1E).

In some such embodiments, upstream portion 1006 and downstream portion 1010 of FIGS. 1A-1E now become reversed such that portion 1010 is now an upstream portion and portion 1006 is now a downstream portion. The flow of a carrier fluid in the direction of arrow 1040 in microfluidic channel 1002 causes a portion of the fluid to flow through fluid restriction region 1024 into region 1028 where droplet 1020 is positioned. This fluid flow causes the droplet to flow in the direction of arrow 1040. As shown in the embodiment illustrated in FIG. 2B, droplet 1030, which may have been positioned at a different region of the microfluidic network, can be removed from that region and may also flow in the direction of arrow 1040. As droplet 1030 encounters fluid restriction region 1024, the droplet cannot flow through this narrow opening due to the region's high hydrodynamic resistance. As a result, the droplet bypasses fluid restriction region 1024 and flows into fluid path 1018 until it reaches microfluidic channel 1002 at downstream portion 1006. Thus, by reversing the flow and the pressure gradient in the microfluidic network, droplets 1020 and 1030 can be removed sequentially from the regions of the microfluidic network where they previously resided. That is, droplet 1020, which was positioned first before droplet 1030, can be removed from its region and can enter a different region of the microfluidic network before that of droplet 1020. Optionally, when droplet 1030 reaches downstream portion 1006, the flow can be reversed again (e.g., such that fluid flows in the direction of arrow 1012 of FIGS. 1A-1E) to cause droplet 1030 to enter into region 1028. This method can allow droplets to be removed from a first region and positioned in a second region of the microfluidic network.

In some embodiments, sequential positioning of droplets can be performed such that a first droplet is positioned in a first region before a second droplet is positioned in a second region (and, optionally, before third, fourth, fifth droplets, etc. are positioned in their respective regions). As described above, sequential removal of the droplets can be performed such that the first droplet is removed from a region and/or positioned at a different location of the microfluidic network before the second droplet (and, optionally, before third, fourth, fifth droplets, etc. are removed from their respective regions). In other embodiments, removal of the droplets can be performed such that the second droplet is removed and/or positioned at a different location of the microfluidic network before the first droplet.

In some cases, several (e.g., greater than 2, greater than 5, greater than 10, greater than 50, greater than 100, greater than 200, greater than 500, or greater than 1000) droplets can be positioned at regions of the microfluidic network, wherein the droplets are positioned in the regions in the order the droplets are introduced into the microfluidic network. In some cases, removing several droplets positioned at regions of the microfluidic network comprises removing the droplets in the order the droplets were introduced into the microfluidic network (or in the order the droplets were positioned into the regions of the microfluidic network). In other cases, removing several droplets positioned at regions of the microfluidic network comprises removing the droplets in the reverse order the droplets were introduced into the microfluidic network (or in the reverse order the droplets were positioned into the regions of the microfluidic network). Other methods of positioning and removal of droplets are also possible.

The sequential (or predetermined/known order of) removal of droplets from regions of a microfluidic network can allow control over the identification and location of each droplet within the network. This can also allow determination of the contents inside each of the droplets from the time they are formed and/or introduced into the microfluidic network, to the time the droplets are manipulated and/or extracted from the microfluidic network.

Figure 3:
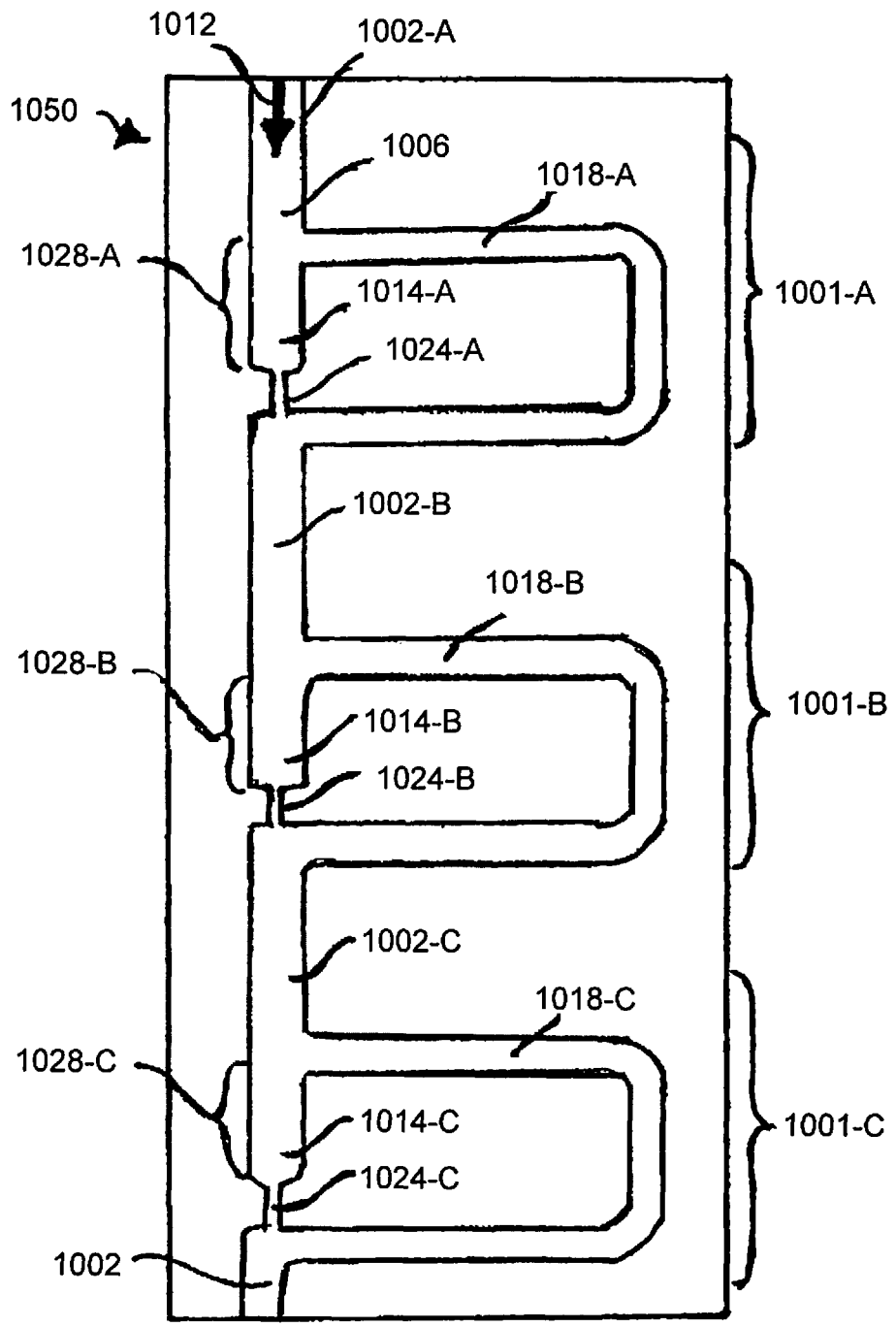
FIG. 3 is a photograph showing multiple sections of a microfluidic network for positioning droplets according to one embodiment of the invention.

FIG. 3 is a photograph of multiple sections 1001-A, 1001-B, and 1001-C of microfluidic network 1050 according to one embodiment of the invention. A carrier fluid may flow in microfluidic channel 1002-A in the direction of arrow 1012 from an inlet positioned upstream of portion 1006. The carrier fluid may partition at the junction where fluid paths 1014-A and 1018-A extend from microfluidic channel 1002. The proportion of fluid that flows in each of the fluid paths can be determined at least in part by the relative hydrodynamic resistances of the paths, as described above. In the embodiment shown in FIG. 3, sections 1001-A, 1001-B, and 1001-C are positioned in series. In other embodiments, however, such sections may be positioned in parallel and/or in both series and parallel. Other configurations are also possible.

A microfluidic network may have any suitable number of microfluidic sections 1001. For instance, the microfluidic network may have greater than or equal to 5, greater than or equal to 10, greater than or equal to 30, greater than or equal to 70, greater than or equal to 100, greater than or equal to 200, greater than or equal to 500, or greater than or equal to 1000 such sections.

In additional, although certain embodiments herein show that sections 1001 can allow positioning of a single droplet in each of the sections, in other embodiments, the sections can be designed such that greater than one droplet (e.g., greater than or equal to 2, greater than or equal to 5, or greater than or equal to 10 droplets) can be positioned at each section.

Furthermore, although only two fluid flow paths 1014 and 1018 are shown extending from channel 1002, in other embodiments, more than two (e.g., greater than or equal to 3, greater than or equal to 5, or greater than or equal to 10) fluid paths may extend from channel 1002. Each extending fluid path may optionally comprise one or more regions (e.g., microwells) for positioning and/or maintaining droplets.

Figure 4:
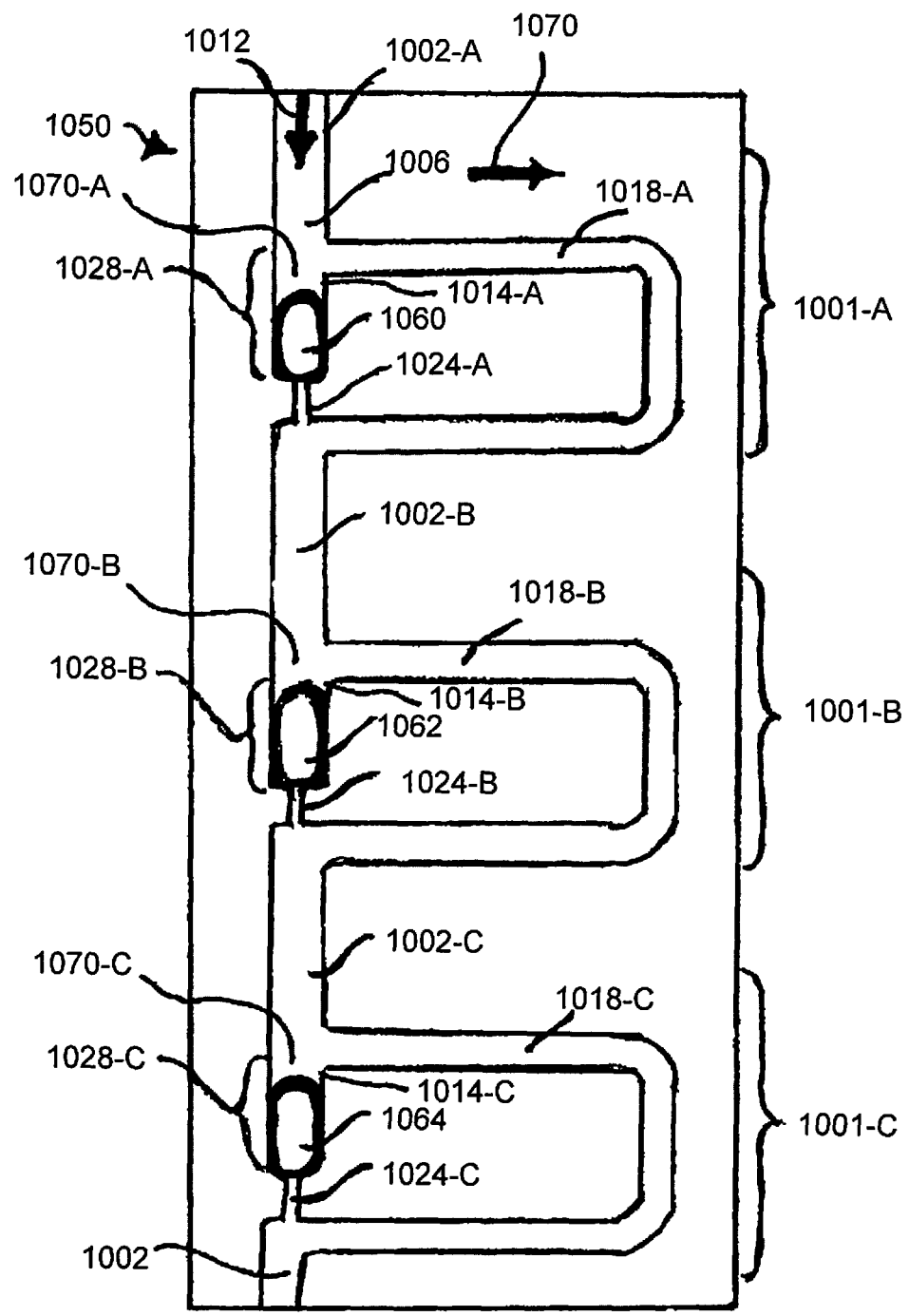
FIG. 4 is a photograph showing multiple droplets positioned in multiple regions of a microfluidic network according to one embodiment of the invention.

FIG. 4 shows the positioning of droplets 1060, 1062, and 1064 at positions 1028-A, 1028-B, and 1028-C, respectively, in microfluidic network 1050 according to one embodiment of the invention. As shown in this illustrative embodiment, carrier fluid 1021 flows in the direction of arrow 1012 and carries droplet 1060 through channel 1002-A and into fluidic path 1014-A due to the lower resistance to fluid flow in that fluid path compared to that of fluid path 1018-A. That is, prior to the positioning of droplet 1060 in region 1028-A, more than 50% of the fluid flowing in microfluidic channel 1002-A flows through fluid path 1014-A compared to fluid path 1018-A.

Once droplet 1060 is positioned at region 1028-A, it impedes fluid flow through fluid restriction region 1024-A such that the hydrodynamic resistances of fluid paths 1014-A and 1018-A are altered. This causes the hydrodynamic resistance of portion 1014-A to be higher, and as a result, a greater amount of fluid flows in the direction of 1070 through fluid path portion 1018-A. Accordingly, a second droplet 1062 flowing through microfluidic channel 1002-A and passing upstream portion 1006 now bypasses fluid path portion 1014-A and flows through portion 1018-A. The second droplet, after bypassing region 1028-A, now enters microfluidic channel portion 1002-B. If there is a lower hydrodynamic resistance in fluid path portion 1014-B compared to region 1018-B (e.g., a droplet has not already been positioned in region 1028-B), the droplet can be positioned at this region. Next, a third droplet 1064 can flow through microfluidic channel portion 1002-A in the direction of arrow 1012 and first bypasses region 1028-A due to droplet 1060 already positioned at that region. The droplet can then flow into fluid path portion 1018-A and 1002-B. Since droplet 1062 has already been positioned at region 1028-B, third droplet 1064 bypasses this region and takes the fluid path of least hydrodynamic resistance (fluid path portion 1018-B). Upon entering an empty region such as region 1028-C, the third droplet can now be positioned at that region due to a lower hydrodynamic resistance in fluid path 1014-C compared to that of fluid path portion 1018-C (e.g., prior to any other droplet being positioned at region 1028-C).

Accordingly, a method for positioning droplets in regions of a microfluidic network may include providing a microfluidic network comprising at least a first inlet to a microfluidic channel (e.g., positioned upstream of portion 1006 of FIG. 4), a first region (e.g., region 1028-A) and a second region (e.g., region 1028-B) for positioning a first and a second droplet, respectively, the first and second regions in fluid communication with the microfluidic channel, wherein the first region is closer in distance to the first inlet than the second region. The method can include flowing a first fluid (e.g., a carrier fluid) in the microfluidic channel, flowing a first droplet (e.g., a first fluid sample), defined by a fluid immiscible with the first fluid, in the microfluidic channel, and positioning the first droplet in the first region. The method can also include flowing a second droplet (e.g., a second fluid sample), defined by a fluid immiscible with the first fluid, in the microfluidic channel past the first region without the second droplet physically contacting the first droplet. The second droplet may then be positioned at the second region. In some instances, the first and/or second droplets are maintained at their respective regions while fluid continues to flow in the microfluidic channel.

It should be understood that other components may be integrated with fluidic networks described herein in some embodiments of the invention. For example, in some instances, hydrodynamic resistances of fluid paths can be changed dynamically such that the direction of fluid flow (and, therefore, positioning of droplets) can be controlled by the user. In one such embodiment, valves may be positioned at one or more of positions 1070-A, 1070-B, and 1070-C of FIG. 4. For example, a valve at position 1070-B can cause restriction of fluid flow through fluid path portion 1014-B, e.g., prior to a droplet being positioned at region 1028-B. This can cause a droplet flowing through microfluidic channel portion 1002-B to bypass region 1028-B even though a droplet is not positioned at that region. Thus, the droplet flowing through portion 1002-B will flow through fluid path 1018-B and onto the next available region, where the fluid resistance of that region may or may not be controlled by a similar valve. In some instances, after a droplet bypasses region 1028-B due to a closed valve at position 1070-B (or any other component that can change the relative resistances to fluid flow between fluid paths 1014-B and 1018-B), the valve at position 1070-B can now be reopened to change the relative resistances to fluid flow such that a next droplet can now enter into region 1028-B and be positioned at that region. Such a system can allow droplets to be positioned at any desired region of a microfluidic network.

As described herein, in some embodiments droplets do not require stabilization (e.g., the use of surfactants or other stabilizing agents) in order to be positioned at predetermined regions within microfluidic networks described herein. This is because in some embodiments, the droplets do not significantly physically contact one another during bypass of one droplet to another. Due to the little or no physical contact between the droplets, the droplets do not have a chance to coalesce with one another. Thus, surfactants or other stabilizing agents are not required to stabilize the droplets from coalescing in some such embodiments.

In some embodiments, the absence of surfactants or other stabilizing agents causes the droplets to wet a surface of the microfluidic network. Even though wetting may occur, the droplets can still be positioned at predetermined regions within the microfluidic network due to, for example, a positive pressure that causes fluid flow to carry these droplets into these regions. As discussed above, the use of droplets and/or a carrier fluid that does not contain a surfactant is advantageous in some embodiments where surfactants may negatively interfere with contents inside the droplets. For example, the droplets may contain proteins, and surfactants are known to denature certain proteins to some extent. However, after manipulation of the droplet and/or carrying out a process such as a chemical and/or biological reaction inside the droplet, surfactants may no longer negatively affect the contents inside the droplet. Accordingly, in such cases, a surfactant or other stabilizing agent can be applied to the droplets after the droplets have been positioned at regions of the microfluidic network. In some embodiments, application of a stabilizing agent to a droplet after manipulation of the droplet and/or carrying out a process inside the droplet can facilitate mobilization of the droplet out of the region in which the droplet is positioned.

It should be understood, however, than in some embodiments, a droplet and/or a carrier fluid may contain a surfactant or other stabilizing agent that stabilizes a droplet prior to positioning of the droplet at a region in the microfluidic network. In some such embodiments, the stabilizing agent does not negatively interfere with contents (e.g., reagents) inside the droplet. Of course, such embodiments will depend on a variety of factors such as the type of stabilizing agent used, the contents inside the droplet, the application, etc.

Figure 5A:
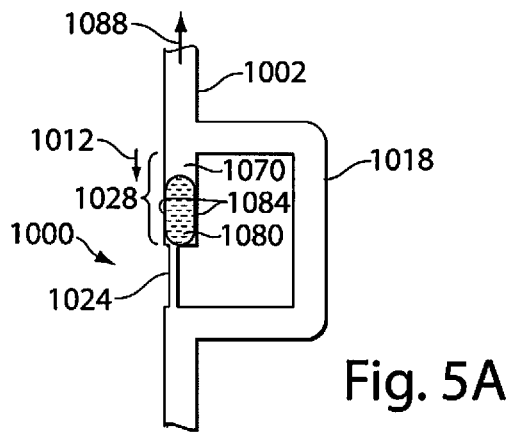
FIGS. 5A-5C show manipulation of a droplet positioned in a region of a microfluidic network by changing the surface tension of the droplet according to one embodiment of the invention.
Figure 5B:
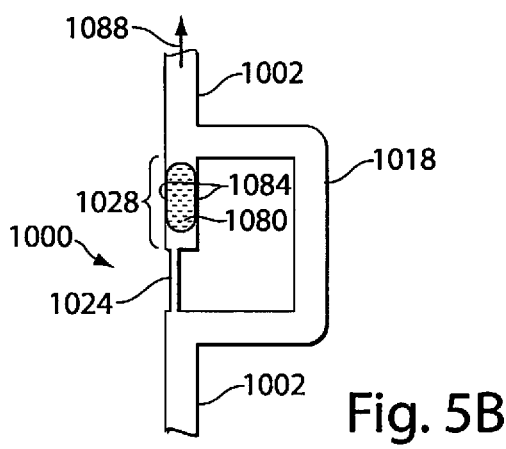
Figure 5C:
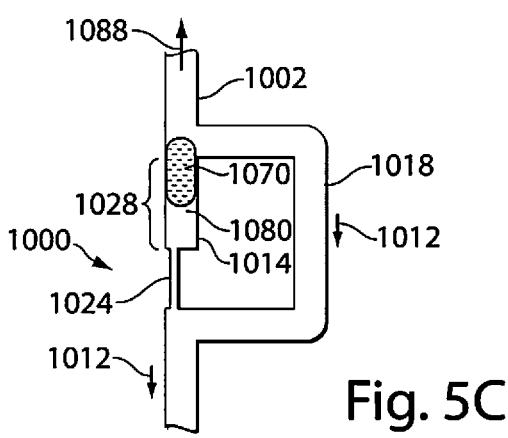

FIGS. 5A-5C show schematically the treatment of a droplet positioned at a predetermined region within a microfluidic network with a stabilizing agent according to one embodiment of the invention. As described above, droplet 1080 (which, in this embodiment, does not include a stabilizing agent) can be positioned at region 1028 by flowing a carrier fluid and the droplet in the direction of arrow 1012. After the droplet has been positioned, the droplet may wet a surface of the channel, such as surface portions 1084. (In other cases, however, the surface of the channel can be treated with a chemical coating so that the droplet does not wet the surface of the channel.) In some embodiments, wetting of the channel surface can cause the droplet to be immobilized at this region, even when a carrier fluid is flowed in the opposite direction (e.g., in the direction of arrow 1088) in attempt to remove the droplet from this region. In some such embodiments, a fluid comprising a stabilizing agent (e.g., a surfactant) can be flowed in the microfluidic network, e.g., in the direction of arrow 1088 through microfluidic channel 1002. A portion of this fluid can flow through fluid restriction region 1024 to reach droplet 1080 at region 1028. This fluid containing the stabilizing agent can cause the droplet to be coated with the stabilizing agent, which can result in the droplet de-wetting from the channel at surface portions 1084. In such cases, the surface tension of the droplet has been reduced. Thus, the droplet may be "depinned" from one or more surfaces of the channel.

If desired, after introducing a fluid containing a stabilizing agent to the droplet, the fluid flow may be stopped for a certain amount of time to allow the stabilizing agent to coat the droplet. In other embodiments, however, flow in channel 1002 is not stopped after the stabilizing agent has been introduced. In yet other embodiments, after a droplet has been de-wetted from a surface of the microfluidic network, fluid flowing in the microfluidic network may be replaced by a second fluid (which may or may not contain a stabilizing agent). As shown in the embodiment illustrated in FIG. 5C, droplet 1080 can be removed/extracted from region 1028 in the direction of arrow 1088. One of ordinary skill in the art can determine appropriate conditions for de-wetting a droplet from a surface of the microfluidic network which may depend on conditions such as the concentration of the stabilizing agent in the fluid, the flow rate, the degree of wetting of the droplet, the contents of the droplet, the material composition of the fluidic network, as well as other factors.

Figure 6:
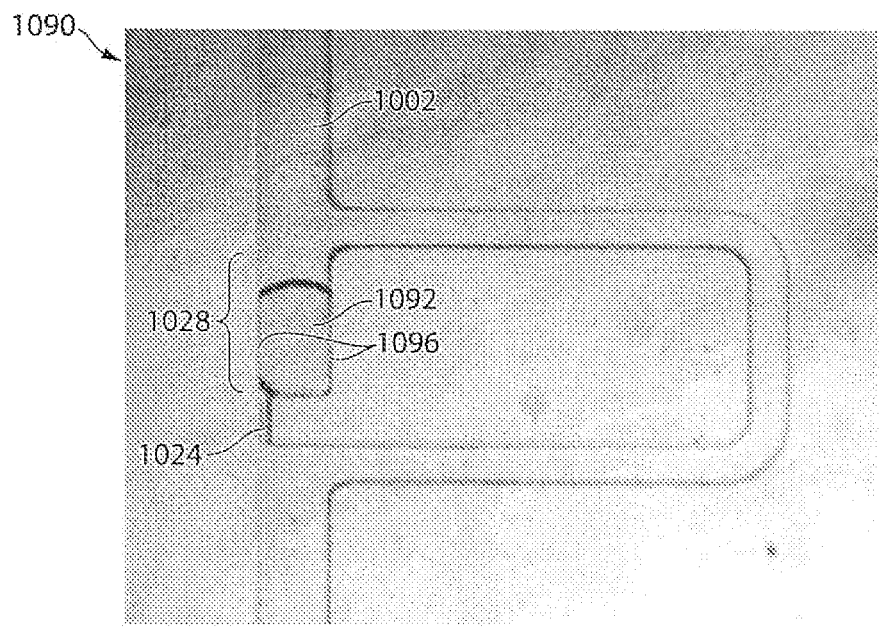
FIG. 6 is a photograph of a droplet wetting a surface of the microfluidic network according to one embodiment of the invention.
Figure 7:
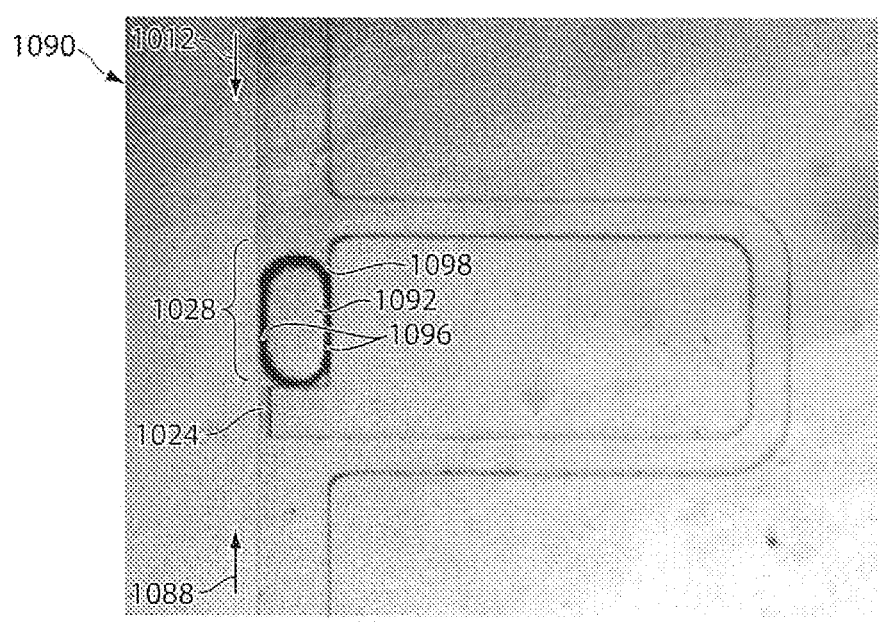
FIG. 7 shows de-wetting of the droplet from a surface of the microfluidic network after being treated with a stabilizing agent according to one embodiment of the invention.

FIG. 6 is a photograph showing droplet 1092 that has wetted surface portions 1096 of microfluidic network 1090 at region 1028. As shown in FIG. 7, after flowing a fluid containing a surfactant in the direction of arrow 1088, a portion of which flows through a fluid restriction region 1024, droplet 1092 de-wets surface portions 1096 and is now stabilized with the stabilizing agent. The stabilization is evident by meniscus 1098 that forms around droplet 1092, as the droplet now has a lower energy state configuration compared to that shown in FIG. 6.

It should be understood that a fluid containing a stabilizing agent can be introduced into microfluidic network 1090 in any suitable manner. For example, in some embodiments, the stabilizing agent may be introduced by a fluid flowing in the direction of arrow 1012. In other embodiments, region 1028 may be in fluidic communication with another portion of the device extending from region 1028. For instance, above or below region 1028 may be a reservoir, a channel, or other component that can be used to introduce a stabilizing agent or other entity to a droplet in that region.

As shown in FIGS. 2 and 5, droplets that are released from a region of a microfluidic network can be forced to flow in a direction opposite that which was used to position the droplet in the region. In other embodiments, however, after a droplet has been removed from region in which it was positioned, the droplet may be forced to flow in the same direction as that which was used to position the droplet. For example, in one embodiment, droplet 1080 of FIG. 5C can be released from position 1028 and can be forced to flow in the direction of 1088 until the droplet resides at a downstream portion of channel 1002 (e.g., at the top of microfluidic network 1000 as shown in FIG. 5C). Then, a valve or other component that may be positioned at position 1070 can be at least partially closed to cause a higher resistance to fluid flow in fluid flow path 1014 compared to that of 1018. Since fluid flow path 1018 now has a lower resistance to fluid flow, flow of the carrier fluid can now be reversed such that it flows in the direction of arrow 1012, in which case the droplet can bypass fluid flow path 1014 and enter fluid flow path 1018.

Different types of carrier fluids can be used to carry droplets or components in a microfluidic system. Carrier fluids can be hydrophilic (e.g., aqueous) or hydrophobic (e.g., an oil), and may be chosen depending on the type of droplet being formed or positioned (e.g., aqueous or oil-based) and/or the type of process occurring in the droplet (e.g., crystallization or a chemical reaction). In some cases, a carrier fluid may comprise a fluorocarbon. In some embodiments, the carrier fluid is immiscible with the fluid in the droplet. In other embodiments, the carrier fluid is slightly miscible with the fluid in the droplet. Sometimes, a hydrophobic carrier fluid, which is immiscible with the aqueous fluid defining the droplet, is slightly water soluble. For example, oils such as PDMS and poly(trifluoropropylmethysiloxane) are slightly water soluble. These carrier fluids may be suitable, for example, when fluid communication between the droplet and another fluid is desired. Diffusion of water from a droplet, through the carrier fluid, and into a second droplet is one example of such a case.

As described above, methods for storing and/or extracting droplets in a microfluidic network are provided herein. In some embodiments, the droplets may be stored and/or extracted in sequential order. For example, the droplets may be extracted in the order they are stored or positioned in predetermined regions in the microfluidic network. In other embodiments, the use of valves can allow only certain droplets to be released from regions of the microfluidic system. Advantageously, in some embodiments, such methods do not require the use of surfactants or other stabilizing agents, since the droplets may not come into substantial physical contact with one another in a manner that causes coalescence. This is advantageous in certain cases as surfactants may interfere with contents such as proteins inside the droplet, as is known to those of ordinary skill in the art.

In another aspect of the invention, a method of forming droplets in regions of a microfluidic device is provided. The method can allow production of droplets of a precise volume, which can be stored/maintained at precise regions of the device. The drops can be created at the storage region in a self-regulated manner. The method may include, optionally, filling a microfluidic channel with a filling fluid (e.g., oil). The oil can then be flushed out with a first fluid (e.g., an aqueous fluid) to be stored/maintained at a region of the device. This first fluid may be immiscible with the filling fluid. The first fluid can enter a region of the device for storing a droplet, replacing the filling fluid in that region. Next, a second fluid (e.g., a fluid immiscible with the first fluid) may be flowed in the channel, causing partitioning of a portion of the first fluid (e.g., at least in part through action of the second fluid). Partitioning of the first fluid causes formation of a droplet of the first fluid at the region, while a second portion of the first fluid bypasses the region. In this manner, a plurality of droplets can be generated sequentially down the length of the channel.

Advantageously, the devices and methods described herein may address several problems commonly associated with forming and/or storing droplets: (1) Each droplet of the same volume may be formed (or, the droplets may have different volumes, e.g., depending on the size of the positioning regions) and all of the first fluid (e.g., aqueous phase) may be used with zero or minimal waste, (2) Because the forming and/or positioning of the droplets is done by the serial application of single phase fluids, the process is simple and tolerant to a wide range of flow rates, pressures, fluids, and materials used to form the device. (3) Valves are not required in this device, which may make it easy to manufacture (although valves may be used with the device if desired), (4) Drop generation is robust and simple (e.g., in contrast to certain flow focusing and T-junction methods), (5) The method can be used to position/store reactive components besides (or in addition to) droplets, such cells as beads for use in PCR and ELISA type bioassays.

FIG. 8 shows a method for forming, positioning, and/or maintaining a droplet in a region of a microfluidic network according to one embodiment of the invention. The device used in this method may have the same configuration as that described in connection with FIGS. 1-7. As shown in illustrative embodiment of FIG. 8A, microfluidic network 1000 comprises section 1001 including microfluidic channel 1002 having an upstream portion 1006 and a downstream portion 1010 (as fluid flows in the direction of arrow 1012), with fluid paths 1014 and 1018 extending from the upstream portion and reconnecting at the downstream portion. In some cases, resistance to fluid flow may differ between fluid paths 1014 and 1018. For example, fluid path 1014 may have less resistance to fluid flowing in the direction of arrow 1012 prior to forming, positioning, and/or maintaining of a droplet in this section of the microfluidic network. As shown in this illustrative embodiment, fluid path 1014 has a lower hydrodynamic resistance than fluid path 1018 due to the relatively longer channel length of fluid path 1018. It should be understood, however, that the microfluidic network may have other designs and/or configurations for imparting different hydrodynamic resistances, and such designs and configurations can be determined by those of ordinary skill in the art. For instance, in some embodiments, the length, width, height, and/or shape of the fluid path can be designed to cause one fluid path to have a resistance to fluid flow different from another fluid path. In one particular embodiment, fluid path 1018 has at least one cross-sectional dimension (e.g., a width or height) that is less than a cross-sectional dimension to of fluid path 1014. In other embodiments, at least a portion of a fluid path may include an obstruction such as a valve (which may change hydrodynamic resistance dynamically), a semi-permeable plug (e.g:, a hydrogel), a membrane, or another structure that can impart and/or change hydrodynamic resistance in that portion.

Figure 8A:
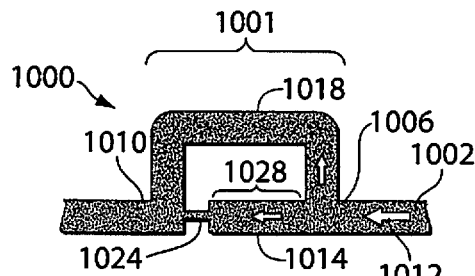
FIGS. 8A-8E show a method of forming a droplet and maintaining a droplet at a first region of a microfluidic device according to one embodiment of the invention.
Figure 8B:
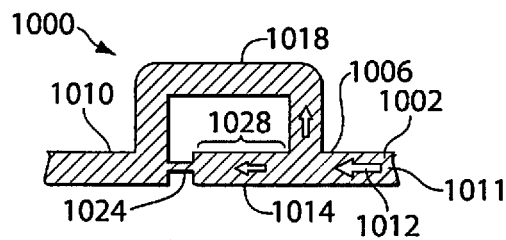
Figure 8C:
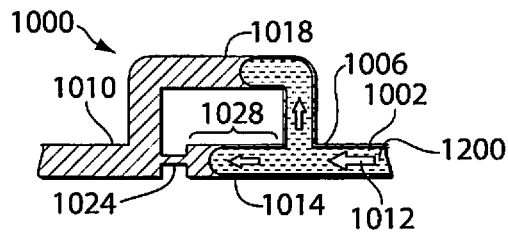
Figure 8D:
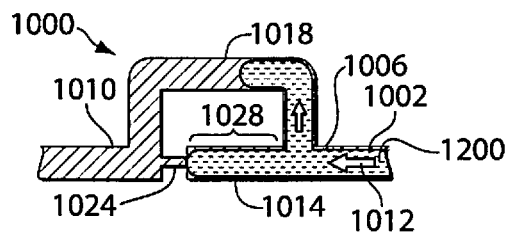

FIG. 8A shows an empty microfluidic channel. In one embodiment, a filling fluid 1011 (e.g., an oil) is flowed into channel 1002, filling the channel and fluid paths 1014 and 1018 as shown in FIG. 8B. As shown in FIG. 8C, a first fluid 1200 (e.g., a fluid to be stored as droplets) is flowed into channel 1002 in the direction of arrow 1012. At upstream portion 1006, a first portion of the fluid flows into fluid path 1014 while a second portion of the fluid flows into fluid path 1018. (The. first fluid may flow into fluid path 1014 before fluid path 1018 if fluid path 1014 is designed to have a lower hydrodynamic resistance than fluid path 1018.) As shown in the embodiment illustrated in FIG. 8D, once the first portion of the first fluid reaches a fluid restriction region 1024, the first portion cannot pass through this narrow portion due to the high hydrodynamic resistance of this fluid path (e.g., a meniscus formed between the first fluid and the filling fluid may cause "plugging" of the narrow fluid path). In some embodiments, the filling fluid can pass through fluid restriction region 1024, although in other embodiments, there is little or no fluid flow through this region.

Figure 8E:
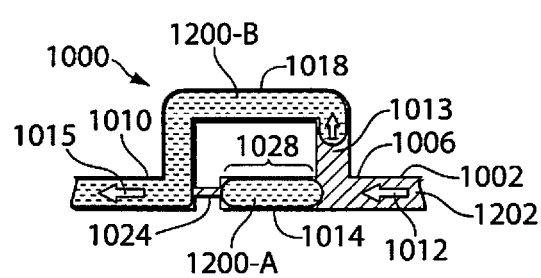

As shown in FIG. 8E, a second fluid 1202 may then be flowed into channel 1002 in the direction of arrow 1012. This second fluid may be immiscible with the first fluid. At upstream portion 1006, the second fluid bypasses fluid path 1014 (including region 1028) due the presence of the first fluid at that region. The flowing of this second fluid causes partitioning of the first fluid so as to form droplet 1200-A at the first region. Fluid path 1018, now having a lower resistance to fluid flow, allows second portion 1200-B of the first fluid to continue flowing in the direction of arrows 1013 and 1015, followed by second fluid 1202. As fluid path 1014 includes fluid restriction region 1024, droplet 1200-A cannot flow further down the microfluidic network. Accordingly, droplet 1200-A is positioned within a region 1028 (e.g., a "microwell") of the microfluidic network. In some embodiments, droplet 1200-A can be maintained at the region even though fluid continues to flow in the microfluidic network (e.g., in the direction of arrow 1012).

The size/volume of droplet 1200-A can vary and may depend and can be determined, at least in part, on the size/volume of region 1028. In some instances, droplets formed at a region have the same volume (or length) as that of the region. In other instances, droplets formed at a region have a different (e.g., a smaller or larger) volume (or length) as that of the region. The droplet may have a volume (or length) that is within, for example, 5%, 10%, 15%, 20%, 25%, or 30% of the volume (or length) of the region in which the droplet is positioned. In other cases, the volume (or length) of a droplet formed in a region is substantially smaller (e.g., less than 50%) than the volume (or length) of the region. For instance, if a region having a volume (or length) of X already contains a droplet having a volume (or length) of Y (e.g., using a method of positioning droplets as described in connection with FIGS. 1-7), a second droplet having an approximate volume (or length) of X-Y (X minus Y) may be formed/stored at the region by the methods described in connection with FIG. 8. This can allow the formation and/or positioning of multiple droplets in a single region of the device. Various sizes/volumes of droplets that can be formed/stored are described in more detail below.

As described above, in some embodiments, the positioning/presence of droplet 1200-A at region 1028 of FIG. 8 causes fluid path 1014 to be plugged such that no or minimal fluid flows past fluid restriction region 1024. This plugging of fluid path 1014 causes it to have a higher hydrodynamic resistance compared to fluid path 1018. As a result, when subsequent fluids are flowed in the direction of arrow 1012, the subsequent fluids bypass flow path 1014 and enter flow path 1018, which now has a lower resistance than that of fluid path 1014. Accordingly, once region 1028 has been "filled" with a droplet, other regions downstream can be filled with droplets (e.g., by the formation of droplets at these regions). This allows a plurality of droplets to be generated/stored sequentially down the length of the channel.

Accordingly, one method of the invention comprises providing a microfluidic network comprising a first region (e.g., region 1028) and a microfluidic channel (e.g., microfluidic channel 1002) in fluid communication with the first region, flowing a first fluid (e.g., fluid 1200) in a first direction in the microfluidic channel (e.g., in the direction of arrow 1012), flowing a second fluid (e.g., fluid 1202) in the first direction in the microfluidic channel, partitioning at least a portion of the first fluid at the first region so as to form a first droplet (e.g., droplet 1200-A) of the first fluid at the first region, and maintaining the droplet at the first region while fluid is flowing in the first direction. In some instances, forming and/or maintaining of a droplet at a region is independent of flow rate of the first fluid in the microfluidic channel.

The method described in connection with FIGS. 8 and 9 can allow storage of a fluid (e.g., a first fluid) at a region, followed by the creation of a droplet of the first fluid. This method contrasts with the methods described in connection with FIGS. 1-7, where droplets are first formed and then stored in the microfluidic network. In some embodiments described herein, a combination of both approaches can be used.

It should be understood that when droplet 1200-A is formed/positioned at region 1028, the droplet may plug all or a portion of fluid path 1014 and/or fluid restriction region 1024. For instance, in some cases, the droplet plugs all of such fluid paths such that none of the fluid flowing in microfluidic channel 1002 passes through fluid restriction region 1024. In other embodiments, the droplet may plug only a portion of such fluid paths such that some fluid passes through fluid restriction region 1024 even though the droplet is positioned at region 1028. The amount of fluid flowing past the droplet may depend on factors such as the dimensions of fluid path portions 1014 and/or 1024, the size of the droplets, the flow rate, etc. As long as the droplet causes fluid path 1014 to have a higher relative resistance to fluid flow than fluid path 1018, a second fluid (e.g., fluid 1202) can bypass fluid path 1014 and enter fluid path 1018.

As described above, fluid paths 1014 and 1018 may have different resistances to fluid flow depending on whether or not a droplet has been formed or positioned at region 1028. In the absence of a droplet at region 1028, fluid path 1014 may be configured to have a lower resistance to fluid flow than fluid path 1018. For example, greater than 50%, greater than 60%, greater than 70%, greater than 80%, or greater than 90% of the fluid flowing in channel 1002 at upstream portion 1006 may flow in fluid path 1014 compared to fluid path 1018. However, when a droplet has been formed, positioned and/or maintained at region 1028, fluid path 1014 may have a relatively higher hydrodynamic resistance. For example, less than 50%, less than 40%, less than 30%, less than 20%, or less than 10% of the fluid flowing in channel 1002 at upstream portion 1006 may flow in fluid path 1014 compared to that of 1018. In some cases, 100% of the fluid flowing in direction 1012 in microfluidic channel 1002 flows in fluid path 1018 upon positioning of a droplet at region 1028.

In some embodiments, partitioning of the first fluid into a first portion at region 1028 to cause formation of droplet 1200-A of the first fluid (e.g., a first droplet), can result in the droplet "recoiling" such that it has a slightly smaller volume than that of region 1028. In some instances, this recoiling causes certain subsequent fluids flowing in the microfluidic channel (e.g., a third fluid that is miscible with the first fluid) to not come into contact with the droplet stored at region 1028. The third fluid may be in the form of, for example, a fluid stream or a droplet. If the third fluid is in the form of a second droplet, the second droplet may not come into contact with the first droplet. Accordingly, in certain embodiments, a third fluid (e.g., second droplet or a fluid stream or portion of a fluid stream) does not physically contact the first droplet after forming and/or positioning of a first droplet in region 1028.

In other embodiments, a third fluid (e.g., second droplet or a fluid stream or portion of a fluid stream) comes into physical contact with the first droplet as it bypasses the first droplet, however, due to such minimal contact between the two fluids, the fluids do not coalesce. Accordingly, in some instances, the forming and/or positioning of droplets in the microfluidic network can take place without the use of surfactants. In other words, surfactants in either a fluid flowing in channel 1002 and/or within the droplets is not required in order to stabilize the droplets and/or prevent the droplets or fluids from coalescing with one another during forming, positioning or carrying the droplet in the microfluidic channel, and/or during maintaining the droplets within a predetermined region within the microfluidic network. However, in instances where coalescence is desired (e.g., to allow a reaction between reagents contained in two droplets), the microfluidic network and methods for operating the network can be configured to allow such physical contact and/or coalescence between droplets.

In some embodiments, methods for positioning a droplet in a microfluidic network include the steps of providing a microfluidic network comprising a first region (e.g., region 1028 of FIG. 8A) and a microfluidic channel in fluid communication with the first region, flowing a first fluid (e.g., a fluid to be stored) in the microfluidic channel, partitioning a first portion of the first fluid at the first region (at least in part through action of the second fluid) so as to form the first droplet at the first region, and partitioning a second portion of the first fluid at the second region (at least in part through action of the second fluid) so as to form the second droplet at the second region. In some cases, the first and second fluids are immiscible. The first droplet may be formed, positioned and/or maintained at the first region while the first fluid and/or second fluid is flowing in the microfluidic channel. In some embodiments, forming, positioning and/or maintaining the first droplet at the first region does not require the use of a surfactant in the first or second fluids.

Another method of the invention comprises providing a microfluidic network comprising at least a first inlet to a microfluidic channel (e.g., positioned upstream of portion 1006 of FIG. 8), a first region (e.g., region 1028-A) and a second region (e.g., region 1028-B) for forming a first and a second droplet, respectively, the first and second regions in fluid communication with the microfluidic channel. The method can include flowing a first fluid in the microfluidic channel and partitioning a first portion of the first fluid at the first region, at least in part through action of the second fluid, so as to form the first droplet at the first region. The method can also include partitioning a second portion of the first fluid at the second region, at least in part through action of the second fluid, so as to form the second droplet at the second region. In some instances, the first and/or second droplets are maintained at their respective regions while fluid continues to flow in the microfluidic channel.

In some embodiments, a chemical and/or biological process and/or a manipulation process can be carried out in a droplet that is positioned at a region of a microfluidic network (e.g., droplet 1200-A of FIG. 8 while the droplet is positioned in region 1028). For example, a fluid sample in the droplet may undergo a process such as diffusion, evaporation, dilution, and/or precipitation. The droplet may be manipulated, for example, by changing the concentration of the fluid flowing in channel 1002 after the droplet has been formed/positioned at region 1028. In other embodiments, region 1028 is in fluid communication with another fluidic channel, flow path, reservoir, or other structure, e.g., via a semi permeable membrane that may be positioned adjacent the region (e.g., underneath or above region 1028), and manipulation of the droplet can occur via such passages.

Microfluidic network 1000 of FIG. 8 may include additional regions 1001 for forming/storing droplets. Accordingly, in some embodiments, a third fluid can be flowed in the microfluidic channel after flowing of the second fluid. The second and third fluids may be immiscible (while the first and third fluids may be miscible). The third fluid may be partitioned at a second region (e.g., at least in part by flowing of a fourth fluid past the second region) so as to form a second droplet at the second region. Several droplets, each containing different fluid compositions, can be formed and/or stored in regions of a microfluidic network using this process.

In some embodiments, a fluid of defined volume (e.g., a "slug") can be introduced into microfluidic networks described herein and portions of the fluid can be partitioned into regions of the fluidic network. For example, a slug having a volume of X may be flowed into a network having a plurality of sections 1001 (and regions 1028, having a volume of Y, where Y is less than X) and the slug can be partitioned at each region 1028. The first region may be filled with the fluid in the amount of volume approximately Y (and forming a droplet of the fluid having a volume of approximately Y at the first region), while the remainder of the slug (X-Y or X minus Y)

continues to flow down the network. A second region can then be filled with the fluid in the amount of approximately Y (and forming a droplet of the fluid having a volume of approximately Y at the second region), while the remainder of the slug (X-2Y) continues to flow down the network. This process can continue until the slug has a volume of zero. This method allows all of the fluid of the slug, e.g., a sample fluid, to be used in the microfluidic network with no or minimal waste.

Figure 9:
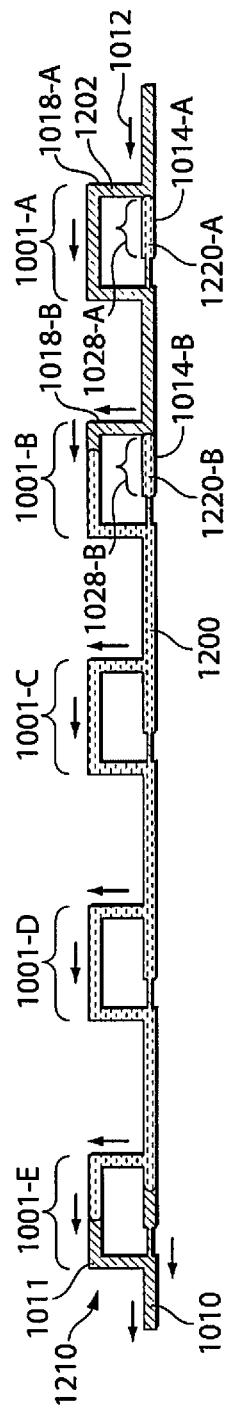
FIG. 9 shows a microfluidic device including several regions for forming droplets according to one embodiment of the invention.

As shown in FIG. 9, a microfluidic device 1210 may have a plurality of regions 1001-A-1001-E for forming, storing, and/or maintaining droplets. Microfluidic channel 1012 may first be filled by flowing a filling fluid 1011 in the direction of arrow 1012. Channel 1012 may then be filled by flowing a first fluid 1200 (e.g., in the form of a "slug") in the same direction. To form droplets of the first fluid, a second fluid 1202 may be flowed in the same direction. At section 1001-A, second fluid bypasses fluid path 1014-A and enters fluid path 1018-A due to the presence of the first fluid at region 1028-A. This causes the partitioning of the first fluid and the formation of droplet 1220-A. The second fluid continues to flow down the network, where it reaches section 1001-B. Due to the presence of first fluid at region 1028-B, the second fluid bypasses fluid path 1014-B and enters fluid path 1018-B. This process can continue until droplets are formed within regions of sections 1001-C, -D, and -E.

In another aspect of the invention, microfluidic structures and methods described herein are designed for containing and positioning components (e.g., beads, cells, and other reactive or non-reactive components) in an arrangement such that the components can be grown, multiplied and/or manipulated and then tracked even after one or more of these processes has taken place.

As shown in the embodiment illustrated in FIG. 10, a microfluidic network 1000 as described above may be used for positioning such and other components. FIG. 10A shows an empty microfluidic channel with arrows that show possible paths for fluid flow. As shown in FIG. 10B, a first fluid 1200 containing reactive components 1230 and 1231 (e.g., a bead comprising an antigen) is flowed into channel 1002 in the direction of arrow 1012. At upstream portion 1006, a first portion of the fluid flows into fluid path 1014, carrying with it reactive component 1230, while a second portion of the fluid flows into fluid path 1018, carrying with it reactive component 1231. (A portion of fluid may flow into fluid path 1014 before fluid path 1018 if fluid path 1014 is designed to have a lower hydrodynamic resistance than fluid path 1018.) Reactive component may reside in region 1028 if, for example, the size of the reactive component does not allow it to pass through fluid restriction region 1024. In some embodiments, the fluid can continue to pass through this region even though reactive component is present in region 1028, although in other embodiments, there is little or no fluid flow through this region while the reactive component is present in this region. Accordingly, reactive component 1230 is positioned within region 1028 of the microfluidic network. In some embodiments, reactive component 1230 can be maintained at the region even though fluid continues to flow in the microfluidic network (e.g., in the direction of arrow 1012).

Accordingly, a method of the invention comprises providing a microfluidic network comprising at least a first inlet to a microfluidic channel, a first and a second region for positioning a first and a second reactive component, respectively, the first and second regions in fluid communication with the microfluidic channel, wherein the first region is closer in distance to the first inlet than the second region, and flowing a first fluid comprising first and second reactive components in the microfluidic channel. The method may also include positioning the first reactive component at the first region, positioning the second reactive component at the second region, and maintaining the first and second reactive components in the first and second regions, respectively, while a fluid is flowing in the microfluidic channel.

Figure 10A:
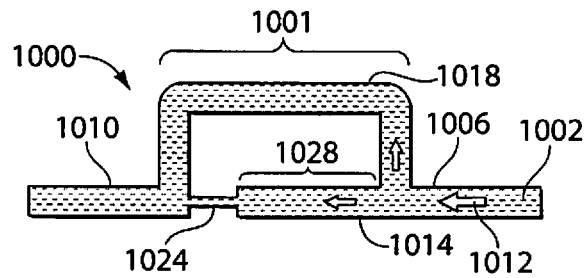
FIGS. 10A-10F show a method of positioning a reactive component at a region of a microfluidic device according to one embodiment of the invention.
Figure 10B:
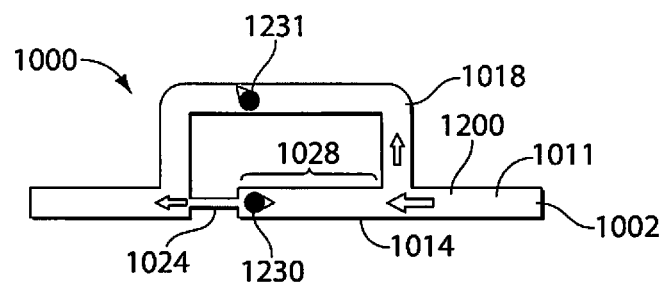
Figure 10C:
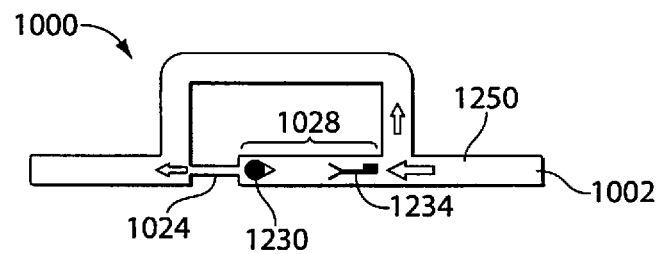
Figure 10D:
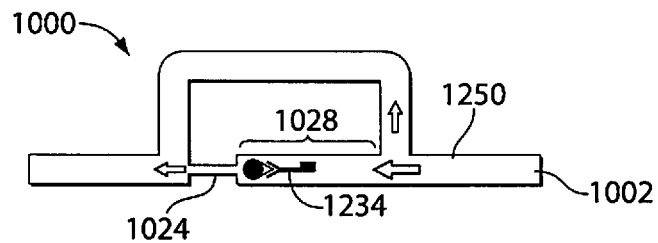

As shown in the embodiment illustrated in FIG. 10C, reactive component 1231 has now flowed past section 1001, while reactive component 1230 remains at region 1028. A second fluid 1250 may be flowed into channel 1002 in the direction of arrow 1012, e.g., to introduce another reactive component into the microfluidic network. The second fluid may enter both fluid path 1014 (including region 1028) and fluid path 1018. This second fluid may be miscible with the first fluid and may contain a reactive species 1234 (e.g., a human-antibody). In some cases, reactive species 1234 interacts (e.g., reacts, associates, or binds) with reactive component 1230, e.g., as shown in FIG. 10D. In one particular embodiment, reactive component 1230 includes a binding partner that is complementary to that of reactive species 1234 (e.g., an antibody-antigen binding pair).

Figure 10E:
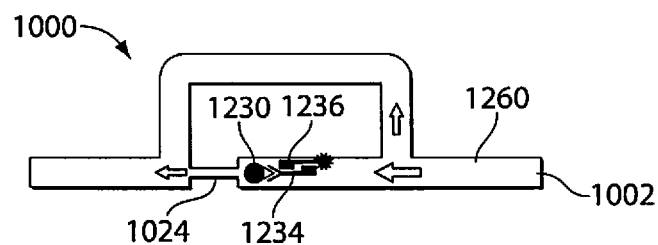

Next, a third fluid 1260 may be flowed in channel 1002 in the direction of arrow 1012, e.g., to introduce yet another reactive component into the microfluidic network. The third fluid may enter both fluid path 1014 (including region 1028) and fluid path 1018. This third fluid may be miscible with the first and/or second fluids and may contain a reactive species 1236 (e.g., an enzyme-linked anti-human antibody). In some cases, reactive species 1236 interacts (e.g., reacts, associates, or binds) with either reactive component 1230 or with reactive species 1234, e.g., as shown in FIG. 10E. In one particular embodiment, reactive component 1230 and/or reactive species 1234 includes a binding partner that is complementary to that of reactive species 1236 (e.g., an labeled-antibody-antigen binding pair). Optionally, a fluid such as a buffer may be flowed in the microfluidic system as a washing step to reduce any non-specific binding.

Figure 10F:
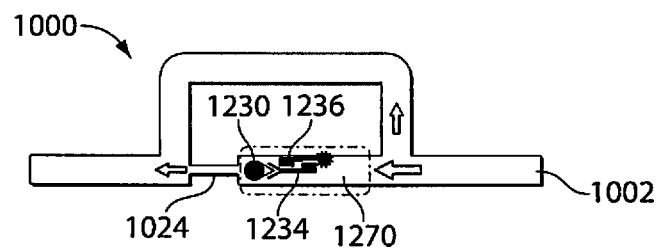

Optionally, a fourth fluid 1270 (e.g., an oil or a gel) immiscible with the third fluid may be flowed into channel 1002 in the direction of arrow 1012. The fourth fluid may enter region 1028 and, using the methods described above in connection with FIGS. 8 and 9, a droplet (e.g., containing the reactive component(s)) may be formed at the region, as shown in FIG. 10F.

In some embodiments, the positioning or presence of a reactive component at region 1028 causes at least a portion of fluid path 1014 to be plugged such it has a higher hydrodynamic resistance, resulting in less fluid flowing past fluid restriction region 1024 (relative to the absence of the component). This may cause fluid path 1014 to have a higher hydrodynamic resistance than fluid path 1018. As a result, when subsequent fluids (including additional reactive components) are flowed in the direction of arrow 1012, at least a portion of the subsequent fluids (and reactive components) may bypass flow path 1014 and enter flow path 1018, which now has a lower hydrodynamic resistance than fluid path 1014. Accordingly, once region 1028 has been "filled" with a reactive component, other regions downstream can be filled with reactive components. This allows a plurality of reactive component to be generated/stored sequentially down the length of the channel.

Reactive components may interact with reactive species by various methods. For example, interaction may be between a corresponding pair of components that exhibit mutual affinity or binding capacity, typically specific or non-specific binding or interaction, including biochemical, physiological, and/or pharmaceutical interactions. Biological binding defines a type of interaction that occurs between pairs of components including proteins, (e.g., adhesion proteins), nucleic acids, glycoproteins, carbohydrates; hormones and the like. Specific examples include cell (e.g., cell surface receptor)/protein, adhesion protein/integrin, antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. By carrying out the methods described above in connection with FIG. 10 in a device including a plurality of sections 1001, a plurality of reactive components can be positioned, stored, and/or maintained in the device. This can allow performance of a variety of reactions or analyses such as assays (e.g., ELISA) and PCR.

In some embodiments, reactive components such as cells can be encapsulated in a droplet (e.g., as part of a water-in-oil emulsions). The droplet may contain one or more reactants, nutrients, or drugs. The droplets may act as, for example, picoliter-scale reaction microvessels. Encapsulation can enable reactions involving, for instance, single molecules, such as in vitro translation of proteins from single genes, or DNA amplification of single genes by polymerase chain reaction (PCR). Droplets also provide an excellent method for studies of single, isolated cells, compounds they secrete, and/or growth rates of single cells.

A method involving the use of droplets as microvessels may require incubation and imaging of droplets. Certain existing methods allow collection and imaging of droplets, however, it is difficult to maintain the identity of the droplets. Using the articles and methods described herein, these challenges can be overcome in certain embodiments since each droplet may be associated with a particular region of the microfluidic device.

In one particular embodiment, cells can be encapsulated in a gel by using methods and articles described herein. By encapsulating cells in a hydrogel functionalized with the required reactants, heterogeneous assays can be performed in a three-dimensional scaffold. Placing hydrogels in a microfluidic network such as the one shown in FIG. 10 can allow reactions in a population of individual gels to be tracked over time.

In some embodiments, the microfluidic systems and methods described above and below can be used for containing and positioning cells, which can be grown, multiplied and/or manipulated in the microfluidic system. The cells (and their progeny) can be tracked even after one or more of these processes has taken place.

Genetically identical cells show phenotypic variation, for example during differentiation, development, and in response to environmental stress. The mechanisms of phenotypic variation are not fully understood, yet they are central to our understanding of major questions in biology such as differentiation and ageing. Gene expression patterns can be passed on to progeny cells, however, the mechanisms of non-genetic inheritance are not fully understood. To study phenotypic switching and epigenetic mechanisms of gene regulation, the systems and methods described herein can be used to study lineages of single cells and their progeny. For example, in some embodiments, single yeast cells can be trapped in long, thin chambers of a microfluidic device and the cells can be cultured so they grow in a line. This configuration facilitates the following of lineages deriving from a single progenitor cell. Cells can grow and divide in the chambers with typical doubling times, e.g., under constant flow conditions. As described in more detail below, generations of yeast cells can be tracked. The frequency of phenotypic switching of, for example, the GFP (green fluorescent protein)-fusion protein and PHO84-GFP, a high affinity phosphate transporter, can also be studied using the methods and devices described herein.

The methods can be applied to yeast cells, and more broadly to any suspension cell including blood cells, stem cells, and other mammalian cells that grow in suspension. This methods are also useful for staining single cells and their lineages: microcolonies deriving from single cells are cultured in the chambers, and then stained. Quantitative imaging can be applied to study correlations between stained entities (protein amount or localization, chromosome position, etc) and single cell genealogy or replicative age. Moreover, the antibodies and DNA probes required for immunofluorescence and fluorescence in situ hybridization (FISH) are expensive;

performing these assays in microfluidic devices described herein reduces the volume and thus cost of the required reagents. The methods and devices described herein can also enable imaging suspension cells over time.

Figure 11:
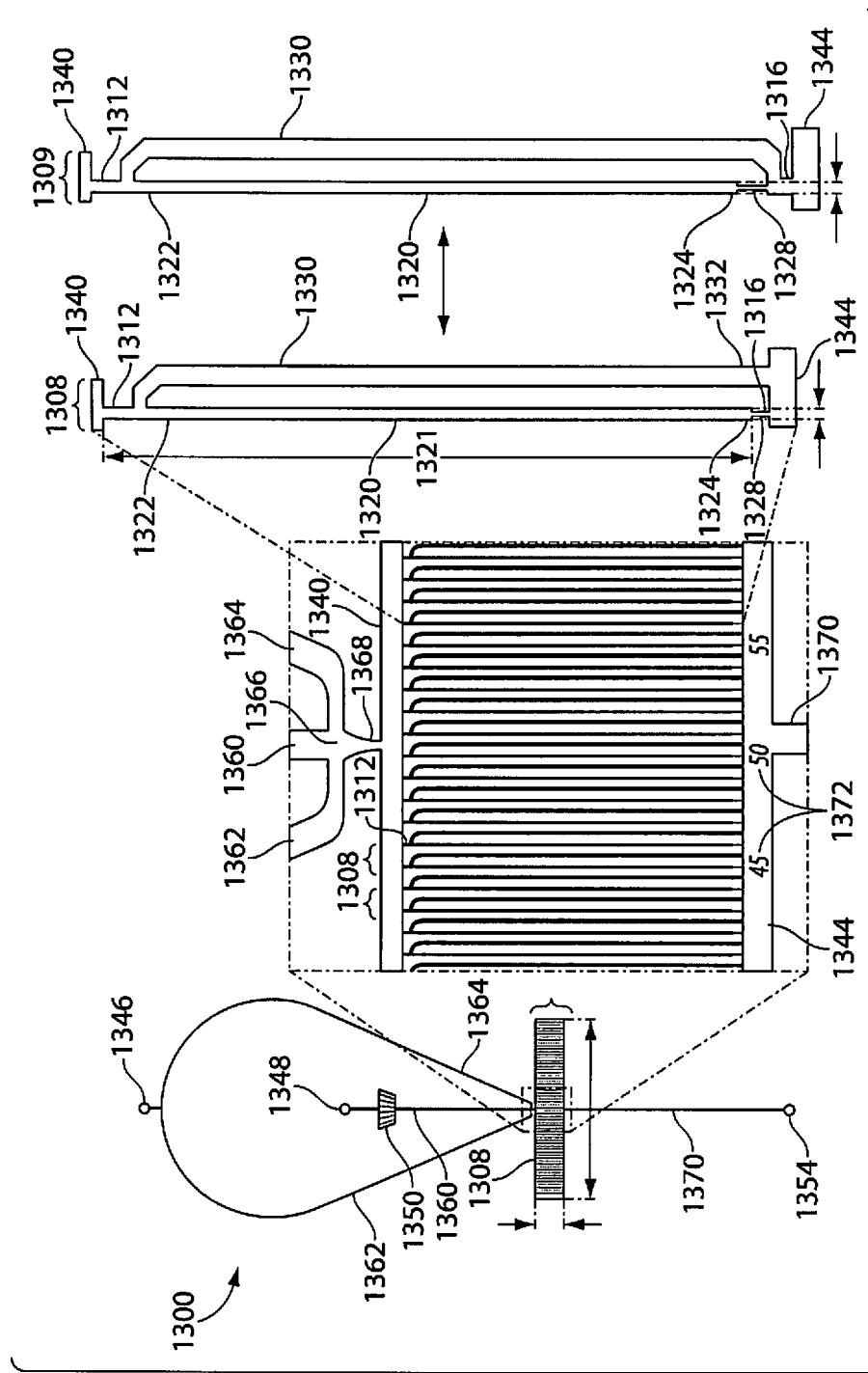
FIG. 11 shows a microfluidic device including a plurality of chambers according to one embodiment of the invention.

FIG. 11 is an example of a microfluidic system that can be used for controllably positioning cells or other components in certain regions of the system. As shown in the embodiment illustrated in FIG. 11, microfluidic system 1300 includes a plurality of chamber units 1308 (and/or, in other embodiments, chamber units 1309) positioned in parallel. The chamber units include a chamber inlet 1312, a chamber outlet 1324, and a chamber 1320 (having a length 1321) in fluid communication with the chamber inlet and the chamber outlet. As shown in the exemplary embodiment of FIG. 11, chamber 1320 is in the form of a long linear channel that can be used to position one or more components; however, it should be understood that any suitable shape and/or configuration of the chamber can be used in embodiments described herein. For instance, a chamber channel may be serpentine, curved, tapered, in the form of a reservoir, and the like.

At a downstream portion of chamber 1320 is positioned a fluid restriction region 1328, which, in some embodiments, may be in the form of a narrow channel. This fluid restriction region may allow certain components and/or fluids to pass therethrough, while inhibiting other components and/or fluids from passing therethrough, such that certain components and/or fluids are retained in chamber 1320. In some cases, once one or more components are positioned in a chamber, the position of the component(s) can be maintained in the chamber even during subsequent fluid flow in the chamber. This may occur, in some cases, if the component has an average cross-sectional area that is larger than a cross-sectional area of fluid restriction region 1328.

A fluid restriction region may be positioned at an upstream portion, a downstream portion, or in between an upstream and a downstream portion of the chamber. In some cases, a fluid restriction region is positioned between a chamber inlet and a chamber outlet. In other cases, a fluid restriction region is positioned outside of the chamber. In one embodiment, a fluid restriction region is positioned immediately adjacent a chamber outlet.

It should be understood that any suitable structure can be used as fluid restriction region 1328, which may have a higher hydrodynamic resistance and/or a smaller cross-sectional area for fluid flow than a region immediately upstream or downstream of the fluid restriction region. For instance, fluid restriction region 1328 may be in the form of a narrow fluid path or a channel having the same dimensions as chamber 1320, but having an obstruction (e.g., posts or a valve) positioned in or at that region. In other embodiments, fluid restriction region 1328 may comprise a porous membrane, a semipermeable plug (e.g., a gel), a valve, or another structure. In some cases, a fluid restriction region is a narrow channel portion that does not include a gel or other structure disposed therein; e.g., the size of the opening of the fluid restriction region alone can be used to trap, immobilize, and/or position components in a chamber fluidly connected to the fluid restriction region.

As shown in the illustrative embodiment of FIG. 11, chamber unit 1308 includes a chamber unit outlet 1344, which is the same as the outlet of fluid restriction region 1328. In chamber 1309, however, chamber unit outlet 1316 is downstream of fluid restriction region 1328. Other configurations of the chamber unit outlet are also possible.

Also included in chambers 1308 and 1309 are chamber bypass channels 1330, which extend from a portion of chamber 1320. One or more chamber bypass channels may extend from an upstream and/or downstream portion of the chamber. In some cases, a chamber bypass channel extends from the chamber between a chamber inlet and a chamber outlet (e.g., as illustrated in FIG. 11). In other cases, an inlet of the chamber bypass channel intersects an inlet of the chamber at an intersection.

In some embodiments, a chamber bypass channel has a lower hydrodynamic resistance than a chamber (e.g., prior to and/or after a component has been positioned in the chamber). As described in more detail below, this can allow more fluids and/or components to flow into the chamber bypass channel than the chamber. This arrangement may be useful for applications where it is desirable to position only one, or perhaps a few, components in the chamber. In certain embodiments where it is desirable to flow fluids and/or components out of the chamber bypass channel, the chamber bypass channel does not include any fluid restriction regions. This configuration may prevent any fluids and/or components from being immobilized in the chamber bypass channel. In other embodiments, however, a chamber bypass channel may include one or more fluid restriction regions.

As shown in the exemplary embodiment of FIG. 11, a plurality of chamber inlets 1312 may be fluidly connected to one or more feed channels 1340, which can allow delivery of fluid and/or components to the chamber inlets. Similarly, chamber outlets 1316 may be connected to one or more drain channels 1344. This arrangement can allow fluids and/or components which are not positioned in chamber 1320 to be collected and, optionally, recycled back into the microfluidic system (e.g., by fluidly connecting a drain channel to a device inlet). Although FIG. 11 shows each of the chamber inlets and chamber outlets being connected to feed channel 1340 and drain channel 1344, it should be understood that other configurations are possible. For example, in some embodiments, a first set of chamber units is connected to a first feed channel, and a second set of chamber units is connected to a second feed channel. In other embodiments, chambers or chamber units may be connected in series such that a chamber unit outlet of a first chamber is connected to a chamber inlet of a second chamber. In yet other embodiments, an outlet of a chamber bypass channel of a first chamber can be connected to an inlet of a second chamber. For example, chamber bypass channel 1330 of chamber unit 1308 may include a chamber bypass channel outlet 1332 that is connected to a chamber inlet 1312 of a second chamber, or between a chamber inlet and a chamber outlet of a second chamber, instead of being connected to drain channel 1344. In yet another embodiment, an outlet of a chamber bypass channel can be connected to a feed channel. In some cases, a combination of the configurations described above can be included in a single microfluidic system. Accordingly, different combinations of chambers positioned in series, parallel, and/or other arrangements can be included in microfluidic systems described herein.

A microfluidic device may include, for example, at least 10, at least 25, at least 50, at least 75, at least 100, at least 150, at least 200, at least 500, or at least 1,000 chambers or chamber units, which may be positioned in series and/or in parallel. The number of chambers or chamber units, in some cases, may depend on and/or may be limited by the size of the device, the size of the chamber units, and/or the application. Optionally, one or more chambers or chamber units may be labeled, e.g., using labels 1372, to identify the chambers or chamber units. Accordingly, any suitable number of chambers or chamber units may be included in a device. In addition, a device may include one or more microfluidic systems 1300 which can allow, for example, experiments under conditions or parameters to be performed simultaneously. Microfluidic system 1300 may also include one or more device inlets (inlets 1346 and 1348) for introducing one or more fluids into the microfluidic system. As shown in FIG. 11, a filter 1350 may optionally be positioned downstream of inlet 1348 (and/or inlet 1346) and upstream of the chambers and feed channel 1340. This filter can allow, for example, components of certain sizes to be flowed into the chambers, while to restricting components of other sizes from entering into the chambers. For example, the filter may allow single components having a particular size to be flowed into the chambers, while restricting agglomeration of components, which have a larger size, from entering into the chambers.

Inlet 1346 may be connected to two channel portions 1362 and 1364, and inlet 1348 may be connected to channel portion 1360. As illustrated, channel portions 1360, 1362, and 1364 may be arranged in a flow focusing arrangement. This arrangement can facilitate focusing of a component within channel portion 1360 towards a center portion of a fluid stream during laminar flow, e.g., when the channel portions intersect at intersection 1366 to form laminar streams of fluid. The fluid can then be introduced into microfluidic channel 1340 via inlet 1368. Other configurations of inlets are also possible.

Fluids flowing in channel portions 1362 and 1364 may be immiscible with a fluid flowing in channel portion 1360, which may allow formation of droplets of the fluid flowing in channel portion 1360 at or near inlet 1368 in some embodiments. In other embodiments, the fluids in channel portions 1360, 1362 and 1364 are miscible.

As described herein, a microfluidic system may be used to position one or more components in one or a series of regions (e.g., "microwells" or "chambers"). A variety of different components can be positioned at a region, including, for example, droplets, cells (e.g., bacterial, yeast, mammalian and stem cells), beads, tissues, and other entities. The number of components positioned at a region may depend on the size of the region. In some cases, a region (or a component) may have a dimension, such as a length, width, and/or height, of less than or equal to about 500 µm, less than or equal to about 250 µm, less than or equal to about 100 µm, less than or equal to about 50 µm, less than or equal to about 25 µm, less than or equal to about 10 µm, less than or equal to about 8 µm, or less than or equal to about 1 µm. The volume of the region (or component) can also vary; for example, the region (or component) may have a volume of less than or equal to about 50 µL, less than or equal to about 10 µL, less than or equal to about 1 µl, less than or equal to about 100 nL, less than or equal to about 10 nL, less than or equal to about 1 nL, less than or equal to about 100 pL, or less than or equal to about 10 pL. In certain embodiments, a region (or a component) may have a length of at least 1 μm, at least 10 μm, at least 25 μm, at least 50 μm, at least 100 μm, at least 200 μm, at least 250 μm, at least 500 μm, or at least 1,000 μm. Long regions may be suitable for positioning a large number of components at the region.

To position components in chamber of microfluidic system 1300, a first fluid stream including a plurality of components (e.g., cells) may be introduced into inlet 1348. Agglomeration of cells may be captured by filter 1350, e.g., a size exclusion filter, while allowing un-agglomerated cells to pass therethrough. A second fluid (e.g., a buffer solution) may be introduced into inlet 1346, and this fluid can flow into channel portions 1362 and 1364. The first fluid including the components may be focused as they pass through inlet 1368 into feed channel 1340. Since feed channel 1340 fluidly connects to a series of chamber inlets, the feed channel can distribute the fluids and the components to various chambers.

The geometry of the channels of the microfluidic system, the flow rate of the first and second fluids, and the concentration (or density) of the components in the first fluid can be chosen so as to allow delivery of a certain number of components into each of the chambers. For example, these parameters can be chosen such that at least 50%, at least 60%, at least 70%, at least 80%, or at least 90% of the chambers contain a predetermined number of components positioned therein. For instance, in one embodiment, only a single component is delivered to at least 50%, at least 60%, at least 70%, at least 80%, or at least 90% of the chambers of a microfluidic system. This can be achieved, in part, by designing the chambers to have a cross-sectional area on the order of the cross-sectional area of the component to be positioned. In addition, fluid restriction region 1328 may be designed such that introduction of a single component into the chamber channel substantially blocks or reduces fluid flow through this region. (In other embodiments, the fluid restriction region may be designed such that the introduction of exactly two components, or exactly three components, etc., causes substantial blockage of fluid flow through the fluid restriction region.) This blockage or reduction in fluid flow can result in the chamber being "filled", causing the chamber to have a higher hydrodynamic resistance than an empty chamber. Thus, fluid and components flowing in channel 1340 may prefer to flow into empty chambers (and/or through a chamber bypass channel) having a lower hydrodynamic resistance. The flow rate and the concentration (or density) of components in the fluids can also be adjusted to control the number of components in each chamber. This control can allow, for example, multiple experiments to be performed in parallel under similar or the exact same conditions.

Accordingly, a method may include flowing a fluid containing a plurality of components in a microfluidic system comprising a chamber having a flow direction, a chamber inlet, a chamber outlet, and a chamber bypass channel extending from the chamber between the chamber inlet and the chamber outlet. The method may also include positioning a component in the chamber, the chamber having a cross-sectional area, perpendicular to the flow direction, less than 2 times the largest cross-sectional area of the component perpendicular to the flow direction. A fluid may be flowed through the chamber while maintaining the component at its position in the chamber, and a portion of the plurality of components may be flowed in the chamber bypass channel.

As described herein, the dimensions of the chamber and fluid restriction region 1328 may be chosen such that a component, or a series of components, can be positioned, maintained, or trapped in the chamber channel without exiting the chamber via fluid restriction region 1328. In some cases, this positioning, maintaining, or trapping take place even while fluid continues to flow through fluid restriction region 1328. The fluid may be flowed at a substantially constant flow rate, at varying flow rates, or flow may take place periodically. This fluid flow may be important for applications that involve treating or manipulating the component(s) after it has been positioned in the chamber channel. For example, a continuous or periodic flow of nutrients may be supplied to cells that are trapped in a chamber channel. These nutrients can facilitate the growth and/or multiplication of the cells. Flow of dyes can allow the cells to be tagged and identified. In other embodiments, components that are positioned in a chamber can be subjected to a stress (e.g., different buffers, nutrients, or exposure to drugs) and the response of different components to the stress can be determined. Other applications are described in more detail below.

Flow of fluid (e.g., media) through the chambers is important for cell culture and also allows the cells to be exposed to controlled environmental changes, as well as immunostaining. Immunofluorescence of suspension cells is generally challenging. For yeast, the cell wall is typically enzymatically removed, and the cells are attached to a substrate using a chemical crosslinker. The cells are then fixed and permeabilized. Other suspension cells are typically centrifuged onto a surface-treated, glass microscope slide before staining. Moreover, immunostaining techniques for suspension cells are typically not compatible with live cell imaging. Using the methods and systems described herein, however, live cells can be positioned and tracked controllably in regions of a microfluidic device, and environmental conditions can be varied, for example, by changing the fluids flowed in the region.

Figure 12A:
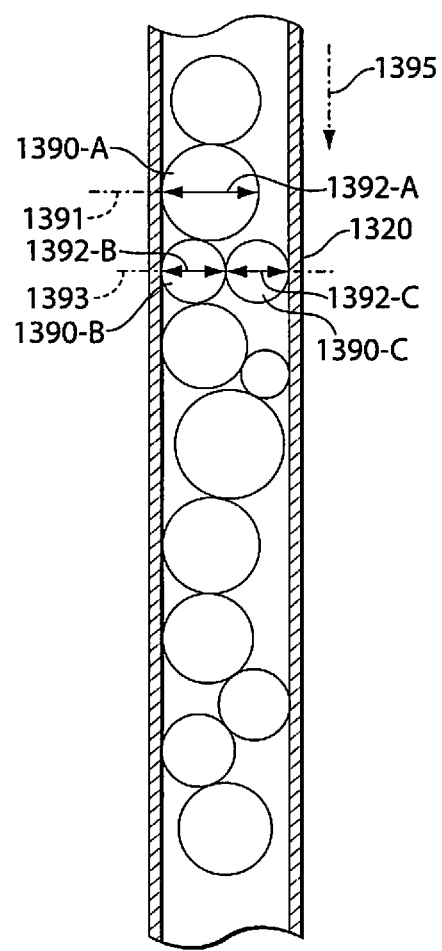
FIGS. 12A-12B show alignment of components in chambers of a microfluidic system according to one embodiment of the invention.

Furthermore, in some embodiments, the dimensions of the chamber can be chosen such that components in the chamber are positioned in a predetermined configuration. For example, the dimensions of the chamber may be chosen such that a series of components are generally aligned in the chamber. As used herein, "generally aligned" means no greater than 20% of the components in a chamber have the same position along the direction of bulk fluid flow in the chamber. The position of the components along the direction of bulk fluid flow can be determined by taking the cross-section of the component, perpendicular to the direction of (bulk) fluid flow in the chamber, which cross-section passes through the center of the component between two opposed points of a surface/surfaces of the component. For example, as shown in the illustrative embodiment of FIG. 12A, chamber 1320 includes a plurality of components 1390 that are generally aligned because less than 20% of the components in the chamber have the same position along the direction of bulk fluid flow, indicated by arrow 1395. The cross-section 1392-A of component 1390-A, perpendicular to bulk fluid flow, is shown to pass through the center of the component, and the component has a position 1391 (relative to the direction of bulk fluid flow). Component 1390-A has a different position along the direction of bulk fluid flow than that of components 1390-B or 1390-C. Component 1390-B has a cross-section 1392-B perpendicular to bulk fluid flow and component 1390-C has a cross-section 1392-C perpendicular to bulk fluid flow. Both of these cross-sections, and therefore both components 1390-B and 1390-C, have the same position relative to the direction of bulk fluid flow.

Figure 12B:
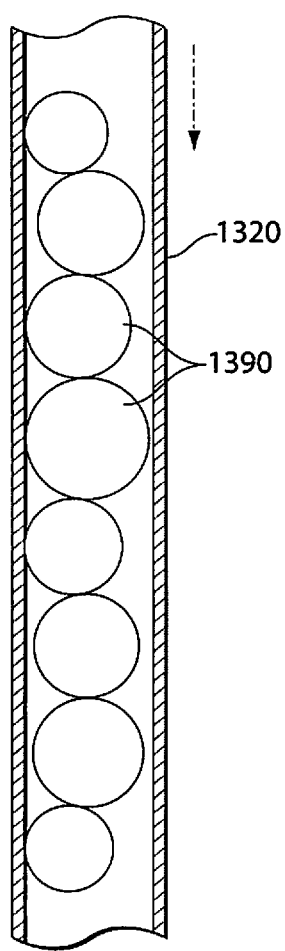

In some cases, no greater than 15%, 10%, 5%, or 2% of the components in a chamber have the same position along the direction of bulk fluid flow in the chamber. For example, sometimes 100% of the components in a chamber have different positions along the direction of bulk fluid flow in the chamber. When no greater than 5% of the components in a chamber have the same position along the direction of bulk fluid flow in the chamber, the components may be aligned "in a single line" in the chamber, as shown in the embodiment illustrated in FIG. 12B.

Aligned or generally aligned components can assist in identification of the components in a chamber. For example, if the components are cells derived from one cell, this configuration may be useful for tracking the lineology of the cells. In order to achieve the positioning of aligned or generally aligned components, the chamber may have a cross-sectional area perpendicular to the (bulk) flow direction that is, for example, less than 2 times the largest cross-sectional area of the component perpendicular to the (bulk) flow direction. In some cases, the chamber has a cross-sectional area, perpendicular to the (bulk) flow direction, that is less than 10 times, 7 times, 5 times, or 3 times the cross-sectional area of a component perpendicular to the (bulk) flow direction.

In some embodiments, at least 50%, at least 60%, at least 70%, at least 80%, or at least 90% of the components in a chamber have a largest cross-sectional area, perpendicular to the flow direction, of between 0.1 and 1.0 times (or between 0.3 and 1.0 times, or between 0.5 and 1.0 times) the cross-sectional area of the chamber perpendicular to the flow direction. It should be understood that the cross-sectional area may be static or dynamic, e.g., depending on the materials used to form the chamber. For example, a chamber may comprise an elastomer that allows it to expand upon having a high pressure in the chamber, or a large component positioned in the chamber. If a component completely blocks a portion of the chamber, even causing the chamber to expand, the largest cross-sectional area of the component perpendicular to the flow direction may be the same as (e.g., 1.0 times) the cross-sectional area of the chamber perpendicular to the flow direction.

In one particular embodiment, a system comprises a microfluidic device comprising an inlet, an outlet, a chamber having a (bulk) flow direction, and a flow restriction region fluidly connected to the outlet of the chamber. A plurality of cells may be generally aligned in the chamber, wherein at least 80% of the cells have a largest cross-sectional area, perpendicular to the flow direction, of between 0.1 and 1.0 times the cross-sectional area of the chamber perpendicular to the flow direction. In other embodiments, these dimensions are between 0.3 and 1.0 times, or between 0.5 and 1.0 times the cross-sectional area of the chamber perpendicular to the flow direction. The flow restriction region may be constructed and arranged to allow a fluid but not the cells to pass therethrough, thereby allowing the cells to be maintained in their positions in the chamber.

In certain embodiments, the chamber has a cross-sectional area having a different shape than a cross-sectional area of the component. For instance, the component may be round and the cross-sectional area of the chamber channel may be square. This shape difference can allow the components to be trapped in the chamber, but may allow fluids to pass the component at the corners of the chamber. Thus, a component may have a largest cross-sectional area, perpendicular to the flow direction, of less than 1.0 times, less than 0.8 times, or less than 0.5 times the cross-sectional area of the chamber perpendicular to the flow direction.

A cross-sectional area (or an average cross-sectional area) of a chamber (or a component) perpendicular to the (bulk) flow direction may be, for example, about 10,000 $\mu m^2$ or less, about 5,000 $\mu m^2$ or less, about 2,500 $\mu m^2$ or less, about 1,000 $\mu m^2$ or less, about 500 $\mu m^2$ or less, about 250 $\mu m^2$ or less, about 100 $\mu m^2$ or less, about 50 $\mu m^2$ or less, about 30 $\mu m^2$ or less, about 20 $\mu m^2$ or less, about 10 $\mu m^2$ or less, or about 5 $\mu m^2$ or less. As mentioned above, the cross-sectional area of a chamber may be chosen depending on factors such as the size of the components at or to be flowed in the chamber. The ratio of average cross-sectional areas of the chamber and the components (both measured perpendicular to the (bulk) flow direction) may be, for example, less than 20:1, less than 10:1, less than 5:1, less than 3:1, less than 2:1, or less than 1.5:1. Additionally or alternatively, the cross-sectional area of a chamber may be chosen depending on factors such as the cross-sectional area of a fluid restriction region, the number and type of components, and/or the fluids to be flowed in the system. The ratio of average cross-sectional areas of the chamber and a fluid restriction region (both measured perpendicular to the (bulk) flow direction) may be, for example, greater than 1:1, greater than 2:1, greater than 5:1, greater than 10:1, or greater than 25:1. In some cases, the ratio is between 3:1 and 8:1.

A cross-sectional area (or an average cross-sectional area) of a fluid restriction region (or the average cross-sectional area of the combined fluid paths in the case of a porous membrane or other structure having a plurality of fluid paths) may be, for example, about 5,000 $\mu m^2$ or less, about 2,500 $\mu m^2$ or less, about 1,000 $\mu m^2$ or less, about 500 $\mu m^2$ or less, about 250 $\mu m^2$ or less, about 100 $\mu m^2$ or less, about 50 $\mu m^2$ or less, about 30 $\mu m^2$ or less, about 20 $\mu m^2$ or less, about 10 $\mu m^2$ or less, or about 5 $\mu m^2$ or less, or about 1 $\mu m^2$ or less. In some cases, the cross-sectional area of a fluid restriction region may be chosen depending on factors such as the cross-sectional area of the chamber, the number, type and size of components, and the fluids to be flowed in the system.

In some embodiments, cells are positioned in a chamber and are allowed to multiply. Further analyses may involve comparing a characteristic of a first cell from a first generation to a characteristic of a second cell from a second generation. Additionally or alternatively, the cells can be subjected to a stress and/or a condition, and the response of one or more cells to the stress or condition can be determined. For example, comparative analyses may be performed by determining the response of at least two cells to a stress under controlled conditions.

Understanding how populations of single cells respond to environmental changes provides critical insights into variability in biological response, from differentiation to multidrug resistance. Imaging populations of single cells is challenging for cells that are not adherent. Suspension cells can be trapped in wells, however, it may be difficult to image non-adherent cells under changing environmental conditions. Budding yeast cells can adhere to treated surfaces (e.g. concanavalin A or agar pads), however, newly budded yeast cells may not adhere under flow conditions. Moreover, yeast cells bud in multiple dimensions (e.g., different focal planes), challenging the analysis of populations of cells over time. Using the devices described herein, individual cells can be placed in an array, cultured, imaged in a single focal plane, and can be subjected to changing conditions. Furthermore, the microfluidic systems described herein can be fabricated on a microscope slide, which can facilitate imaging and viewing of the systems. Accordingly, multiple flow experiments can be performed in parallel for the simultaneous study and/or comparison of different flow conditions or cell types.

It should be understood that a variety of different cells can be used in devices described herein. Non-limiting examples include yeast cells, bacteria, stem cells, and suspension cells. In some embodiments, the cells are round while the chambers are square, allowing for flow past the cells. Other geometries of chambers can also be used.

Certain existing methods for time-lapse microscopy of budding yeast under flow require that the cells are wedged into a chamber much smaller than the height of the cells themselves, so that they do not move during flow; however in such chambers, the cells are subjected to mechanical stress, which may affect the observed response. In addition, certain other existing methods allow cells to grow in a 2D plane, but the cells are randomly distributed in chambers and cannot be subjected to controlled flow conditions, making it difficult to obtain data on many single cell lineages in a single experiment as microcolonies interdigitate as they grow. Using the devices described herein can allow for fixing and staining of populations of single cells without imposing mechanical stress on the cells, while allowing precise positioning and control of the numbers of cells, and manipulation of cells, in chambers.

FIGS. 13A and 13B are bright field and fluorescence images, respectively, showing a plurality of chambers units 1308 including chambers 1320. An array of single, fluorescently tagged cells 1398 is positioned in the chambers. A group of cells 1399 is present in one of the chambers, and some chambers do not include any cells. The cells are prevented from reaching chamber outlet 1316 or from flowing downstream by fluid restriction region 1328.

Figure 14A:
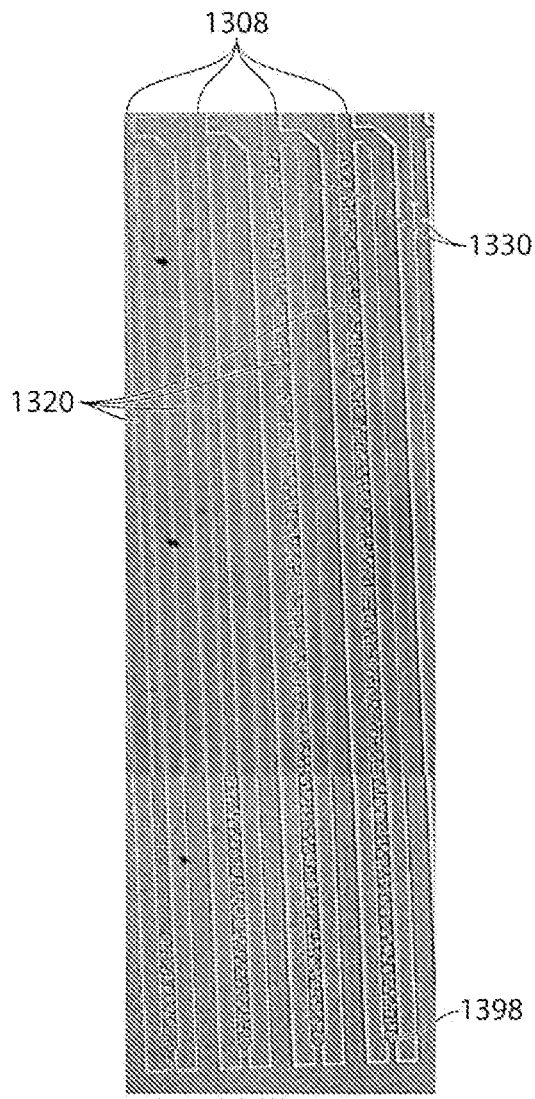
FIGS. 14A-14B are bright field and fluorescence images, respectively, showing a plurality of cells that have grown from single cells similar to the ones shown in FIGS. 13A and 13B.
Figure 14B:
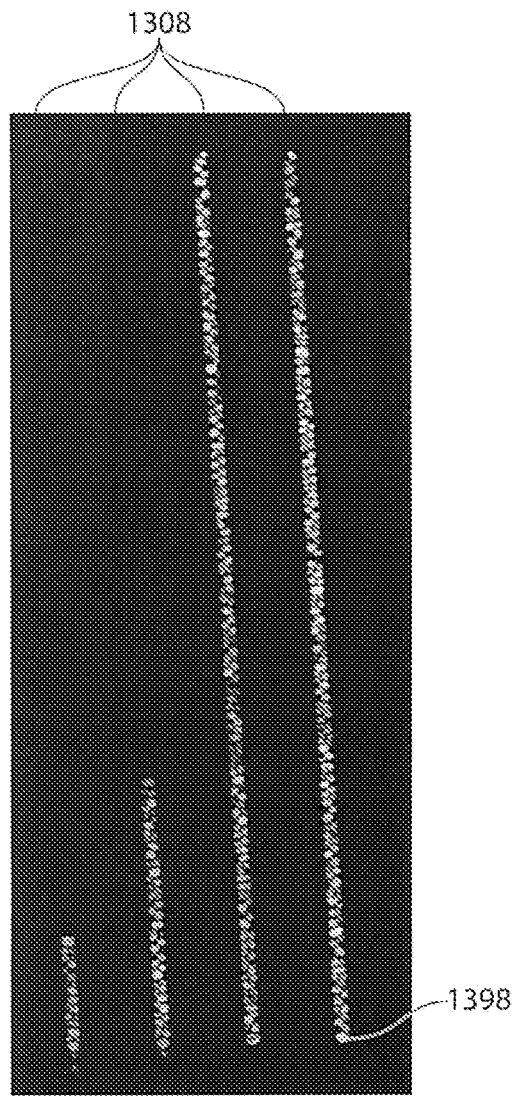

FIGS. 14A and 14B are bright field and fluorescence images, respectively, showing a plurality of cells in chambers 1308, which cells have grown from single cells similar to the ones shown in FIGS. 13A and 13B. Thus, cells can be multiplied in a chamber to form at least 2, at least 5, at least 10, at least 20, at least 50, or at least 100 progeny from a single cell. As shown in FIGS. 14A and 14B, the cells are generally aligned as they multiply.

Figure 15A:
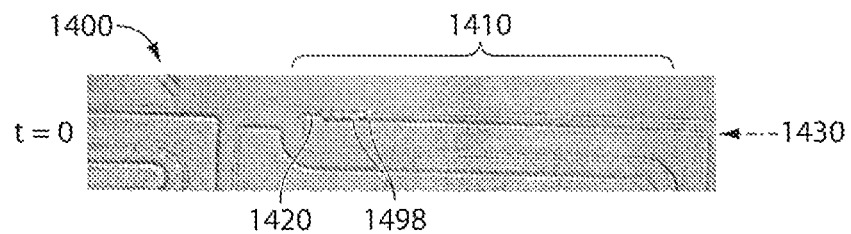
FIGS. 15A-15E are photographs showing the growth of cells at a region of a microfluidic device according to one embodiment of the invention.
Figure 15B:
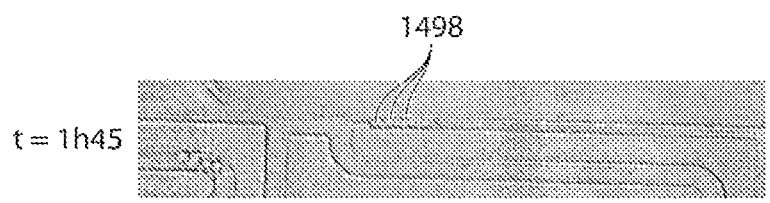
Figure 15C:
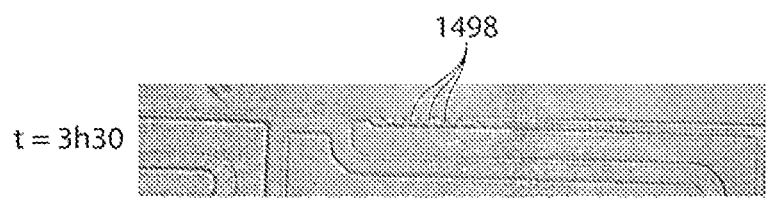
Figure 15D:
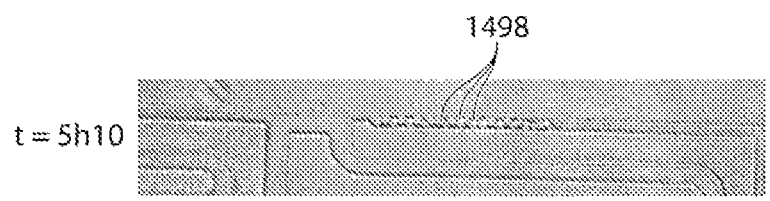
Figure 15E:
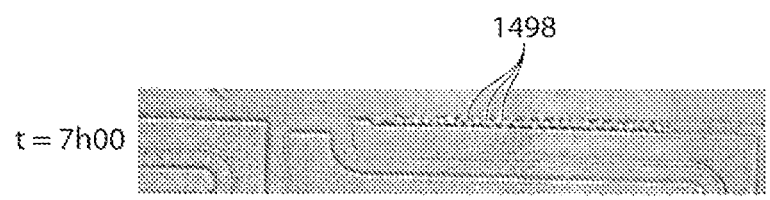

As shown in the embodiments illustrated in FIGS. 15A-15B, cells 1498 can be positioned and/or grown in single lines in chambers 1410 of a microfluidic network 1400. In some embodiments, microfluidic network 1400 may have the same configuration as network 1000 of FIG. 10, and chambers 1410 may be equivalent to regions 1028. Fluid restriction region 1420 restricts cells 1498 from flowing downstream in the direction of arrow 1430. A plurality of chambers 1410 may be positioned in series (as shown in FIGS. 15A-15B), and/or in parallel. In this particular embodiment, yeast cells (S. cerevisiae, s288c) are positioned in the form of a line in chamber 1410 at time=0 (FIG. 15A). The cells are round while the channels have a cross-sectional area in the shape of a square, so media (e.g., rich yeast media, YPD) can be continuously flowed through the channels (e.g., in the direction of channel 1430, although the reverse direction is also possible in certain embodiments). Since the channels are as wide as the cells, the cells are constrained to grow in a line. FIGS. 15A-15B show a time-course of images illustrating cell growth.

As shown in the embodiment illustrated in FIGS. 16A-16C, generations of cells 1498 cultured in a region of a microfluidic device can be tracked. FIG. 16A shows yeast cells expressing a fluorescent protein (S. cerevisiae, HXK1-GFP), which are grown in a chamber 1410. The design of this microfluidic network (e.g., microfluidic network 1000 of FIG. 10) provides an efficient method for making an array of single cells in regions of the device. These particular images were imaged by confocal laser scanning microscopy after ~20 hour incubation and growth shows variations in levels of gene expression (proportional to fluorescence intensity) through generations of cells. Cells can also be stained by other fluorescent probes in these chambers.

Figure 17A:
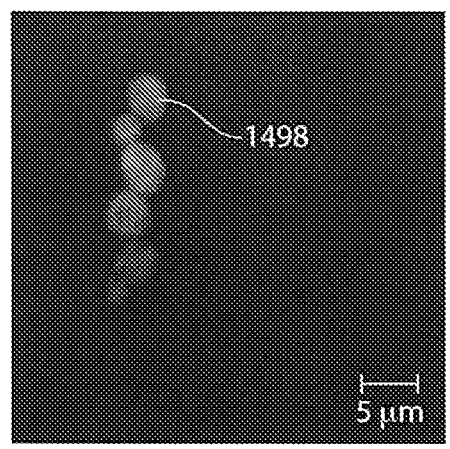
FIGS. 17A-17C show cells expressing a fluorescent protein at a region of a microfluidic device according to one embodiment of the invention.
Figure 17B:
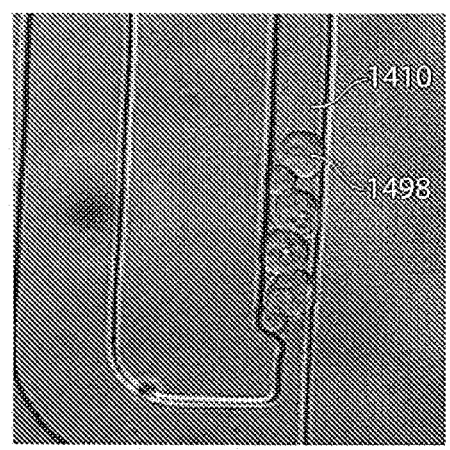
Figure 17C:
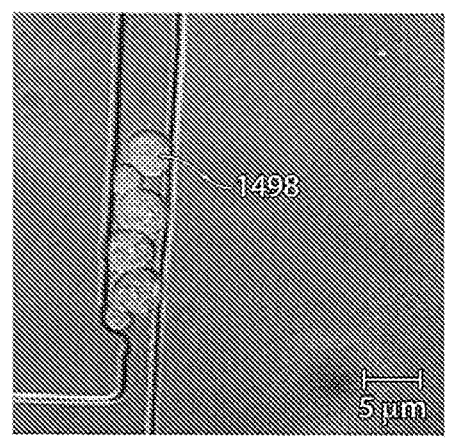

FIGS. 17A-17C show additional photographs of a chamber of a microfluidic network that can be used for growing and imaging cells. Here, the photographs show yeast cells expressing a fluorescent protein (S. cerevisiae, HXK1-GFP) after growth in a region of a microfluidic device. These regions can allow for yeast cells, including newly budded yeast cells, to be imaged over time under flow. This enables analysis of variations in response of populations of single cells to changing environmental conditions.

Figure 18A:
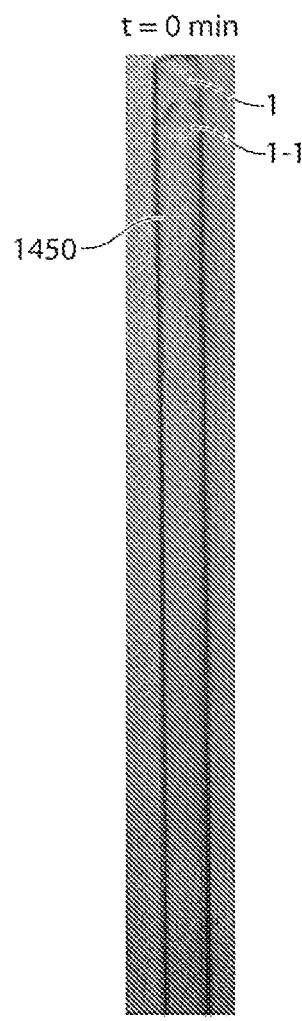
FIGS. 18A-18B show aligned cells and the tracking of cells in a chamber of a microfluidic system, according to one embodiment of the invention.
Figure 18B:
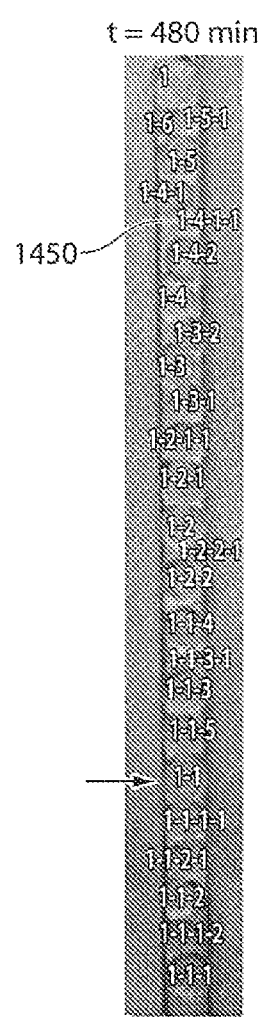
Figure 18C:
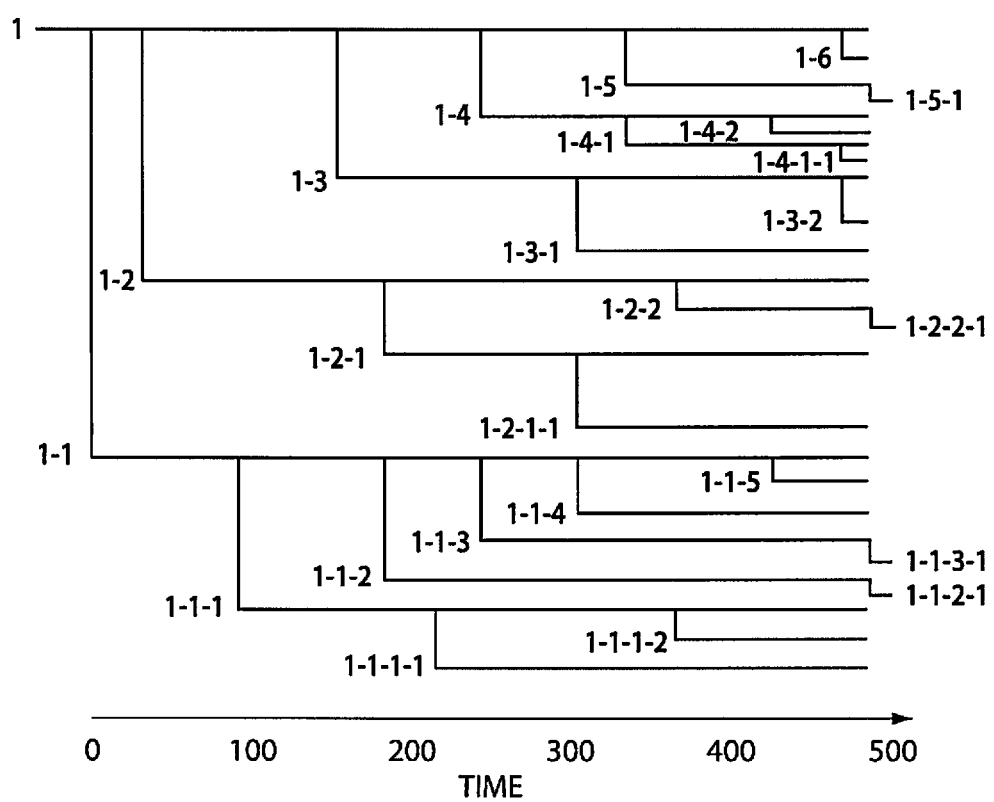
FIG. 18C shows a chart of the lineology of the cells shown in FIG. 18B.

FIGS. 18A-18C show the tracking of a lineage of yeast cells in a chamber. As shown in FIG. 18A, at time=0, cells 1 and 1-1 are positioned in chamber 1450 (where cell 1-1 previously budded from cell 1). As shown in FIG. 18B, the cells have multiplied further. Because the cells can bud to the right or left of a cell, cell 1-1 is now shifted and is positioned at a downstream portion of the chamber at time=480 min. The tracking of the cells can be performed by time lapse microscopy and a chart, such as the one shown in FIG. 18C, can be drawn based on this data.

As described herein, cells (or other components) can be labeled with an identifier (e.g., a dye, a probe, etc.) that identifies a particular portion of the cell and/or a particular process occurring in the cell. For example, cells labeled with GFP may show a certain level of gene expression within the cell. By combining this identification technique with methods described herein (e.g., the multiplication and tracking of cells in a chamber), gene expression of a lineage of cells can be tracked as a function of a cell's replicative age or history. In addition, these techniques may be useful for studying phenomena such as the age effects of DNA repair, how cells of different age respond to stress (e.g., exposure to different growth conditions, to a drug, and/or to a change in temperature (e.g., a heat shock), the stress of being in a densely packed environment, etc.), how gene expression levels depend on the family history of cells, and frequency of cell phenotype switching events. In some cases, these and other phenomena can be studied as a function of a cell's replicative age or history using the systems and methods described herein.

Figure 19:
FIG. 19 shows aligned cells in a chamber of a microfluidic system. The cells show different levels of gene expression and therefore have different intensities.

FIG. 19 shows a plurality of cells in a chamber with different intensities of fluorescence (the higher then number meaning greater fluorescence); these different intensities show that each of the cells has a different level of gene expression. The different fluorescent intensities of the cells can also aid in the tracking the cells (e.g., to form the chart shown in FIG. 18C) since each cell is "labeled" by having a different intensity.

Figure 20A:
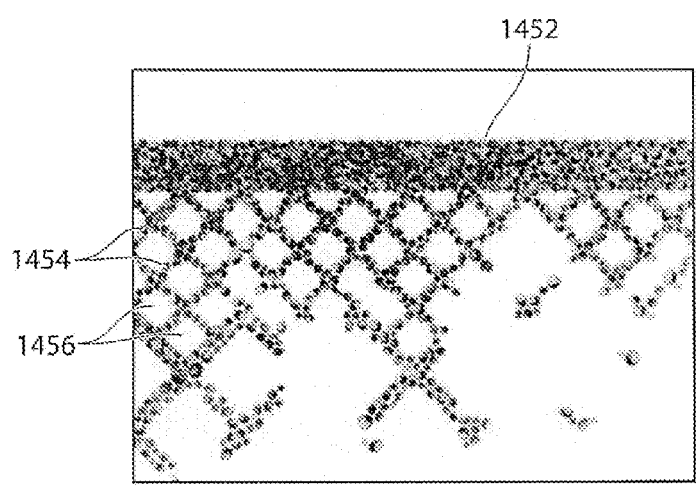
FIGS. 20A-20B show yeast cells grown in a chamber having a plurality of branching channels in the form of a grid according to one embodiment of the invention.
Figure 20B:
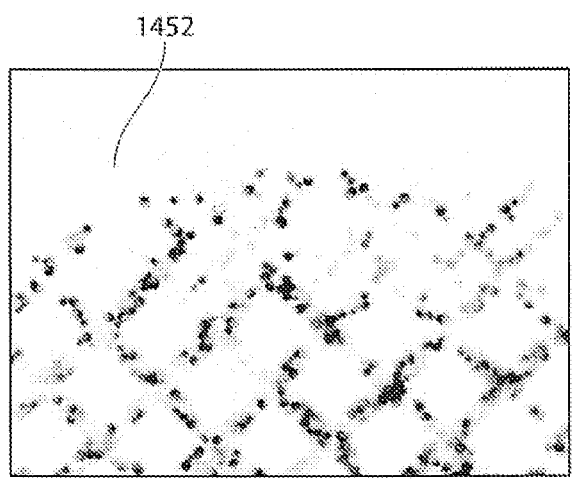

FIGS. 20A and 20B show yeast cells grown in a chamber 1452 having a plurality of branching channels 1452 in the form of a grid. Areas 1456 do not contain channels and, therefore, these areas do not contain cells. FIGS. 20A and 20B are inverted fluorescence images (e.g., cells that are dark are very bright with GFP). The cells are grown in different media: YPD (FIG. 20A) and synthetic dextrose media, SD (FIG. 20B). In the YPD media, all cells are "ON" (e.g., they fluoresce) because they all express pPHO84-GFP (i.e., GFP expressed under the control of the PHO84 promoter, where Pho84 is a high-affinity phosphate transporter). In the SD media (FIG. P2), some cells are "ON" and some are "OFF". These figures show that the type of media can cause cells to vary gene expression. These conditions can be varied and studied using microfluidic systems described herein.

Figure 21:
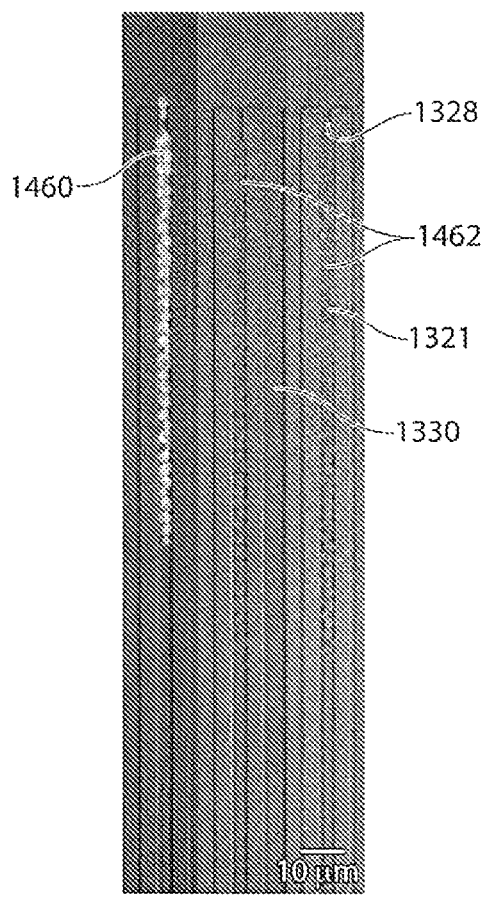
FIG. 21 shows phenotype switching of cells in response to being exposed to synthetic dextrose media according to one embodiment of the invention.

FIG. 21 shows cells grown in SD media and then cultured in the chambers of a microfluidic system similar to the one shown in FIG. 11. In these conditions, some cells (cells 1460) are "ON" and others (cells 1462) are "OFF". These lineages of cells can maintain the same phenotype for at least 7 generations.

In some cases, certain strains of the GFP-fusion collection showed a bimodal distribution of phenotypes ("ON" vs. "OFF") after culture from the harsh climate of a freezer.

Despite being genetically identical, these cells switch phenotype, and their progeny inherit this phenotype; this provides a model system to study epigenetic mechanisms in gene regulation. The systems and methods described herein can be used to identify colonies and/or conditions in which cells switch. This information may be relevant to the understanding of gene regulation in yeast cells, and more broadly, to the understanding of epigenetic timescales in adaptation and differentiation.

Figure 22:
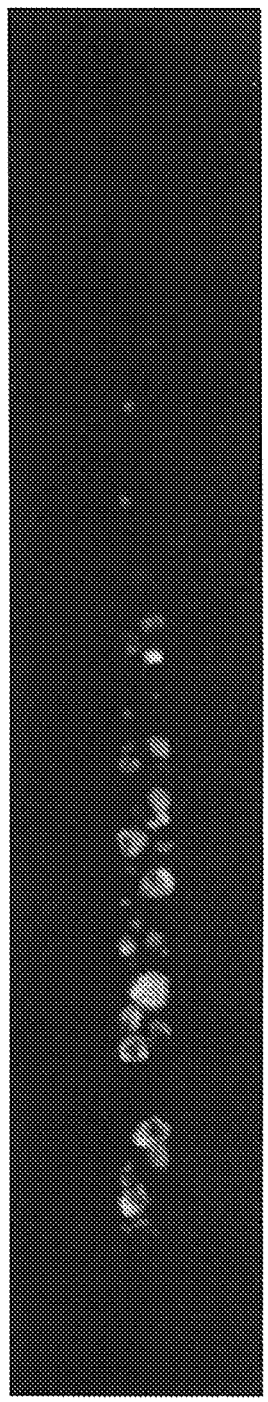
FIG. 22 shows FISH staining of cells positioned in a chamber according to one embodiment of the invention.

FIG. 22 shows a FISH staining using cDNA probes that bind to particular sequences of the cells' DNA. In this particular figure, the cDNA probes labeled the telomeres of the cells. The staining process involved heating the cells in the channel.

Figure 23C:
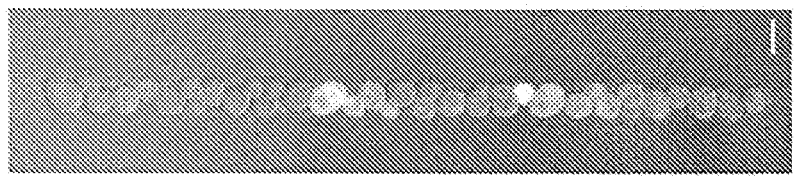
FIGS. 23A-23C show a screen of a GFP library of yeast cells positioned in a chamber according to one embodiment of the invention.
Figure 23B:
Figure 23A:
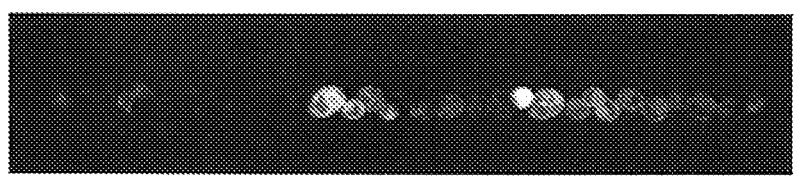

FIGS. 23A-23C show a screen of a GFP library of yeast cells positioned in a chamber. The cells were grown from a single cell that was under the stress of being grown in a densely packed environment. All cells were labeled with GFP, however, the cells show different levels of gene expression (and, therefore, have different fluorescent intensities) due to a change in environmental conditions (e.g., exposure to a different buffer). FIG. 23A is a fluorescent image, FIG. 23B is a brightfield image, and FIG. 23C is an overlay of fluorescent and brightfield images.

Figure 24C:
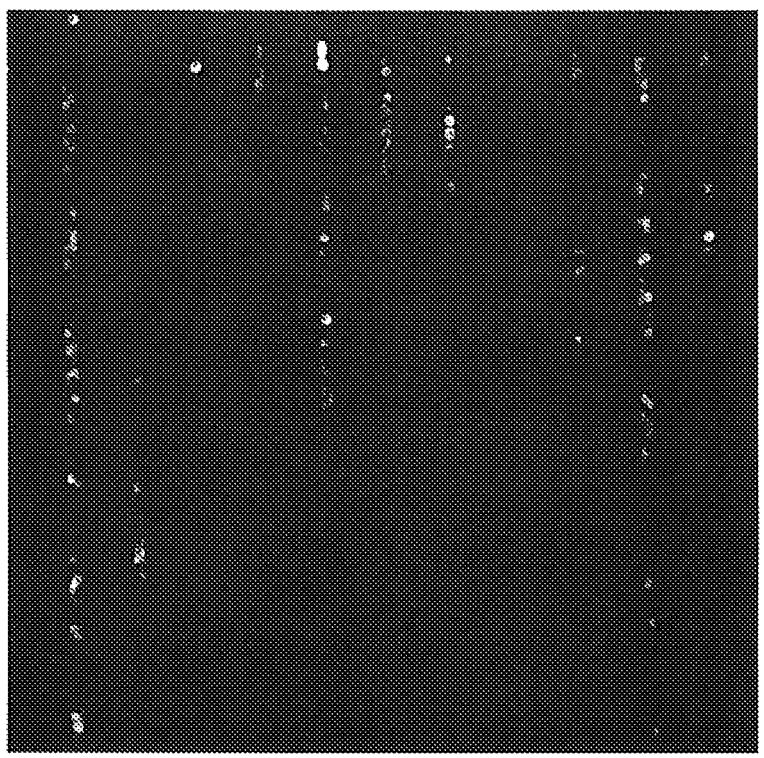
Figure 24D:
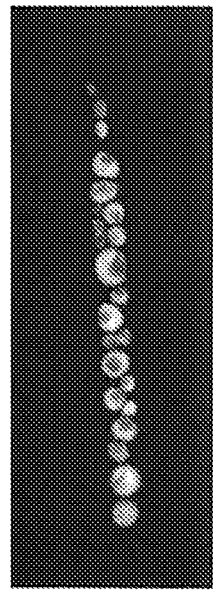
Figure 24E:
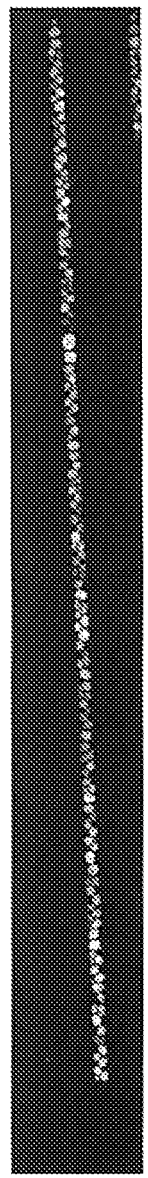

FIGS. 24A-24E show different levels of gene expression in cells that are exposed to various buffers. Yeast cells were labeled with HXK1-GFP (hexokinase isoenzyme). FIGS. 24A-24C show cells exposed to a synthetic dextrose buffer. Different cells had different levels of gene expression in this buffer. FIG. 24D shows cells exposed to YP-glycerol and FIG. 25E shows cells in a YP-galactose buffer; all of the cells had high levels of gene expression in these two buffers.

In other experiments, yeast cells were exposed to different concentrations of phosphate. High concentrations of phosphate caused the cells to turn "OFF", e.g., the cells having low levels of gene expression. Low concentrations of phosphate caused the cells to turn "ON", e.g., the cells having high levels of gene expression. Intermediate concentrations of phosphate caused the cells to enter into a bistable system where some progeny turned "ON", and some turned "OFF", the different levels switching every few generations.

In some embodiments, regions of a fluidic network such as microchannels, microwells, and/or chambers are defined by voids in the structure. A structure can be fabricated of any material suitable for forming a fluidic network. Non-limiting examples of materials include polymers (e.g., polystyrene, polycarbonate, PDMS), glass, and silicon. Those of ordinary skill in the art can readily select a suitable material based upon e.g., its rigidity, its inertness to (i.e., freedom from degradation by) a fluid to be passed through it, its robustness at a temperature at which a particular device is to be used, its hydrophobicity/hydrophilicity, and/or its transparency/opacity to light (i.e., in the ultraviolet and visible regions).

In some instances, a device is comprised of a combination of two or more materials, such as the ones listed above. For instance, the channels of the device may be formed in a first material (e.g., PDMS), and a substrate can be formed in a second material (e.g., glass).

Fluid channels and/or components described herein may have maximum cross-sectional dimensions less than 2 mm, and in some cases, less than 1 mm. In one set of embodiments, all fluid channels containing embodiments of the invention are to microfluidic or have a largest cross-sectional dimension of no more than 2 mm or 1 mm. In another embodiment, the fluid channels may be formed in part by a single component (e.g., an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) or regions described herein are less than about 500 microns, less than about 200 microns, less than about 100 microns, less than about 50 microns, or less than about 25 microns. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channels of the device may be hydrophilic or hydrophobic in order to minimize the surface free energy at the interface between a material that flows within the channel and the walls of the channel. For instance, if the formation of aqueous droplets in an oil is desired, the walls of the channel can be made hydrophobic. If the formation of oil droplets in an aqueous fluid is desired, the walls of the channels can be made hydrophilic.

In some cases, the device is fabricated using rapid prototyping and soft lithography. For example, a high resolution laser printer may be used to generate a mask from a CAD file that represents the channels that make up the fluidic network. The mask may be a transparency that may be contacted with a photoresist, for example, SU-8 photoresist, to produce a negative master of the photoresist on a silicon wafer. A positive replica of PDMS may be made by molding the PDMS against the master, a technique known to those skilled in the art. To complete the fluidic network, a flat substrate, e.g., a glass slide, silicon wafer, or a polystyrene surface, may be placed against the PDMS surface and plasma bonded together, or may be fixed to the PDMS using an adhesive. To allow for the introduction and receiving of fluids to and from the network, holes (for example 1 millimeter in diameter) may be formed in the PDMS by using an appropriately sized needle. To allow the fluidic network to communicate with a fluid source, tubing, for example of polyethylene, may be sealed in communication with the holes to form a fluidic connection. To prevent leakage, the connection may be sealed with a sealant or adhesive such as epoxy glue.

In some embodiments, the microfluidic networks described herein can be combined with one or more microfluidic components such as valves, pumps, droplet formation regions (e.g., in the form of a flow-focusing device), membranes, as well as those described in U.S. application Ser. No. 60/925,357, filed Apr. 19, 2007, and entitled "Manipulation of Fluids and Reactions in Microfluidic Systems", which is incorporated herein by reference in its entirety for all purposes. Any of a number of valves and/or pumps, including peristaltic valves and/or pumps, suitable for use in a fluidic network such as that described herein can be selected by those of ordinary skill in the art including, but not limited to, those described in U.S. Pat. No. 6,767,194, "Valves and Pumps for Microfluidic Systems and Methods for Making Microfluidic Systems", and U.S. Pat. No. 6,793,753, "Method of Making a Microfabricated Elastomeric Valve," which are incorporated herein by reference.

The following examples are intended to illustrate certain embodiments of the present invention, but are not to be construed as limiting and do not exemplify the full scope of the invention.

EXAMPLE 1

This example shows the design, fabrication, and operation of a microfluidic system for positioning, trapping and storing single cells in chambers according to one embodiment of the invention.

An array of chambers was designed to position, trap and store cells, the chambers having a configuration such as the ones shown in FIG. 11. Chambers were designed to have a flow restriction region at one end of the chamber such that cells would be trapped when they flowed into the chambers. Once a cell was positioned in a chamber, this increased the hydrodynamic resistance of the chamber. This caused subsequent cells in the fluid to enter a bypass channel extending from the chamber, instead of the chamber itself. This method allowed the formation of an array of single cells in the chambers.

In this example, the chambers were designed so they were just as wide as a single cell, with dimensions 5 μm high, 5 μm wide, and 400 μm long. Because of this restriction in height and width of the chamber, the cells were constrained to grow in a single line. While the cross-sections of the cells were approximately round, the chambers were approximately square, enabling media to be continually perfused through the chambers even while the cells were positioned in the chamber. The volume of a single chamber was 10,000 μm$^3$ and there was approximately 3,500 μm$^3$ free volume when the chamber was filled with cells. For longer-term culture applications, a porous membrane can be incorporated into the device (e.g., a porous may form one surface of the chamber), which may allow for additional media exchange along the length of the chamber. Examples of semi-permeable membranes are described in more detail in International Patent Apl. Serial No. PCT/US2006/034659, filed Sep. 7, 2006, entitled "Microfluidic Manipulation of Fluids and Reactions", which is incorporated herein by reference in its entirety for all purposes.

Before the cells reached the chambers, they were passed through a filter that was fabricated on-chip for both media and cell inlets. The smallest pore size of the filter was 5 μm, so aggregates of cells remained trapped in the filter. This filter helped to achieve the flow of only single cells (instead of agglomerations of cells) into the chamber array.

Over the time course of the experiments, cells trapped in the filter continued to grow. To avoid dislodged budding cells from the filter and contaminating cell lineages in the chamber array, a flow-focusing junction was included in the device design. During loading, media flowed in from the side channels (e.g., channels portions 1362 and 1364 of FIG. 11) at a low flow rate and focused the stream of cells (e.g., flowing from channel portion 1360) so they entered the chamber array. When loading was complete, the flow of cells was stopped and the media flow rate was increased. While some of the media flowed into the chamber array, media also flowed upstream into the channel containing the cells (e.g., channel portion 1360) and the filter. This upstream flow can prevent agglomerated and other cells trapped in the channel or filter from reaching the chambers.

Typical loading efficiencies of single cells in the chambers ranged from about 50-90%, e.g., depending on the flow conditions and the cell density. The majority of the remaining chambers were empty, and in a few instances cases, contained multiple cells.

The loading efficiencies can be optimized by varying one or both of the flow rate and cell density. For example, in some cases, a loading flow rate of 95 μL/hr with approximately $10^7$ cells/mL in the loading solution filled at least half of the chambers with a single cell after approximately 5 minutes of loading. In other cases, a concentration of approximately $10^6$ cells/mL was used. Depending on the flow rate and other conditions, an increase of the cell concentration or the loading time may lead to the positioning of multiple cells per chamber.

In chambers of these dimensions used in this experiment, over 100 cells derived from a single cell were captured in each chamber. Chambers may also be made longer to follow more generations. Over the course of 1000-1500 minutes, a relatively constant division time was observed, even for cells positioned adjacent the flow constriction region. This may suggest that the division of cells was not limited by the number of cells in the chamber (or by the dimensions of the chamber).

Once the cells are loaded in the chambers, a buffer was flowed through the chambers at rates of 55 μL/hr. Based on the volume of the device, the media was exchanged on timescales much less than the division time of the cells.

To evaluate growth of cells in the progeny chambers, cells were tracked using time-lapse microscopy. Images were acquired every 7 minutes. The average cell division time was comparable to bulk growth rates.

The chambers facilitated fast and efficient qualitative screening of single cells and their progeny. At the end of an experiment, images of the lines of cells were acquired. The number of single cells in "ON" and "OFF" states was easily determined to by simple analysis of the proportion of light to dark channels. The chambers also made it easy to investigate switching frequency for single cells.

For more detailed analysis of cells and their progeny, time-lapse imaging and analysis was performed. It was observed that cells and their closest progeny remained relatively close to each other within the channel, however, recently budded cells sometimes squeezed past each other in the chamber and disrupted the genealogical order of the cells. Furthermore, while the haploid cells typically budded from the same end, they occasionally reoriented in the channels and budded from the other side. The cells and their lineology were tracked manually. However, the cells may also be tracked automatically, e.g., using software that can identify individual cells (e.g., based on differences in fluorescence intensity).

The chambers allowed for growth of cells to densities higher than that which can normally be obtained in traditional laboratory conditions, for example, up to $1\times10^{10}$ cells/mL. This may facilitate studies of high density cell cultures, such as those found in nature.

With slight modifications in size, the progeny chambers may also be used for the culture of other suspension cells, such as mammalian blood cells or stem cells. By treating the channels with appropriate surface coating(s) (e.g., fibronectin), adherent cells may also be grown in the chambers.

Device fabrication. The microfluidic device used in this example was fabricated as follows. The designs for the chambers were generated in AutoCad. Chrome masks were printed on quartz (HTA Photomask, CA) and soft lithography was used to create polydimethylsiloxane (PDMS) devices. In brief, a SU8 2005 photoresist (MicroChem, Newton, Mass.) was spin-coated onto a silicon wafer (rinsed with methanol and prebaked for 10 minutes at 210° C.) to a final thickness of 5 μm following the protocol described by the manufacturer. A mask was placed on top of the wafer and exposed to UV light for 12 seconds. Exposure of the photoresist to UV light (OAI, San Jose, Calif.) crosslinked the exposed pattern, and the non-exposed photoresist was dissolved away using propylene glycol monomethyl ether acetate (PGMEA). The channel height was confirmed to be 5 μm using a scanning profilometer (Stylus). PDMS was mixed with a crosslinker at a ratio of 10:1, and poured onto the master (Sylgard 184 Silicone Elastomer, Dow Corning, Midland, Mich.). Devices were placed in a vacuum to rid the PDMS of air bubbles for at least 5 minutes before baking at 65° C. overnight. A biopsy punch (0.75 mm diameter, Harris Uni-Core, Ted Pella Inc., Redding, Calif.) was used to punch entry and exit holes in the PDMS. The PDMS was then oxygen plasma treated and bonded to a LabTek chamber with a no. 1.5 coverslip bottom (Nunc). The chambers were found to be most stable during the course of scanning the stage and automated image acquisition.

Loading. The microfluidic device was loaded with the yeast cells as follows. Yeast cells (*S. cerevisiae*) were cultured in YPD at 30° C. to a density of OD600~0.1 and were washed three times in SD media, and diluted 100-fold. A dilute suspension of the yeast cells and perfusion media were loaded into 1 mL plastic syringes (BD, VWR). Needles (luer-lok, 27½ gauge) were connected to the syringes, and the syringes were inverted to remove all air bubbles. The needles were then connected to PE-20 tubing (VWR/ALA Scientific Instruments Inc., Westbury, N.Y.). Syringe pumps (Kent/Harvard Apparatus) were used to control fluid flow. To begin, a piece of tubing was inserted into the exit port for waste collection, and the cell inlet was blocked with a plug. Plugs were fabricated by holding the tip of a 2" long piece of PE-20 briefly in a flame, and then placing the melted end of the tubing between two flat objects. This formed a nice handle making the plug easy to hold. The remaining long end of the tubing was cut to make a short stub. With the plug inserted in the cell entry port, media was flowed through the media entry port of the device until the chambers were filled with fluid. The plug was then replaced with the cell tubing. Cells were loaded using flow rates of 95 μL/hr cells and 15 μL/hr media. When about half of the chambers were filled with single cells, the cell tubing was removed from the syringe needle, and the media flow was increased to 45 μL/hr. This flow rate was maintained for the remainder of the experiment.

The cells were stained by connecting a media syringe to a three-way stopcock (Small Parts). A syringe full of fixation medium/staining medium was attached to the third entry of the stopcock at the end of a growth experiment. The staining media was then flowed through the chambers. The chambers were imaged by placing the chambers on the stage of an inverted microscope (Zeiss Axiovert 200M). A timelapse series of images were acquired at different stage positions. Confocal microscopy was performed on a Zeiss microscope.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
providing a microfluidic network comprising a first region and a microfluidic channel in fluid communication with the first region;
flowing a first fluid in a first direction in the microfluidic channel;
flowing a second fluid in the first direction in the microfluidic channel;
partitioning at least a portion of the first fluid in the first region by flowing the second fluid past the first region, so as to form a first droplet of the first fluid in the first region; and
maintaining the droplet in the first region while the second fluid is flowing in the first direction.

2. A method as in claim 1, wherein the first fluid and the second fluid are immiscible.

3. A method as in claim 1, wherein forming of the first droplet in the first region does not require the use of a surfactant in the first or second fluids.

4. A method as in claim 1, wherein maintaining the first droplet in the first region does not require the use of a surfactant in the first or second fluids.

5. A method as in claim 1, wherein a fluid immiscible with the first fluid is flowed in the microfluidic channel prior to flowing of the first fluid.

6. A method as in claim 1, wherein the first fluid or the second fluid does not comprise a surfactant.

7. A method as in claim 1, wherein forming or maintaining the first droplet in the first region is independent of flow rate of the first fluid in the microfluidic channel.

8. A method as in claim 1, wherein the first droplet can be maintained in the first region in the absence of fluid flowing in the microfluidic channel.

9. A method as in claim 1, wherein the microfluidic channel comprises an upstream portion, a downstream portion, and first and second fluid paths extending from the upstream portion and reconnecting at the downstream portion.

10. A method as in claim 9, wherein the first and second fluid paths have different resistances to flow.

11. A method as in claim 10, wherein the first region is positioned within the first fluid path.

12. A method as in claim 11, wherein the first fluid path has less resistance to flow compared to the second fluid path prior to formation of the first droplet in the first region, and the first fluid path has greater resistance to flow after formation of the first droplet in the first region.

13. A method as in claim 1, wherein the microfluidic network comprises a plurality of regions including the first region, and the method comprises forming a plurality of droplets including the first droplet at the plurality of regions of the microfluidic network, wherein each droplet is formed from a different portion of the first fluid, and each droplet is formed in a separate region in the order in which each portion of the first fluid is introduced into the microfluidic network.

14. A method as in claim 13, further comprising removing the plurality of droplets positioned at regions of the microfluidic network, wherein each droplet is removed in the order the droplet was formed in the microfluidic network.

15. A method as in claim 14, further comprising removing the plurality of droplets positioned at regions of the microfluidic network, wherein each droplet is removed in the reverse order the droplet was formed in the microfluidic network.

16. A method as in claim 1, wherein the first droplet is in fluid communication with the microfluidic channel immediately after the partitioning step.

17. The method of claim 1, wherein the microfluidic channel has a maximum cross sectional dimension of 500 microns or smaller.

18. The method of claim 17, wherein the microfluidic channel has a maximum cross sectional dimension of 100 microns or smaller.

19. The method of claim 1, wherein the first droplet has a volume of less than 1 nL.

20. The method of claim 1, wherein the first fluid is an aqueous fluid.

21. The method of claim 1, wherein the second fluid is an oil.

22. The method of claim 21, wherein the oil is fluorinated.

23. A method, comprising:
providing a microfluidic network comprising a first region and a microfluidic channel in fluid communication with the first region;
flowing a first fluid in a first direction in the microfluidic channel;
flowing a second fluid in the first direction in the microfluidic channel;
partitioning at least a portion of the first fluid in the first region, at least in part through action of the second fluid, so as to form a first droplet of the first fluid in the first region; and flowing a third fluid in the microfluidic channel after flowing of the second fluid;
partitioning at least a portion of the third fluid in a second region so as to form a second droplet of the third fluid in the second region; and
maintaining the droplet in the first region while the second fluid is flowing in the first direction.

24. A method, comprising:
providing a microfluidic network comprising at least a first inlet to a microfluidic channel, a first and a second region for forming a first and a second droplet, respectively, the first and second regions in fluid communication with the microfluidic channel;
flowing a first fluid in the microfluidic channel;
partitioning a first portion of the first fluid in the first region by flowing a second fluid past the first region, so as to form the first droplet in the first region; and
partitioning a second portion of the first fluid at the second region, at least in part through action of the second fluid, so as to form the second droplet at the second region.

25. The method of claim 24, wherein partitioning the second portion of the first fluid in the second region is caused by flowing the second fluid past the second region.

26. A method, comprising:
providing a microfluidic network comprising a first region and a microfluidic channel in fluid communication with the first region, the microfluidic channel comprising an upstream portion, a downstream portion, and first and second fluid paths extending from the upstream portion and reconnecting at the downstream portion, and the first region positioned within the first fluid path;
flowing a first fluid in a first direction in the microfluidic channel;
flowing a second fluid in the first direction in the microfluidic channel;
partitioning at least a portion of the first fluid in the first region, at least in part through action of the second fluid, so as to form a first droplet of the first fluid in the first region; and
maintaining the droplet in the first region while the second fluid is flowing in the first direction,
wherein the first fluid path has less resistance to flow compared to the second fluid path prior to formation of the first droplet in the first region, and the first fluid path has greater resistance to flow after formation of the first droplet in the first region.

* * * * *